United States Patent
Horn

(10) Patent No.: US 12,414,942 B1
(45) Date of Patent: Sep. 16, 2025

(54) COMPOSITIONS, METHODS, AND SYSTEMS FOR TREATING PRESBYOPIA

(71) Applicant: Lenz Therapeutics Operations, Inc., Solana Beach, CA (US)

(72) Inventor: Gerald Horn, Highland Park, IL (US)

(73) Assignee: LENZ THERAPEUTICS OPERATIONS, INC., Solana Beach, CA (US)

( * ) Notice: Subject to any disclaimer, the term of this patent is extended or adjusted under 35 U.S.C. 154(b) by 0 days.

(21) Appl. No.: 18/939,325

(22) Filed: Nov. 6, 2024

Related U.S. Application Data

(63) Continuation-in-part of application No. 18/606,372, filed on Mar. 15, 2024, now abandoned.

(60) Provisional application No. 63/573,626, filed on Apr. 3, 2024, provisional application No. 63/565,668, filed on Mar. 15, 2024, provisional application No. 63/660,858, filed on Jun. 17, 2024, provisional application No. 63/565,672, filed on Mar. 15, 2024, provisional application No. 63/573,630, filed on Apr. 3, 2024, provisional application No. 63/660,853, filed on Jun. 17, 2024, provisional application No. 63/565,674, filed on Mar. 15, 2024, provisional application No. 63/573,632, filed on Apr. 3, 2024, provisional application No. 63/660,848, filed on Jun. 17, 2024, provisional application No. 63/565,679, filed on Mar. 15, 2024, provisional application No. 63/573,636, filed on Apr. 3, 2024, provisional application No. 63/660,969, filed on Jun. 17, 2024, provisional application No. 63/565,687, filed on Mar.

(Continued)

(51) Int. Cl.
*A61K 31/439* (2006.01)
*A61K 9/00* (2006.01)
*A61K 31/498* (2006.01)
*A61P 27/10* (2006.01)

(52) U.S. Cl.
CPC .......... *A61K 31/439* (2013.01); *A61K 9/0048* (2013.01); *A61K 31/498* (2013.01); *A61P 27/10* (2018.01)

(58) Field of Classification Search
CPC .. A61K 31/439; A61K 9/0048; A61K 31/498; A61P 27/10
See application file for complete search history.

(56) References Cited

U.S. PATENT DOCUMENTS

| | | |
|---|---|---|
| 4,474,751 A | 10/1984 | Haslam et al. |
| 4,906,467 A | 3/1990 | Schwartzman et al. |

(Continued)

FOREIGN PATENT DOCUMENTS

| | | |
|---|---|---|
| CN | 101262886 A | 9/2008 |
| CN | 101616640 A | 12/2009 |

(Continued)

OTHER PUBLICATIONS

White, (Ophthalmology, vol. 98, Issue 3), pp. 367-389. (Year: 1991).*

(Continued)

*Primary Examiner* — Carlos A Azpuru
(74) *Attorney, Agent, or Firm* — WILSON SONSINI GOODRICH & ROSATI

(57) ABSTRACT

The present disclosure provides methods comprising administration protocols of an ophthalmological composition, such as comprising aceclidine.

16 Claims, 16 Drawing Sheets

Related U.S. Application Data 15, 2024, provisional application No. 63/573,640, filed on Apr. 3, 2024, provisional application No. 63/660,962, filed on Jun. 17, 2024, provisional application No. 63/565,692, filed on Mar. 15, 2024, provisional application No. 63/573,641, filed on Apr. 3, 2024, provisional application No. 63/660,959, filed on Jun. 17, 2024.

(56) References Cited

U.S. PATENT DOCUMENTS

| | | |
|---|---|---|
| 5,073,560 A | 12/1991 | Wu et al. |
| 5,286,864 A | 2/1994 | Walther et al. |
| 5,451,587 A | 9/1995 | Walther et al. |
| 5,488,050 A | 1/1996 | Neufeld |
| 6,120,758 A | 9/2000 | Siddiqui et al. |
| 6,241,124 B1 | 6/2001 | Hoyt |
| 6,291,466 B1 | 9/2001 | Gwon et al. |
| 6,353,022 B1 | 3/2002 | Schneider et al. |
| 6,410,544 B1 | 6/2002 | Gwon et al. |
| 7,067,261 B2 | 6/2006 | Bencherif et al. |
| 8,299,079 B2 | 10/2012 | Kaufman |
| 8,455,494 B2 | 6/2013 | Kaufman |
| 8,501,800 B2 | 8/2013 | Bowman et al. |
| 8,524,758 B2 | 9/2013 | Benozzi |
| 9,089,562 B2 | 7/2015 | Horn et al. |
| 9,314,427 B2 | 4/2016 | Horn et al. |
| 9,320,709 B2 | 4/2016 | Horn et al. |
| 9,833,441 B2 | 12/2017 | Horn et al. |
| 9,844,537 B2 | 12/2017 | Horn et al. |
| 9,968,594 B2 | 5/2018 | Horn et al. |
| 10,052,313 B2 | 8/2018 | Horn et al. |
| 10,064,818 B2 | 9/2018 | Horn et al. |
| 10,307,408 B2 | 6/2019 | Horn et al. |
| 10,319,154 B1 | 6/2019 | Chakravarthula et al. |
| 10,520,730 B2 | 12/2019 | Bouchier et al. |
| 10,617,763 B2 | 4/2020 | Horn et al. |
| 10,775,628 B2 | 9/2020 | Samec et al. |
| 10,836,760 B2 | 11/2020 | Horn |
| 10,959,990 B2 | 3/2021 | Horn |
| 11,179,327 B2 | 11/2021 | Horn et al. |
| 11,179,328 B2 | 11/2021 | Horn |
| 11,214,569 B2 | 1/2022 | Horn |
| 11,273,150 B2 | 3/2022 | Horn |
| 11,344,538 B2 | 5/2022 | Horn |
| 11,648,247 B1 | 5/2023 | Horn |
| 12,128,036 B2 | 10/2024 | Horn |
| 2002/0035264 A1 | 3/2002 | Kararli et al. |
| 2002/0036264 A1 | 3/2002 | Nakasuji et al. |
| 2003/0104996 A1 | 6/2003 | Li et al. |
| 2003/0140996 A1 | 7/2003 | Thomson |
| 2003/0165545 A1 | 9/2003 | Huth et al. |
| 2003/0232089 A1 | 12/2003 | Singh et al. |
| 2004/0106644 A1 | 6/2004 | Randazzo |
| 2004/0142829 A1 | 7/2004 | Tsao et al. |
| 2005/0196370 A1 | 9/2005 | Yu et al. |
| 2006/0172972 A1 | 8/2006 | Bhushan et al. |
| 2006/0177430 A1 | 8/2006 | Bhushan et al. |
| 2007/0297990 A1 | 12/2007 | Shah et al. |
| 2009/0074786 A1 | 3/2009 | Dor et al. |
| 2009/0156581 A1 | 6/2009 | Dillon et al. |
| 2009/0297565 A1 | 12/2009 | Müller et al. |
| 2009/0297566 A1 | 12/2009 | Brinkman et al. |
| 2010/0016395 A1 | 1/2010 | Benozzi |
| 2010/0310476 A1 | 12/2010 | Tamarkin et al. |
| 2011/0172302 A1 | 7/2011 | Dalton et al. |
| 2011/0250294 A1 | 10/2011 | Tien et al. |
| 2011/0251285 A1 | 10/2011 | Tien et al. |
| 2012/0028910 A1 | 2/2012 | Combal et al. |
| 2012/0094962 A1 | 4/2012 | Skulachev |
| 2012/0165295 A1 | 6/2012 | Painter et al. |
| 2012/0315265 A1 | 12/2012 | Lai et al. |
| 2013/0245030 A1 | 9/2013 | Kaufman |
| 2014/0113946 A1 | 4/2014 | Abad |
| 2014/0200211 A1 | 7/2014 | Abad |
| 2014/0221446 A1 | 8/2014 | Meyer |
| 2014/0378401 A1 | 12/2014 | Horn |
| 2015/0010634 A1 | 1/2015 | Knappe et al. |
| 2015/0065511 A1* | 3/2015 | Horn .................. A61K 31/498 514/249 |
| 2015/0290125 A1 | 10/2015 | Horn et al. |
| 2015/0290126 A1 | 10/2015 | Horn et al. |
| 2015/0290216 A1 | 10/2015 | Khopade et al. |
| 2016/0008278 A1 | 1/2016 | Horn et al. |
| 2016/0008337 A1 | 1/2016 | Horn et al. |
| 2016/0018671 A1 | 1/2016 | Waite et al. |
| 2016/0193193 A1 | 7/2016 | Horn et al. |
| 2016/0193194 A1 | 7/2016 | Horn et al. |
| 2016/0346259 A1 | 12/2016 | Horn et al. |
| 2016/0354315 A1 | 12/2016 | Li |
| 2018/0140708 A1 | 5/2018 | Horn et al. |
| 2018/0228729 A1 | 8/2018 | Lee et al. |
| 2018/0235946 A1 | 8/2018 | Horn et al. |
| 2018/0280363 A1 | 10/2018 | Horn et al. |
| 2019/0000755 A1 | 1/2019 | Horn et al. |
| 2019/0038609 A1 | 2/2019 | Horn |
| 2019/0240152 A1 | 8/2019 | Horn et al. |
| 2019/0321337 A1 | 10/2019 | Robinson et al. |
| 2020/0115377 A1 | 4/2020 | Horn |
| 2020/0146976 A1 | 5/2020 | Horn |
| 2020/0181136 A1 | 6/2020 | Horn |
| 2020/0188369 A1 | 6/2020 | Horn |
| 2020/0246310 A1 | 8/2020 | Pitlick et al. |
| 2020/0281906 A1 | 9/2020 | Horn |
| 2020/0308168 A1 | 10/2020 | Banerjee et al. |
| 2021/0038574 A1 | 2/2021 | Horn |
| 2021/0251970 A1 | 8/2021 | Horn |
| 2022/0031608 A1 | 2/2022 | Horn |
| 2022/0105090 A1 | 4/2022 | Horn |
| 2022/0233434 A1 | 7/2022 | Horn |
| 2022/0347170 A1 | 11/2022 | Horn |
| 2023/0151000 A1 | 5/2023 | Horn |
| 2023/0190738 A1 | 6/2023 | Horn |
| 2023/0190739 A1 | 6/2023 | Horn |
| 2023/0248644 A1 | 8/2023 | Horn |
| 2023/0310392 A1 | 10/2023 | Horn |
| 2023/0398064 A1 | 12/2023 | Horn et al. |
| 2023/0398113 A1 | 12/2023 | Horn |
| 2023/0404912 A1 | 12/2023 | Horn |
| 2023/0414494 A1 | 12/2023 | Horn |
| 2023/0414587 A1 | 12/2023 | Horn |
| 2024/0091207 A1 | 3/2024 | Horn |

FOREIGN PATENT DOCUMENTS

| | | |
|---|---|---|
| EP | 0197718 A2 | 10/1986 |
| JP | S62194861 A | 8/1987 |
| JP | H06211666 A | 8/1994 |
| JP | H07330604 A | 12/1995 |
| JP | 2852607 B2 | 2/1999 |
| JP | H11292151 A | 10/1999 |
| JP | 2002521429 A | 7/2002 |
| JP | 2004168709 A | 6/2004 |
| JP | 2008536866 A | 9/2008 |
| JP | 2010514517 A | 5/2010 |
| JP | 2012508793 A | 4/2012 |
| WO | WO-9612711 A1 | 5/1996 |
| WO | WO-0006135 A2 | 2/2000 |
| WO | WO-02080915 A2 | 10/2002 |
| WO | WO-02100437 A2 | 12/2002 |
| WO | WO-2007011874 A2 | 1/2007 |
| WO | WO-2008083118 A1 | 7/2008 |
| WO | WO-2009015286 A2 | 1/2009 |
| WO | WO-2009077736 A2 | 6/2009 |
| WO | WO-2010070664 A2 | 6/2010 |
| WO | WO-2010125416 A1 | 11/2010 |
| WO | WO-2010135731 A1 | 11/2010 |
| WO | WO-2012119070 A2 | 9/2012 |
| WO | WO-2013041967 A2 | 3/2013 |
| WO | WO-2014161002 A2 | 10/2014 |
| WO | WO-2015031186 A1 | 3/2015 |
| WO | WO-2015031187 A1 | 3/2015 |
| WO | WO-2015094392 A1 | 6/2015 |
| WO | WO-2016205068 A1 | 12/2016 |

(56) References Cited

FOREIGN PATENT DOCUMENTS

| | | | |
|---|---|---|---|
| WO | WO-2016205069 A1 | 12/2016 |
| WO | WO-2016205071 A1 | 12/2016 |
| WO | WO-2017053646 A1 | 3/2017 |
| WO | WO-2017160548 A1 | 9/2017 |
| WO | WO-2019135927 A1 | 7/2019 |
| WO | WO-2020076769 A1 | 4/2020 |
| WO | WO-2020117637 A1 | 6/2020 |
| WO | WO-2020219707 A1 | 10/2020 |
| WO | WO-2022081204 A1 | 4/2022 |
| WO | WO-2022232205 A1 | 11/2022 |
| WO | WO-2023091439 A1 | 5/2023 |
| WO | WO-2023114347 A1 | 6/2023 |
| WO | WO-2024220441 A1 | 10/2024 |

OTHER PUBLICATIONS

Glaucoma Research Foundation (Year: 2022).*
Presbyopia, Mayo Foundation for Medical Education. (Year: 1998).*
Aceclidine (Hydrochloride) Item No. 1790. Product Information. Cayman Chemical Company (1 pg) (Dec. 2, 2022).
Akorn Incorporated MSDS: Tropicacyl (R); Rev. 11-11 (date unknown).
Barot et al. Prodrug Strategies. Ocular Drug Delivery Med. Chem. 8(4):753-768 (2012).
Berge, Stephen M. et al. Pharmaceutical Salts. Journal of Pharmaceutical Sciences 66(1):1-19 (1977).
Bijsluiter: Glaucocare. Available at https://consumed.nl/bijsluiters/glaucocare. Machine Translation Provided (Retrieved Sep. 12, 2018).
CAS printout for Mashkovskii, The Relation Between the Chemical Structure and Pharmacological Activity of Some Esters of 3-Hydroxyquinuclidine (Quinuclidine-3-ol), Proc. Intern. Pharmacol., 7:359-366 (1961).
Charman, W. Neil. Pinholes and presbyopia: solution or sideshow? Ophthalmic Physiol Opt 39(1):1-10 (2019).
Chung et al., The effect of dioptric blur on reading performance. Vision Res47(12):1584-94 (2007).
Co-pending U.S. Appl. No. 18/606,372, inventor Horn; Gerald, filed Mar. 15, 2024.
Co-pending U.S. Appl. No. 18/606,417, inventor Horn; Gerald, filed Mar. 15, 2024.
Co-pending U.S. Appl. No. 18/606,433, inventor Horn; Gerald, filed Mar. 15, 2024.
Co-pending U.S. Appl. No. 18/606,475, inventor Horn; Gerald, filed Mar. 15, 2024.
Co-pending U.S. Appl. No. 18/606,489, inventor Horn; Gerald, filed Mar. 15, 2024.
Co-pending U.S. Appl. No. 18/606,509, inventor Horn; Gerald, filed Mar. 15, 2024.
Co-pending U.S. Appl. No. 18/753,403, inventors Olsson; Shawn et al., filed Jun. 25, 2024.
Co-pending U.S. Appl. No. 18/763,722, inventors Horn; Gerald et al., filed Jul. 3, 2024.
Co-pending U.S. Appl. No. 18/765,066, inventors Horn; Gerald et al., filed Jul. 5, 2024.
Co-pending U.S. Appl. No. 18/765,156, inventors Horn; Gerald et al., filed Jul. 5, 2024.
Co-pending U.S. Appl. No. 18/766,429, inventors Horn; Gerald et al., filed Jul. 8, 2024.
Cowan et al., Clinical evaluation of a new mydriatic-mydrilate. Br J Ophthalmol 46(12):730-6 (1962).
Davidson., General medicine and visual side effects. Br Med J 1(6166):821 (1979).
Diamonds—BCdVA and Refraction Guideline, Version 1.0, Jan. 12, 2016 (10 pages).
Drance et al., Dose response of human intraocular pressure to aceclidine. Arch Ophthalmol 88(4):394-6 (1972).
Drug information Q&A "Q29". What is the expiry date of drugs and how to store them properly?, Japan Pharmaceutical Manufacturers Association [online], Mar. 2014, [retrieved on Mar. 25, 2024], Retrieved from the Internet: URL: https://www.jpma.or.jp/about_medicine/guide/med_qa/q29.html (English translation provided).
Edwards., Behaviour of the fellow eye in acute angle-closure glaucoma. Br J Ophthalmol 66(9):576-9 (1982).
Edwards et al., Effect of brimonidine tartrate 0.15% on night-vision difficulty and contrast testing after refractive surgery, J Cataract Refract Surg. 34(9):1538-41 (2008).
Ehlert et al. The interaction of the enantiomers of aceclidine with subtypes of the muscarinic receptor. J Pharmacol Exp Ther 279(3):1335-1344 (1996).
Fechner et al., Accomodative effects of aceclidine in the treatment of glaucoma. Amer J Ophth. 79 (1):104-106 (1975).
Francois et al. Ultrasonographic study of the effect of different miotics on the eye components. Ophthalmologica 175(6):328-338 (1977).
Fricke et al. Global Prevalence of Presbyopia and Vision Impairment from Uncorrected Presbyopia: Systematic Review, Meta-analysis, and Modelling. Ophthalmology 125(10):1492-1499 (2018).
Gardiner., ABC of Ophthalmology: accidents and first aid. Br Med J 2(6148):1347-50 (1978).
Gardiner., ABC of Ophthalmology: Methods of examination. Br Med J 2(6152):1622-6 (1978).
Glaucadrine, poudre et solvant pour collyre en solution, boite de 1 acon de lyophilisat + acon le solvant de 10 ml GI. Available at Http://www.doctissimo.fr/medicament-GLAUCADRINE.htm Machine translation provided (Retrieved Sep. 12, 2018).
Glaunorm toma all'Indice farmaci. Available at http://www.anibaldi.eu/farmaci/schedetecniche/GLAUNORM.html. Machine Translation Provided (last updated Dec. 15, 2012).
Grünberger et al., The pupillary response test as a method to differentiate various types of dementia. Neuropsychiatr 23(1):52-57 (2009).
Hoyng et al., The combination of guanethidine 3% and adrenaline 0.5% in 1 eyedrop (GA) in glaucoma treatment. Br J Ophthalmol 63(1):56-62 (1979).
Ishikawa et al. Selectivity of muscarinic agonists including (+/−)-aceclidine and antimuscarinics on the human intraocular muscles. J Ocul Pharmacol Ther 14(4):363-373 (1998).
Jiao, Jim. Polyoxyethylated nonionic surfactants and their applications in topical ocular drug delivery. Advanced Drug Delivery Reviewed 60:1663-1673 (2008).
Kaufman et al. Presbyopia and Glaucoma: Two Diseases, One Pathophysiology? The 2017 Friedenwald Lecture. Invest Ophthalmol Vis Sci 60(5):1801-1812 (2019).
Kibbe, Arthur H. Handbook of Pharmaceutical Excipients. 3rd Edition. American Pharmaceutical Association and Pharmaceutical Press :416-419 (2000).
Krise et al. A novel prodrug approach for tertiary amines. 2. Physicochemical and in vitro enzymatic evaluation of selected N-phosphonooxymethyl prodrugs. J Pham Sci 88(9):922-927 (1999).
Latanoprost Label (2006).
Lubrizol Pharmaceutical Bulletin 21 (Lubrizol Advanced Materials, Inc.) May 31, 2011.
Mayama et al. Myopia and advanced-stage open-angle glaucoma. Ophthalmology 109(11):2072-2077 (2002).
Mayo Clinic: Tropicamide (Opthalmic Route). Available at, http://www.mayoclinic.org/drugs-supplements/tropicamide-ophthalmic-route/description/drg-20066481 (Retrieved on Dec. 2014).
Mäntylä et al. Design, synthesis and in vitro evaluation of novel water-soluble prodrugs of buparvaquone. Eur J Pharm Sci 23(2):151-158 (2004).
Mohan et al., Optimal dosage of cyclopentolate 1% for cycloplegic refraction in hypermetropes with brown irides. Indian J Ophthalmol 59(6):514-6 (2011).
Muller and R.P. Dessing (Eds.) 4th Edition, European Drug Index, European Society of Clinical Pharmacy, Jeutscher Apotheker Verlag Suttgart (p. 550) (1997).
Nayak et al., A comparison of cycloplegic and manifest refractions on the NR-1000F (an objective Auto Refractometer). Br J Ophthalmol 71(1):73-5 (1987).
Park., The comparison of mydriatic effect between two drugs of different mechanism. Korean J Ophthalmol 23(1):40-2 (2009).

(56) References Cited

OTHER PUBLICATIONS

PCT/US2014/052256 International Search Report and Written Opinion dated Dec. 18, 2014.
PCT/US2016/036687 International Search Report and Written Opinion dated Sep. 9, 2016.
PCT/US2016/036692 International Search Report and Written Opinion dated Sep. 22, 2016.
PCT/US2016/036694 International Search Report and Written Opinion dated Oct. 26, 2016.
PCT/US2017/021244 International Search Report and Written Opinion dated May 22, 2017.
PCT/US2019/055116 International Search Report and Written Opinion dated Dec. 19, 2019.
PCT/US2019/063923 International Invitation to Pay Additional Fees dated Feb. 3, 2020.
PCT/US2019/063923 International Search Report and Written Opinion dated Apr. 23, 2020.
PCT/US2021/029536 International Search Report and Written Opinion dated Aug. 9, 2021.
PCT/US2022/026435 International Invitation to Pay Additional Fees dated Jul. 5, 2022.
PCT/US2022/026435 International Search Report and Written Opinion dated Sep. 28, 2022.
PCT/US2022/050028 International Search Report and Written Opinion dated Mar. 2, 2023.
PCT/US2024/024819 International Search Report and Written Opinion dated Jul. 15, 2024.
Pramanik et al. A new route to cevimeline. Tetrahedron Letters 54(24):3043-3045 (2013).
Primožič et al. Influence of the acyl moiety on the hydrolysis of quinuclidinium esters catalyzed by butyrylcholinesterase. Croatica Chemica Acta 84(2):245-249 (2011).
Prospectus/Technical Sheet for Glaucostat Josefa Valcarecel Glaucostat® 2% colirio (2000).
PubChem 233021624 deposited on Feb. 12, 2015.
PubChem 427198483 deposited Aug. 13, 2020 (Aug. 13, 2020).
PubChem CID-22416839, Dec. 5, 2007.
PubChem-CID-22416839, Create Date: Dec. 5, 2007 (Modified Jul. 15, 2023).
Randazzo et al., Pharmacological management of night vision disturbances after refractive surgery Results of a randomized clinical trial. J Cataract Refract Surg 31(9):1764-1772 (2005).
Romano., Double-blind cross-over comparison of aceclidine and pilocarpine in open-angle glaucoma. Br J Ophthalmol 54(8):510-21 (1970).
Santvliet, et al. Determinants of Eye Drop Size. Survey of Ophthamology 49(2):197-213 (2004).
Schuster, Bradley L. Is There a Best Technique for Putting in Eye Drops ?. Glaucoma Research Foundation, Mar. 23, 2022; [retrieved on Jun. 14, 2024]. Available at URL: https://glaucoma.org/articles/is-there-a-best-technique-for-putting-in-eye-drops pp. 1-3.
Smith et al., Subsensitivity to cholinoceptor stimulation of the human iris sphincter in situ following acute and chronic administration of cholinomimetic miotic drugs. Br J Pharmacol 69(3):513-8 (1980).
Stella. Prodrugs: Some Thoughts and Current Issues. J Pharm Sci 99(12):4755-4765 (2010).

Tataru et al., Antiglaucoma pharmacotherapy. J Med Life 5(3):247-51 (2012).
Trinavarat et al., Effective pupil dilatation with a mixture of 0.75% tropicamide and 2.5% phenylephrine: A randomized controlled trial. Indian J Ophthalmol 57(5):351-4 (2009).
U.S. Appl. No. 18/606,372 Office Action dated Jun. 20, 2024.
U.S. Appl. No. 18/606,372 Restriction Requirement dated Jun. 4, 2024.
U.S. Appl. No. 18/606,417 Office Action dated Jun. 13, 2024.
U.S. Appl. No. 18/606,433 Office Action dated Jun. 26, 2024.
U.S. Appl. No. 18/606,475 Office Action dated Jul. 10, 2024.
U.S. Appl. No. 18/606,475 Restriction Requirement dated May 9, 2024.
U.S. Appl. No. 18/606,509 Restriction Requirement dated May 13, 2024.
Valcarcel, Josefa. Glaucostat(R) 2% colirio. Machine translation provided (Retrieved Oct. 10, 2023).
Varma et al. Concentration of Latanoprost Ophthalmic Solution after 4 to 6 Weeks' Use in an Eye Clinic Setting. Invest Ophthalmol Vis Sci. 47(1):222-225 (2006).
Ward et al., 1,2,5-Thiadiazole analogues of aceclidine as potent ml muscarinic agonists. J Med Chem 41(3):379-392 (1988).
White, et al. Effect of Blinking on Tear Elimination as Evaluated by Dacryoscintigraphy. Ophthalmology 98(3):367-369 (1991).
Wood et al., Pupil dilatation does affect some aspects of daytime driving performance. Br J Ophthalmol (11):1387-90 (2003).
Xu, Renfeng et al. Effect of Target Luminance on Optimum Pupil Diameter for Presbyopic Eyes. Optom Vis Sci 93(11):1409-1419 (2016).
Zhang et al. Reactive impurities in large and small molecule pharmaceutical excipients—A review. TrAC Trends in Analytical Chemistry 101:34-42 (2018).
Zimmerman et al. Side Effects and Ways to Avoid Them. Ophthalmology 89(1):P76-80 (1982).
Presbyopia, Treatment of Presbyopia Mayo Foundation for Medical Education. (Year: 1998).
U.S. Appl. No. 17/552,694 Office Action dated Feb. 12, 2025.
U.S. Appl. No. 18/606,372 Office Action dated Jan. 7, 2025.
Barman, Purna Chandra et al. An Overview of Non-Newtonian Fluid. International Journal of Applied Science and Engineering 4(2):97-101 (2016).
PubChem SID 500830745. Talsaclidine. Available from: https://pubchem.ncbi.nlm.nih.gov/substance/500830745 (2024).
U.S. Appl. No. 17/730,376 Office Action dated Mar. 7, 2025.
U.S. Appl. No. 18/369,737 Office Action dated Mar. 28, 2025.
PCT/US2025/019824 International Search Report and Written Opinion dated May 20, 2025.
PCT/US2025/019822 International Search Report and Written Opinion dated May 20, 2025.
PCT/US2025/019809 International Search Report and Written Opinion dated May 20, 2025.
PCT/US2025/019828 International Search Report and Written Opinion dated May 20, 2025.
PCT/US2025/019866 International Search Report and Written Opinion dated May 20, 2025.
PCT/US2025/019860 International Search Report and Written Opinion dated May 20, 2025.

* cited by examiner ns. In certain embodiments provided herein is a method of treating presbyopia with a concomitant improvement in distance vision in an individual, the method comprising administering an ophthalmological composition to an eye (e.g., an ocular surface thereof) of the individual.

COMPOSITIONS, METHODS, AND SYSTEMS FOR TREATING PRESBYOPIA

CROSS REFERENCE TO RELATED APPLICATIONS

This application is a continuation-in-part of U.S. application Ser. No. 18/606,372, filed on Mar. 15, 2024, and claims priority to and the benefit of U.S. Provisional Application No. 63/565,668, filed on Mar. 15, 2024, 63/573,626, filed on Apr. 3, 2024, 63/660,858, filed on Jun. 17, 2024, 63/565,672, filed on Mar. 15, 2024, 63/573,630, filed on Apr. 3, 2024, 63/660,853, filed on Jun. 17, 2024, 63/565,674, filed on Mar. 15, 2024, 63/573,632, filed on Apr. 3, 2024, 63/660,848, filed on Jun. 17, 2024, 63/565,679, filed on Mar. 15, 2024, 63/573,636, filed on Apr. 3, 2024, 63/660,969, filed on Jun. 17, 2024, 63/565,687, filed on Mar. 15, 2024, 63/573,640, filed on Apr. 3, 2024, 63/660,962, filed on Jun. 17, 2024, 63/565,692, filed on Mar. 15, 2024, 63/573,641, filed on Apr. 3, 2024, and 63/660,959, filed on Jun. 17, 2024, each of which is incorporated herein by reference in its entirety.

BACKGROUND

Presbyopia is a type of refractive error that causes close objects to gradually appear out of focus as the eye ages. Presbyopia affects about 26% of the world's population, and treatment options include: corrective eyeglasses or contact lenses, refractive surgery, and lens implants. Most adults will experience presbyopia at some point in their lives, such as after reaching 40 years old.

SUMMARY

Provided in certain embodiments herein are systems, compositions, and methods, such as for treating ocular disorders, such as presbyopia. In some embodiments, provided herein is a method of improving vision. In some embodiments, provided herein is a method of improving near vision. In some embodiments, provided herein is a method of improving distance vision. In some embodiments, provided herein is a method of treating presbyopia. In some embodiments, a composition provided herein comprises a composition comprising a miotic (e.g., aceclidine or a salt thereof). In some embodiments, a system provided herein comprises such a composition (e.g., and a vessel containing the composition). In some embodiments, a method provided herein comprises administering such a composition, such as to an eye (e.g., surface) of an individual.

Provided in some embodiments herein is a method of treating presbyopia in an individual (e.g., in need thereof). In certain embodiments provided herein is a method of treating presbyopia in an individual, the method comprising administering an ophthalmological composition to an eye (e.g., an ocular surface thereof) of the individual.

Provided in some embodiments herein is a method of treating presbyopia with a concomitant improvement in myopia in an individual (e.g., in need thereof). In certain embodiments provided herein is a method of treating presbyopia with a concomitant improvement in myopia in an individual, the method comprising administering an ophthalmological composition to an eye (e.g., an ocular surface thereof) of the individual.

Provided in some embodiments herein is a method of treating presbyopia with a concomitant improvement in distance vision in an individual (e.g., in need thereof). In certain embodiments provided herein is a method of treating presbyopia with a concomitant improvement in distance vision in an individual, the method comprising administering an ophthalmological composition to an eye (e.g., an ocular surface thereof) of the individual.

Provided in some embodiments herein is a method of treating presbyopia in an individual, the method comprising administering to a first eye of the individual a first drop of an ophthalmic composition comprising aceclidine or a salt thereof. In some embodiments, the method comprises administering to the first eye a second drop of the ophthalmic composition. In specific embodiments, the second drop is administered to the first eye about 2 minutes after the first drop is administered to the first eye. In some embodiments, the individual previously had ocular surgery in the first eye. In specific embodiments, the ocular surgery is laser assisted in situ keratomileusis (LASIK) surgery or photorefractive keratectomy (PRK) surgery.

Provided in some embodiments herein is a method of treating presbyopia in an individual, the method comprising administering an ophthalmic composition to an eye of the individual. In specific embodiments, the ophthalmic composition comprising a miotic (e.g., pupil selective miotic, such as relative to ciliary muscle). In some embodiments, the eye of the individual having previously undergone ocular surgery.

Provided in some embodiments herein is a method of treating presbyopia in an individual, the method comprising administering an ophthalmic composition to an eye of the individual. In specific embodiments, the ophthalmic composition comprising aceclidine or a salt thereof. In some embodiments, the eye of the individual having previously undergone ocular surgery.

Provided in some embodiments herein is a method of treating presbyopia in an individual, the method comprising administering a first drop of an ophthalmic composition (such as described herein) to an eye of the individual. In some embodiments, the method comprises subsequently administering a second drop of the ophthalmic composition to the eye of the individual. In some embodiments, the ophthalmic composition comprises aceclidine or a salt thereof. In some embodiments, the second drop is administered to the eye of the individual about 2 minutes after the first drop is administered to the eye.

Provided in some embodiments herein is a method of treating presbyopia in an individual, the method consisting essentially of administering a first drop of an ophthalmic composition (such as described herein) to an eye of the individual. In some embodiments, the method comprises subsequently administering a second drop of the ophthalmic composition to the eye of the individual. In some embodiments, the ophthalmic composition comprises aceclidine or a salt thereof. In some embodiments, the second drop is administered to the eye of the individual about 2 minutes after the first drop is administered to the eye.

Provided in some embodiments herein is a method of treating presbyopia and improving distance vision in an individual, the method comprising administering a first drop of an ophthalmic composition (such as described herein) to an eye of the individual and subsequently administering a second drop of the ophthalmic composition to the eye of the individual. In some embodiments, the ophthalmic composition comprises aceclidine or a salt thereof. In some embodiments, the second drop is administered to the eye of the individual about 2 minutes after the first drop is administered to the eye.

Provided in some embodiments herein is a method of providing a pupil size of an eye of an individual to less than 2 millimeters (mm) in the eye of the individual (e.g., for at least 9 hours), the method comprising administering an ophthalmic composition comprising a miotic agent (such as described herein) to an eye of the individual.

Provided in some embodiments herein is a method for treating presbyopia, the method comprising instill one drop of an ophthalmic composition comprises aceclidine or a salt thereof in each eye followed by a second drop in each eye about two (2) minutes later for an effect of at least 10 hours.

Provided in some embodiments herein is a method of treating presbyopia in an individual, the method comprising administering to a first eye of the individual a first drop of an ophthalmic composition comprising aceclidine or a salt thereof. In some embodiments, the method comprises administering to the first eye a second drop of the ophthalmic composition (such as described herein). In some embodiments, the second drop is administered to the first eye about 2 minutes after the first drop is administered to the first eye.

Provided in some embodiments herein is a method of treating presbyopia in a first eye of an individual, the method consisting essentially of administering to a first eye of the individual a first drop of an (e.g., a sterile, preservative-free) ophthalmic composition comprising aceclidine or a salt thereof in a concentration of about 1 wt. % to about 2 wt. %. In some embodiments, the method comprises administering to the first eye a second drop of the ophthalmic composition (such as described herein). In some embodiments, the second drop is administered to the first eye about 2 minutes after the first drop is administered to the first eye.

Provided in some embodiments herein is a method of treating presbyopia in an individual, the method comprising administering an ophthalmic composition (such as described herein) to an eye of the individual. In some embodiments, the composition comprises aceclidine and a pH of about 4.5 to about 5.5. In some embodiments, the composition has a room temperature when administered to the eye of the individual.

Provided in some embodiments herein is a method of treating presbyopia in an individual, the method comprising administering an ophthalmic composition (such as described herein) to an eye of the individual. In some embodiments, the composition comprises aceclidine and has a pH of about 4.5 to about 5.5. In some embodiments, the composition has been stored at room temperature for up to 6 months prior to administration. In some embodiments, the ophthalmic composition remains ophthalmically acceptable and suitable for treating presbyopia when administered to the eye for at least 6 months at room temperature.

Provided in some embodiments herein is a method of treating presbyopia in an individual, the method comprising storing an ophthalmic composition (such as described herein) at a temperature of room temperature for up to 14 days (e.g., up to 3 months). In some embodiments, the method comprises administering the ophthalmic composition to an eye of the individual. In some embodiments, the composition comprises aceclidine and has a pH of about 4.5 to about 5.5. In some embodiments, the composition has been stored at room temperature for up to 14 days (e.g., up to 3 months) prior to administration of the ophthalmic composition to the eye. In some embodiments, the ophthalmic composition remains ophthalmically acceptable and suitable for treating presbyopia when administered to the eye for at least 14 days (e.g., at least 3 months) at room temperature.

Provided in some embodiments herein is a method of treating presbyopia in an individual, the method comprising administering an ophthalmic composition (such as described herein) to an eye of the individual. In some embodiments, the composition comprises aceclidine and a pH of about 4.5 to about 5.5. In some embodiments, the composition has been stored at 2 degrees Celsius to 8 degrees Celsius up to 12-18 months before being stored at room temperature and having been stored at room temperature for up to 6 months prior to administration. In some embodiments, the ophthalmic composition remains ophthalmically acceptable and suitable for treating presbyopia when administered to the eye for at least 12 months at 2 degrees Celsius to 8 degrees Celsius and 6 months at room temperature.

Provided in some embodiments herein is a method of treating presbyopia in an individual, the method comprising administering an ophthalmic composition (such as described herein) to an eye of the individual. In some embodiments, the composition comprises aceclidine and a pH of about 4.5 to about 5.5. In some embodiments, the composition has been stored at 2 degrees Celsius to 8 degrees Celsius up to 12-18 months before being stored at room temperature and having been stored at room temperature for up to 14 days (e.g., at least 3 months) prior to administration. In some embodiments, the ophthalmic composition remains ophthalmically acceptable and suitable for treating presbyopia when administered to the eye for at least 12 months at 2 degrees Celsius to 8 degrees Celsius and 14 days (e.g., at least 3 months) at room temperature.

Provided in some embodiments herein is a method of treating presbyopia in an individual, the method comprising administering an ophthalmic composition (such as described herein) to an eye of the individual. In some embodiments, the composition comprises aceclidine and a pH of about 4.5 to about 5.5. In some embodiments, the composition has been stored at greater than 25 degrees Celsius and up to 40 degrees Celsius for up to 8 days prior to administration. In some embodiments, the ophthalmic composition remains ophthalmically acceptable and suitable for treating presbyopia when administered to the eye for at least 8 days at 40 degrees Celsius. In some instances, the ability to store a composition for a few days of the 40 degrees Celsius can provide a substantial commercial benefit, such as allowing the composition to be shipped using lower cost and/or more conventional shipping methods, including shipping to pharmacies or directly to end-users.

Provided in some embodiments herein is a method of treating presbyopia in an individual, the method comprising storing an ophthalmic composition (such as described herein) at a temperature of about 2° C. to about 8° C. In some embodiments, the ophthalmic composition comprises aceclidine and having a pH of 4.5 to 5.5. In some embodiments, prior to storing at a temperature of about 2° C. to about 8° C., the ophthalmic composition comprises an initial concentration of the aceclidine, wherein the initial concentration of aceclidine in the ophthalmic composition is about 1.35 wt. % to about 1.75 wt. %, based on the free base concentration of aceclidine in the ophthalmic composition. In some embodiments, the method comprises after storing the ophthalmic composition at a temperature of about 2° C. to about 8° C., storing the ophthalmic composition at room temperature. In some embodiments, the ophthalmic composition comprising at least 90% of the initial concentration of aceclidine for at least 12 months at 2 degrees Celsius to 8 degrees Celsius and 14 days (e.g., at least 3 months) at room temperature. In some embodiments, the method comprises administering the ophthalmic composition to an eye of the individual.

Provided in some embodiments herein is a method of treating presbyopia in an individual, the method comprising storing an ophthalmic composition (such as described herein) at a temperature of about 2° C. to about 8° C. In some embodiments, the ophthalmic composition comprising aceclidine and having a pH of 4.5 to 5.5. In some embodiments, the method comprises after storing the ophthalmic composition at a temperature of about 2° C. to about 8° C., storing the ophthalmic composition at room temperature for up to 14 days (e.g., 3 months). In some embodiments, the method comprises administering the ophthalmic composition to an eye of the individual, wherein prior to storing at a temperature of about 2° C. to about 8° C., the ophthalmic composition comprises an initial concentration of the aceclidine, the initial concentration of aceclidine in the ophthalmic composition being about 1.35 wt. % to about 1.75 wt. %, based on the free base concentration of aceclidine in the ophthalmic composition. In some embodiments, the ophthalmic composition comprising at least 90% of the initial concentration of aceclidine for at least 12 months at 2 degrees Celsius to 8 degrees Celsius and 14 days (e.g., at least 3 months) at room temperature. In some embodiments, the ophthalmic composition is preservative-free (free of antimicrobial preservative). In some embodiments, the ophthalmic composition comprises the aceclidine in solution.

Provided in some embodiments herein is a system comprising a single-patient-use container (such as described herein) and an ophthalmic composition (such as described herein). In some embodiments, the ophthalmic composition comprises aceclidine or a salt thereof. In some embodiments, the single-patient-use container comprises an enclosed chamber, the ophthalmic composition being configured within the enclosed chamber. In some embodiments, the single-patient-use container is configured to be irreversibly opened, and single-patient-use container being configured, when open, to dispense a first drop and a second drop of the ophthalmic composition through an opening (e.g., formed when the container is irreversibly opened).

Provided in some embodiments herein is a method for treating presbyopia in an individual, the method comprising opening a first single-patient-use container (such as described herein) on a first day. In some embodiments, the method comprises subsequently administering to a first eye of the individual a first drop and a second drop of an ophthalmic composition (such as described herein) to the first eye of the individual. In some embodiments, the second drop is administered to the first eye 2 minutes after the first drop is administered to the first eye. In some embodiments, the ophthalmic composition comprises aceclidine or a salt thereof.

Provided in some embodiments herein is a method for improving distance vision in an individual, the method comprising opening a first single-patient-use container (such as described herein) on a first day and subsequently administering to a first eye of the individual a first drop of an ophthalmic composition (such as described herein) to the first eye of the individual. In some embodiments, the method comprises subsequently administering to the first eye of the individual a second drop of an ophthalmic composition to the first eye of the individual. In some embodiments, the second drop is administered 2 minutes after the first drop is administered to the first eye. In some embodiments, the ophthalmic composition comprises aceclidine or a salt thereof.

Provided in some embodiments herein is a system comprising a single-use container (such as described herein) and about 0.5 ml of a (e.g., sterile) ophthalmic composition (such as described herein). In some embodiments, the ophthalmic composition comprises aceclidine or a salt thereof in a concentration of about 1 wt. % to about 2 wt. %. In some embodiments, the single-use container comprises an enclosed chamber, the ophthalmic composition being configured within the enclosed chamber. In some embodiments, the single-use container is configured to be irreversibly opened, and single-use container being configured, when open, to dispense a first drop and a second drop of the ophthalmic composition through an opening (e.g., formed when the container is irreversibly opened). In some embodiments, the ophthalmic composition does not include an antimicrobial preservative.

Provided in some embodiments herein is a method of treating presbyopia in an individual wearing a contact lens, the method comprising administering one or more drop of an ophthalmic composition comprising aceclidine to an eye of the individual. In some embodiments, the method comprises removing the contact lens from the eye before administering the ophthalmic composition to the eye. In some embodiments, the method comprises reinserting the contact lens onto the eye about 10 minutes or more after administering the ophthalmic composition.

Provided in some embodiments herein is a method of reducing a corrective lens wear time in an individual, the method comprising administering a composition comprising a miotic (such as described herein) to an eye of the individual. In some embodiments, the miotic is pupil selective (e.g., such as relative to ciliary muscle).

Provided in some embodiments herein is a method of treating presbyopia in an individual wearing a contact lens, the method comprising administering to an eye of the individual a first drop and a second drop of a (e.g., sterile) ophthalmic composition (such as described herein). In some embodiments, the second drop is administered to the eye about 2 minutes after the first drop. In some embodiments, the (e.g., sterile, preservative-free) ophthalmic composition comprises aceclidine in a concentration of about 1 wt. % to about 2 wt. %. In some embodiments, the method comprises removing the contact lens from the eye before administering the first drop of the ophthalmic composition to the eye. In some embodiments, the method comprises reinserting the contact lens onto the eye about 10 minutes or more after administering the second drop of the ophthalmic composition (such as described herein) to the eye. In some embodiments, the ophthalmic composition does not include an antimicrobial preservative.

Provided in some embodiments herein is a method of increasing comfortable screen time in an individual, the method comprising administering an ophthalmic composition comprising a miotic (such as described herein) to an eye of the individual. In some embodiments, the ophthalmic composition is a pupil selective miotic composition, relative to ciliary muscle.

In some embodiments, a method provided herein comprises (e.g., topically) administering a first drop of an ophthalmological composition to an eye (e.g., an ocular surface thereof) of an individual and subsequently administering a second drop of the ophthalmological composition to the eye (e.g., an ocular surface thereof) of the individual. In some embodiments, a composition provided herein comprises a composition comprising a miotic (e.g., aceclidine or a salt thereof). In some embodiments, the first and second drop are administered about 2 minutes apart.

In certain instances, providing a first drop and a second drop of a composition provided herein to an eye of an individual provides improved efficacy (e.g., duration) of an effect provided by the composition, such as increased duration of an improvement in visual acuity at 40 cm (e.g., relative to administration of a single drop of the composition). In some instances, such an enhanced effect can be provided when the drops are administered as little 5 minutes apart, or less. In certain instances, such an enhanced effect can be unexpectedly provided when the drops are administered as little as about 2 minutes apart, or less. In some instances, such benefits provided when the drops are administered so close together is advantageous because it can improve patient compliance with the protocol. For example, in some instances, patients that have to wait a longer time between drops may become distracted or bored and forget or otherwise fail to administer a second drop, resulting in sub-optimal results.

In some embodiments, provided herein is a method of treating presbyopia in an individual (e.g., in need thereof), the method comprising (e.g., topically) administering a first drop of an ophthalmological composition to an eye of the individual and subsequently administering a second drop of the ophthalmological composition to the eye of the individual. In specific embodiments, the ophthalmological composition comprises aceclidine or a salt thereof. In some embodiments, the second drop is administered to the eye of the individual about 5 minutes or less after the first drop is administered to the eye. In some embodiments, the second drop is administered to the eye of the individual about 2 minutes after the first drop is administered to the eye.

In certain embodiments, provided herein is a method of treating presbyopia in an individual (e.g., in need thereof), the method consisting essentially of (e.g., topically) administering a first drop of an ophthalmological composition to an eye of the individual and subsequently administering a second drop of the ophthalmological composition to the eye of the individual. In specific embodiments, the ophthalmological composition comprises aceclidine or a salt thereof. In some embodiments, the second drop is administered to the eye of the individual about 5 minutes or less after the first drop is administered to the eye. In some embodiments, the second drop is administered to the eye of the individual about 2 minutes after the first drop is administered to the eye.

In certain embodiments, provided herein is a method of treating presbyopia in an individual (e.g., in need thereof), the method comprising (e.g., topically) administering a first drop of an ophthalmological composition to an eye of the individual and subsequently administering a second drop of the ophthalmological composition to the eye of the individual. In specific embodiments, the ophthalmological composition comprises aceclidine or a salt thereof. In some embodiments, the second drop is administered to the eye of the individual about 5 minutes or less after the first drop is administered to the eye. In some embodiments, the second drop is administered to the eye of the individual about 2 minutes after the first drop is administered to the eye.

Provided in certain embodiments herein, is a method for treating presbyopia and improving distance vision in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye.

In some embodiments, the ophthalmological composition comprises aceclidine or a salt thereof in a concentration of about 1 wt. % to about 2 wt. %. In specific embodiments, the ophthalmological composition comprises aceclidine or a salt thereof in a concentration of about 1.75 wt. % (e.g., as determined based on the concentration of the aceclidine salt used in the formulation).

In some embodiments, the ophthalmological composition comprises aceclidine hydrochloride in a concentration of about 1.75 wt. %. In some embodiments, the ophthalmological composition comprises aceclidine in a concentration of about 1.44 wt. % based on the free base concentration of aceclidine.

In certain embodiments, following administration of the ophthalmological composition to the eye, the individual has 3-lines or more improvement in the eye (e.g., at 40 cm, such as determined using BCDVA). In some embodiments, following administration of the ophthalmological composition to the eye, the individual has 3-lines or more improvement in the eye within 0.5 hours of administering the second drop to the eye. In certain embodiments, following administration of the ophthalmological composition to the eye, the individual has 3-lines or more improvement for at least 8 hours in the eye. In specific embodiments, following administration of the ophthalmological composition to the eye, the individual has 3-lines or more improvement for at least 10 hours in the eye. In some embodiments, the method (and/or near vision improvement) is achieved without loss of 1 line or more (e.g., at 4 m).

In some embodiments, provided herein is a method of providing a pupil size of an eye of an individual to less than 2 millimeters (mm) in the eye of the individual for at least 9 hours, the method comprising administering an ophthalmological composition comprising a miotic agent (e.g., aceclidine) to an eye of the individual.

In some embodiments, a method provided herein comprises an individual administering (e.g., instilling) the first drop of a composition provided herein in each eye followed by the second drop in each eye two minutes later.

In certain embodiments, provided herein is a method for treating presbyopia, the method comprising instill one drop of an ophthalmological composition comprises aceclidine or a salt thereof in each eye followed by a second drop in each eye. In specific embodiments, the second drop is administered in each eye about two (2) minutes later (after the first drop in each eye). In some embodiments, a method provided herein provides an effect for up to at least 10 hours.

In some embodiments, provided herein is a method wherein a second ophthalmological composition is used in (administered to) the eye. In certain embodiments, the ophthalmological composition or the second ophthalmological composition is administered at least 5 minutes after the last dose of the other of the ophthalmological composition or the second ophthalmological composition, which was administered first.

In some embodiments, an ophthalmological composition provided herein does not comprise a cycloplegic agent. In some embodiments, an ophthalmological composition provided herein does not comprise tropicamide.

In some embodiments, an ophthalmological composition provided herein is (substantially) preservative-free (e.g., less than 0.2 wt. %, less than 0.1 wt. %, or 0 wt. %). In specific embodiments, the composition does not comprise a preservative.

In certain embodiments, no more than a first drop and a second drop of the ophthalmological composition is administered to an eye (e.g., in a day).

In some embodiments, an ophthalmological composition provided herein is administered to the eye (e.g., two drops, such as once daily) for at least 6 weeks. In some embodiments, an ophthalmological composition provided herein is administered to the eye (e.g., two drops, such as once daily) for at least 24 weeks.

In certain embodiments, an individual receiving the drops according to a method provided herein wears a contact lens, such as in the eye to which the drop(s) are administered. In some embodiments, the individual removes the contact lens before administering the ophthalmological composition to the eye. In certain embodiments, the individual inserts or reinserts the contact lens onto the eye at least about 10 minutes (e.g., at least about 15 minutes) after administering the second drop of the ophthalmological composition.

In certain embodiments, an ophthalmological composition provided herein is a pupil selective miotic composition.

In some embodiments, a composition provided herein comprises a miotic that is a pupil selective miotic. In specific embodiments, the pupil selective miotic is aceclidine or an ophthalmically acceptable salt thereof.

In some embodiments, provided herein is a method of reducing a corrective lens (e.g., bifocal or contact lens) wear time in an individual, the method comprising administering a composition comprising a miotic to an eye of the individual. In some embodiments, provided herein is a method of reducing a corrective lens (e.g., corrective glasses, such as bifocal, or contact lens) wear time in an individual, the method comprising administering a composition comprising a miotic to an eye of the individual.

In some embodiments, a lens is a bifocal glasses, progressive glasses, or a contact lens.

In certain embodiments, an individual treated according to a method provided herein is less dependent on wearing bifocals (e.g., glasses, progressive glasses, reading glasses), and/or contacts, such as during the workday. In certain embodiments, an individual treated according to a method provided herein is less dependent on wearing correctives glasses (e.g., bifocal glasses, progressive glasses, reading glasses), and/or contacts, such as during the workday.

In certain embodiments, an individual treated according to a method provided herein is, following treatment, less dependent on or no longer requires wearing a bifocal glasses, progressive glasses, reading glasses, or a contact lens to correct near vision. In certain embodiments, the bifocal glasses, progressive glasses, reading glasses, or contact lens corrects near vision by at least +0.75. In certain embodiments, the bifocal glasses, progressive glasses, reading glasses, or contact lens corrects near vision by at least +1.5. In certain embodiments, the bifocal glasses, progressive glasses, reading glasses, or contact lens corrects near vision by at least +2.0. In certain embodiments, the bifocal glasses, progressive glasses, reading glasses, or contact lens corrects near vision by at least +2.5. In certain embodiments, the bifocal glasses, progressive glasses, reading glasses, or contact lens corrects near vision by at least +3.0. In certain embodiments, the bifocal glasses, progressive glasses, reading glasses, or contact lens corrects near vision by at least +3.5.

In certain embodiments, an individual treated according to a method provided herein has moderate presbyopia. In certain embodiments, an individual treated according to a method provided herein has advanced presbyopia.

In certain embodiments, an individual treated according to a method provided herein has an improvement in near vision (e.g., at 40 cm) of at least 4 lines. In certain embodiments, the individual has an improvement in near vision (e.g., at 40 cm) of at least 5 lines. In certain embodiments, the individual has an improvement in near vision (e.g., at 40 cm) of at least 6 lines.

In certain embodiments, an individual treated according to a method provided herein has an improvement in distance vision (e.g., at 4 m) of at least 1 line.

In certain embodiments, an individual treated according to a method provided herein has an improvement in distance vision (e.g., at 4 m) of at least 3 letters.

In certain embodiments, an individual treated according to a method provided herein is at least 60 years old. In certain embodiments, the individual is 61-65 years old. In certain embodiments, the individual is 66-70 years old.

Provided in some embodiments herein are aceclidine compositions, such as aqueous aceclidine compositions having a pH of about 6 or less (e.g., about 4.5 or about 5.5), that have acceptable aceclidine stability profiles at room temperature (or higher temperatures) for extended periods of time. Additionally, in some embodiments, compositions described herein, such as aqueous aceclidine compositions described herein, have aceclidine stability profiles that are acceptable for manufacture, shipment, and/or (e.g., long-term and end-user) storage of aceclidine at room temperature (e.g., up to 25 degrees Celsius) (or higher temperatures). In certain instances, targeted pH of aceclidine compositions provided herein allowed for long term room temperature storage of compositions described herein, irrespective of whether or not other components were varied. For example, figures and examples provided herein demonstrate substantially similar storage stability for compositions, irrespective of presence or lack thereof of a preservative and/or irrespective of buffer concentration. In some instances, aceclidine stability of aceclidine compositions described herein, surprisingly, did not improve by changing certain parameters of the compositions, such as addition of a preservative and different buffer concentrations.

Provided herein are (e.g., aqueous) compositions that are stable at room temperature, retaining high (purity) levels (e.g., 90% or more, 95% or more, or even 98% or more) of aceclidine in the composition (e.g., compared to a baseline or an initial amount of aceclidine in the composition) at room temperature for extended periods of time, such as for up to 3 months. In some embodiments, provided herein are methods involving storing of a composition of up to 3 months or 6 months or the like. In certain embodiments, storage of a composition of up to x months, indicates that the composition is suitable for storage under the indicated conditions for any time period up to x months. For example, in some embodiments, when a composition is stored for up to x months according to a composition or method provided herein, the composition is suitable for subsequent use (e.g., having at least 90% initial aceclidine) at any point up to x months. In some instances, compositions described herein having a pH of about 6 or less, or less than 6 (e.g., a pH of about 4.5 to about 5.5) have substantially better aceclidine stability profiles than compositions described herein having a pH of greater than 6, or 6 or more. In some instances, a delineation exists between the stability of aceclidine compositions described herein having a pH of 6 or less (e.g., pH of about 4.5 to about 5.5) and equivalent compositions having a pH of 6 or more. In some instances, even changing other aceclidine composition parameters, such as buffer concentration or adding a preservative, has little or no effect on the stability of aceclidine in the compositions described herein, such as compositions having a pH of less than 6.

In some embodiments, compositions provided herein retain high (purity) levels (e.g., 90% or more, 95% or more, or even 98% or more) of aceclidine in the composition (e.g., compared to a baseline or an initial amount of aceclidine in the composition) at even higher temperatures (e.g., 40 degrees Celsius (° C.)) for extended periods of time, such as for up to 2 months. In some embodiments, compositions provided herein retain high (purity) levels (e.g., 90% or more, 95% or more, or even 98% or more) of aceclidine in the composition (e.g., compared to a baseline or an initial amount of aceclidine in the composition) during manufacture, shipment, and/or storage of the composition, such as at temperatures ranging from 0° C. to room temperature, or higher temperatures.

In some embodiments, a composition provided herein comprises aceclidine or a salt thereof and a pH of about 4.5 to about 5.5. In some embodiments, a composition provided herein comprises aceclidine or a salt thereof, a viscosity agent, and a pH of about 4.5 to about 5.5. In some embodiments, a composition provided herein comprises aceclidine or a salt thereof, a (nonionic) surfactant, and a pH of about 4.5 to about 5.5. In some embodiments, a composition provided herein comprises aceclidine or a salt thereof, a (nonionic) surfactant, a viscosity agent, and a pH of about 4.5 to about 5.5.

In some embodiments, a composition described herein has a room temperature when administered to the eye of an individual described herein. In some embodiments, a composition described herein has been stored at room temperature for up to 6 months prior to administration to an individual described herein. In some embodiments, a composition described herein has been stored up to 18 months before being stored at room temperature for up to 6 months prior to administration to an individual described herein.

In certain embodiments, provided herein is a method of treating presbyopia in an individual, the method comprising administering an ophthalmologically acceptable composition to an eye of the individual. In specific embodiments, the composition comprises aceclidine and has a pH of about 4.5 to about 5.5. In some embodiments, the composition has a room temperature (e.g., up to 25 degrees Celsius) when administered to the eye of the individual. In specific embodiments, a composition has a room temperature above 8 degrees Celsius and up to 25 degrees Celsius.

In some embodiments, provided herein is a method of treating presbyopia in an individual, the method comprising administering an ophthalmologically acceptable composition to an eye of the individual. In certain embodiments, the composition comprises aceclidine and has a pH of about 4.5 to about 5.5. In specific embodiments, the composition having been stored at room temperature (e.g., up to 25 degrees Celsius). In specific embodiments, the composition has been stored at room temperature for up to 3 months prior to administration. In some embodiments, the composition has been stored for up to 6 months prior to administration. In some embodiments, the composition has been stored at room temperature for 1 month prior to administration. In specific embodiments, the composition has been stored at room temperature for 2 months prior to administration. In specific embodiments, the composition has been stored at room temperature for 3 months prior to administration. In specific embodiments, a composition has a room temperature above 8 degrees Celsius and up to 25 degrees Celsius.

In certain embodiments, provided herein is a method of treating presbyopia in an individual, the method comprising administering an ophthalmologically acceptable composition to an eye of the individual. In some embodiments, the composition comprises aceclidine and a pH of about 4.5 to about 5.5. In certain embodiments, the composition has been stored at 2 degrees Celsius to 8 degrees Celsius up to 12-18 months (e.g., 6-18 month, or 12-18 months). In specific embodiments, the composition has been stored at 2 degrees Celsius to 8 degrees Celsius before being stored at room temperature. In specific embodiments, the composition has been stored at room temperature for up to 3 months prior to administration. In some embodiments, the composition has been stored for up to 6 months prior to administration. In some embodiments, the composition has been stored at room temperature for 1 month prior to administration. In specific embodiments, the composition has been stored at room temperature for 2 months prior to administration. In specific embodiments, the composition has been stored at room temperature for 3 months prior to administration. In specific embodiments, a composition has a room temperature above 8 degrees Celsius and up to 25 degrees Celsius.

In certain embodiments, provided herein is a method of treating presbyopia in an individual, the method comprising administering an ophthalmologically acceptable composition to an eye of the individual. In specific embodiments, the composition comprises aceclidine and a pH of about 4.5 to about 5.5. In some embodiments, the composition has been stored at greater than 25 degrees Celsius and up to 40 degrees Celsius for up to 8 days (e.g., 1-8 days) prior to administration.

In certain embodiments, a composition provided herein has a pH of about 4.5 to about 5. In some embodiments, a composition provided herein has a pH of about 5 to about 5.5.

In some embodiments, the composition has an initial amount of aceclidine (e.g., 100%), and wherein at least 90% of the initial amount of aceclidine is present in the composition when administering the composition to the eye of the individual (e.g., after the storage protocols provided herein).

In some embodiments, prior to administration, the composition has been stored for up to 6 months. In certain embodiments, prior to administration, the composition has been stored at a temperature of about 0 degrees Celsius to about 10 degrees Celsius. In specific embodiments, prior to administration, the composition has been stored at a temperature of about 2 degrees Celsius to about 8 degrees Celsius.

In some embodiments, prior to administration, the composition has been stored at a temperature up to about 40 degrees Celsius.

In certain embodiments, a composition provided herein comprises an aqueous medium.

In certain embodiments, a composition provided herein comprises a viscosity agent. In specific embodiments, the composition comprises a concentration of the viscosity agent of about 0.5 wt. % to about 5 wt. %. In more specific embodiments, the composition comprises a concentration of the viscosity agent of about 1 wt. % to about 1.5 wt. %.

In certain embodiments, a composition provided herein comprises a nonionic surfactant. In some embodiments, the composition comprises a concentration of the nonionic surfactant of about 2 wt. % to about 10 wt. %. In specific embodiments, the composition comprises a concentration of the nonionic surfactant of about 3 wt. % to about 5 wt. %.

In certain embodiments, a composition provided herein comprises a concentration of the aceclidine of about 0.2 wt. % to about 4 wt. %.

In certain embodiments, a composition provided herein comprises a concentration of the buffer of about 0.06 wt. % to about 0.1 wt. %.

In certain embodiments, a composition provided herein does not comprise a preservative.

In certain embodiments, a composition provided herein has been stored at a temperature from about 0 degrees Celsius to about 10 degrees Celsius, such as for up to 24 months. In certain embodiments, a composition provided herein has been stored at a temperature from about 2 degrees Celsius to about 8 degrees Celsius, such as for up to 24 months.

In certain embodiments, a composition provided herein has been stored at a temperature from about 0 degrees Celsius to about 10 degrees Celsius, such as for up to 12-18 months. In certain embodiments, a composition provided herein has been stored at a temperature from about 2 degrees Celsius to about 8 degrees Celsius, such as for up to 12-18 months.

In certain embodiments, a composition provided herein has been stored up to 24 months (e.g., at 2 degrees Celsius to 8 degrees Celsius). In certain embodiments, a composition provided herein comprises at least 90 wt. % of the initial amount (e.g., the amount of aceclidine in the composition prior to such storage) of aceclidine after storage for 24 months (e.g., at 2 degrees Celsius to 8 degrees Celsius). In certain embodiments, a composition provided herein comprises at least 95 wt. % of the initial amount (e.g., the amount of aceclidine in the composition prior to such storage) of aceclidine after storage for 24 months (e.g., at 2 degrees Celsius to 8 degrees Celsius).

In certain embodiments, a composition provided herein has been stored up to 18 months (e.g., at 2 degrees Celsius to 8 degrees Celsius). In certain embodiments, a composition provided herein comprises at least 90 wt. % of the initial amount (e.g., the amount of aceclidine in the composition prior to such storage) of aceclidine after storage for 18 months (e.g., at 2 degrees Celsius to 8 degrees Celsius). In certain embodiments, a composition provided herein comprises at least 95 wt. % of the initial amount (e.g., the amount of aceclidine in the composition prior to such storage) of aceclidine after storage for 18 months (e.g., at 2 degrees Celsius to 8 degrees Celsius).

In certain embodiments, a composition provided herein has been stored up to 12 months (e.g., at 2 degrees Celsius to 8 degrees Celsius). In certain embodiments, a composition provided herein comprises at least 90 wt. % of the initial amount (e.g., the amount of aceclidine in the composition prior to such storage) of aceclidine after storage for 12 months (e.g., at 2 degrees Celsius to 8 degrees Celsius). In certain embodiments, a composition provided herein comprises at least 95 wt. % of the initial amount (e.g., the amount of aceclidine in the composition prior to such storage) of aceclidine after storage for 12 months (e.g., at 2 degrees Celsius to 8 degrees Celsius).

In certain embodiments, a composition provided herein has been stored up to 6 months (e.g., at room temperature, such as up to 25 degrees Celsius). In certain embodiments, a composition provided herein comprises at least 90 wt. % of the initial amount (e.g., the amount of aceclidine in the composition prior to such storage) of aceclidine after storage for 6 months (e.g., at room temperature, such as up to 25 degrees Celsius). In certain embodiments, a composition provided herein comprises at least 95 wt. % of the initial amount (e.g., the amount of aceclidine in the composition prior to such storage) of aceclidine after storage for 6 months (e.g., at room temperature, such as up to 25 degrees Celsius).

In certain embodiments, a composition provided herein has been stored up to 3 months (e.g., at room temperature, such as up to 25 degrees Celsius). In certain embodiments, a composition provided herein comprises at least 90 wt. % of the initial amount (e.g., the amount of aceclidine in the composition prior to such storage) of aceclidine after storage for 3 months (e.g., at room temperature, such as up to 25 degrees Celsius). In certain embodiments, a composition provided herein comprises at least 95 wt. % of the initial amount (e.g., the amount of aceclidine in the composition prior to such storage) of aceclidine after storage for 3 months (e.g., at room temperature, such as up to 25 degrees Celsius).

In certain embodiments, a composition provided herein has been stored up to 2 weeks (e.g., at room temperature, such as up to 25 degrees Celsius). In certain embodiments, a composition provided herein comprises at least 90 wt. % of the initial amount (e.g., the amount of aceclidine in the composition prior to such storage) of aceclidine after storage for 2 weeks (e.g., at room temperature, such as up to 25 degrees Celsius). In certain embodiments, a composition provided herein comprises at least 95 wt. % of the initial amount (e.g., the amount of aceclidine in the composition prior to such storage) of aceclidine after storage for 2 weeks (e.g., at room temperature, such as up to 25 degrees Celsius).

Provided in some embodiments herein is a method of storing an ophthalmologically acceptable composition, the method comprising storing the composition for up to 6 months at room temperature, the composition comprising aceclidine and a pH of about 4.5 to about 5.5, wherein following the up to 6 months (e.g., 2-6 months) of storage at room temperature, the composition comprises at least 90% of the amount of aceclidine as prior to the up to 6 months (e.g., 1-6 months) of storage at room temperature.

Provided in some embodiments herein is a method of storing an ophthalmologically acceptable composition, the method comprising storing the composition for up to 12-18 months followed by storing the composition for up to 6 months (e.g., 2-6 months) at room temperature, the composition comprising aceclidine and a pH of about 4.5 to about 5.5, wherein following the up to 6 months of storage at room temperature, the composition comprises at least 90% of the amount of aceclidine as prior to the up to 6 months (e.g., 2-6 months) of storage at room temperature.

Provided in some embodiments herein is a method of storing an ophthalmologically acceptable composition, the method comprising storing the composition for up to 6 months at room temperature, the composition comprising aceclidine and a pH of about 4.5 to about 5.5, wherein following the up to 3 months (e.g., 2-3 months) of storage at room temperature, the composition comprises at least 90% of the amount of aceclidine as prior to the up to 3 months (e.g., 2-3 months) of storage at room temperature.

Provided in some embodiments herein is a method of storing an ophthalmologically acceptable composition, the method comprising storing the composition for up to 12-18 months followed by storing the composition for up to 3 months (e.g., 2-3 months) at room temperature, the composition comprising aceclidine and a pH of about 4.5 to about 5.5, wherein following the up to 6 months of storage at room temperature, the composition comprises at least 90% of the amount of aceclidine as prior to the up to 3 months (e.g., 2-3 months) of storage at room temperature.

In some embodiments, a method provided herein comprises storing the composition at a temperature from about 0 degrees Celsius to about 10 degrees Celsius (e.g., 2-8C), such as for up to 12-18 months (e.g., for 12-18 months). In some embodiments, a method provided herein comprises storing the composition for up to 18 months (e.g., 12-18 months).

In some embodiments, a method provided herein comprises storing the composition for up to 12 months (e.g., 6-12 months).

In some embodiments, a method provided herein comprises storing the composition for up to 6 months (e.g., 3-6 months).

Provided in certain embodiments herein is a composition for use in treating presbyopia in an individual, the composition comprising aceclidine and a pH of about 4.5 to about 5.5, and the composition having a room temperature when administered to an eye of the individual.

Provided in certain embodiments herein is a composition for use in treating presbyopia in an individual, the composition comprising aceclidine and a pH of about 4.5 to about 5.5, and having been stored at room temperature for up to 6 months prior to administering to an eye of the individual.

Provided in certain embodiments herein is a composition for use in treating presbyopia in an individual, the composition comprising aceclidine and a pH of about 4.5 to about 5.5, and having been stored up to 12-18 months before being stored at room temperature, and having been stored at room temperature for up to 6 months prior to administering to an eye of the individual.

Provided in certain embodiments herein is a composition for use in treating presbyopia in an individual, the composition comprising aceclidine and a pH of about 4.5 to about 5.5, and having been stored at room temperature for up to 3 months (e.g., 2-3 months) prior to administering to an eye of the individual.

Provided in certain embodiments herein is a composition for use in treating presbyopia in an individual, the composition comprising aceclidine and a pH of about 4.5 to about 5.5, and having been stored up to 12-18 months (e.g., for 12-18 months) before being stored at room temperature, and having been stored at room temperature for up to 3 months (e.g., 2-3 months) prior to administering to an eye of the individual.

In some embodiments, provided herein is a composition having a pH of about 4.5 to about 5. In some embodiments, provided herein is a composition having a pH of about 5 to about 5.5.

In some embodiments, provided herein is a composition that has an initial amount of aceclidine (e.g., 100%), and wherein at least 90% of the initial amount of aceclidine being present in the composition upon administration of the composition to the eye of the individual.

In some embodiments, prior to administration, a composition provided herein has been stored for up to 6 months. In some embodiments, prior to administration, a composition provided herein has been stored for up to 3 months (e.g., 2-3 months), such as at room temperature.

In some embodiments, prior to administration, a composition provided herein has been stored at a temperature of about 0 degrees Celsius to about 10 degrees Celsius. In some embodiments, prior to administration, a composition provided herein has been stored at a temperature of about 2 degrees Celsius to about 8 degrees Celsius. In specific embodiments, the composition has been stored at such a temperature for up to 18 months (e.g., for 12-18 months).

In some embodiments, prior to administration, a composition provided herein has been stored at a temperature up to about 40 degrees Celsius.

In some embodiments, a composition provided herein comprises an aqueous medium.

In some embodiments, a composition provided herein comprises a viscosity agent. In specific embodiments, the composition comprises a concentration of the viscosity agent of about 0.5 wt. % to about 5 wt. %. In more specific embodiments, the composition comprises a concentration of the viscosity agent of about 1 wt. % to about 1.5 wt. %.

In some embodiments, a composition provided herein comprises a nonionic surfactant. In specific embodiments, the composition comprises a concentration of the nonionic surfactant of about 2 wt. % to about 10 wt. %. In still more specific embodiments, the composition comprises a concentration of the nonionic surfactant of about 3 wt. % to about 5 wt. %.

In some embodiments, a composition provided herein comprises a concentration of the aceclidine of about 0.2 wt. % to about 4 wt. %.

In some embodiments, a composition provided herein comprises a concentration of the buffer of about 0.06 wt. % to about 0.1 wt. %.

In some embodiments, a composition provided herein does not comprise a preservative.

In some embodiments, a composition provided herein has been stored at a temperature of about 0 degrees Celsius to about 10 degrees Celsius for up to 12-18 months. In some embodiments, a composition provided herein has been stored up to 18 months (e.g., for 12-18 months). In some embodiments, the composition has been stored up to 12 months. In certain embodiments, the composition has been stored up to 6 months.

Provided in certain embodiments herein is a method of treating presbyopia in an individual, the method comprising administering the ophthalmologically acceptable composition to an eye of the individual, the composition comprising: aceclidine or a salt thereof at a concentration of about 1 weight percent (wt. %) to about 2 wt. %; and a pH of 4.5 to 5.5, the composition having been stored at room temperature, up to 25 degrees Celsius, for up to 3 months (e.g., for 2-3 months) prior to administration.

Provided in some embodiments therein is a method of treating presbyopia in an individual, the method comprising (i) storing an ophthalmologically acceptable composition, and (ii) administering the ophthalmologically acceptable composition to an eye of the individual, the composition comprising: aceclidine or a salt thereof at a concentration of about 1 weight percent (wt. %) to about 2 wt. %; and a pH of 4.5 to 5.5, the composition having been stored at room temperature, up to 25 degrees Celsius, for up to 3 months (e.g., 2-3 months) prior to administration.

In some embodiments, the composition has been stored at room temperature for up to 6 months prior to administration.

In certain embodiments, the composition has been stored at room temperature for 1 month prior to administration. In some embodiments, the composition has been stored at room temperature for 2 months prior to administration. In some embodiments, the composition has been stored at room temperature for 3 months prior to administration.

In some embodiments, a composition provided herein has a pH of about 5 to 5.5.

In certain embodiments, a composition provided herein has an initial amount of aceclidine and at least 90% of the initial amount of aceclidine is present in the composition when the composition is administered to the eye of the individual.

In some embodiments, prior to administration, a composition provided herein has been stored at a temperature of 2 degrees Celsius to 8 degrees Celsius. In certain embodiments, prior to administration, the composition has been stored at a temperature of 2 degrees Celsius to 8 degrees Celsius for 12 months. In certain embodiments, prior to administration, the composition has been stored at a temperature of 2 degrees Celsius to 8 degrees Celsius for 18 months.

In certain embodiments, prior to administration, the composition has been stored at a temperature of greater than 25 degrees Celsius and up to 40 degrees Celsius. In certain embodiments, prior to administration, the composition has been stored at a temperature of greater than 25 degrees Celsius and up to 40 degrees Celsius for up to 8 days (e.g., for 1-8 days).

In some embodiments, a composition provided herein comprises a viscosity agent.

In some embodiments, a composition provided herein comprises a nonionic surfactant.

Provided in certain embodiments herein, is a method for treating presbyopia in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye. In some embodiments, the ophthalmological composition is as described herein, such as having been stored as described herein.

Provided in certain embodiments herein, is a method for treating presbyopia and improving distance vision in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye. In some embodiments, the ophthalmological composition is as described herein, such as having been stored as described herein.

In certain embodiments, an individual treated according to a method provided herein has moderate presbyopia. In certain embodiments, an individual treated according to a method provided herein has advanced presbyopia.

In certain embodiments, an individual treated according to a method provided herein has an improvement in near vision (e.g., at 40 cm) of at least 4 lines. In certain embodiments, the individual has an improvement in near vision (e.g., at 40 cm) of at least 5 lines. In certain embodiments, the individual has an improvement in near vision (e.g., at 40 cm) of at least 6 lines.

In certain embodiments, an individual treated according to a method provided herein has an improvement in distance vision (e.g., at 4 m) of at least 1 line.

In certain embodiments, an individual treated according to a method provided herein has an improvement in distance vision (e.g., at 4 m) of at least 3 letters.

In certain embodiments, an individual treated according to a method provided herein is at least 60 years old. In certain embodiments, the individual is 61-65 years old. In certain embodiments, the individual is 66-70 years old Provided in certain embodiments herein are systems, compositions, and methods, such as for treating ocular disorders, such as presbyopia. In some embodiments, provided herein is a method of improving vision. In some embodiments, provided herein is a method of improving near vision. In some embodiments, provided herein is a method of improving distance vision. In some embodiments, provided herein is a method of treating presbyopia. In some embodiments, a composition provided herein comprises a composition comprising a miotic (e.g., aceclidine or a salt thereof).

In some embodiments, a system provided herein comprises such a composition (e.g., and a vessel containing the composition). In some embodiments, a method provided herein comprises administering such a composition, such as to an eye (e.g., surface) of an individual.

Provided in some embodiments herein is a method of treating presbyopia in an individual (e.g., in need thereof). In certain embodiments provided herein is a method of treating presbyopia in an individual, the method comprising administering an ophthalmological composition to an eye (e.g., an ocular surface thereof) of the individual.

In some embodiments, a method provided herein comprises (e.g., topically) administering a first drop of an ophthalmological composition to an eye (e.g., an ocular surface thereof) of an individual and subsequently administering a second drop of the ophthalmological composition to the eye (e.g., an ocular surface thereof) of the individual. In some embodiments, a composition provided herein comprises a composition comprising a miotic (e.g., aceclidine or a salt thereof).

In certain embodiments, provided herein is a system comprising a single use container and a (e.g., ophthalmological) composition comprising aceclidine or a salt thereof. In some instances, systems provided herein facilitate the use of a dissolved aceclidine that has good stability, including at extended storage times (e.g., including under refrigerated and room temperature storage conditions).

Aceclidine, which is an approved therapy for glaucoma, provides meaningful therapeutic effects in presbyopic individuals. For example, administering certain aceclidine compositions to the eyes of presbyopic individuals provides beneficial effects, such as improvements to near-sighted vision without affecting baseline distance vision. However, aceclidine is susceptible to degradation, particularly when in solution, so formulating aceclidine in aqueous environments, such as in the form of an eye drop, is challenging. To avoid aceclidine degradation and problems associated with such degradation (e.g., decreased efficacy), aceclidine has typically been stored in a two-bottle system comprising lyophilized aceclidine, which is reconstituted before topical installation to the eye. Certain cold-chain storage protocols have been found to substantially improve the stability profiles of certain aceclidine compositions, such as at temperatures suitable for refrigeration. However, maintaining aceclidine stability at room temperature for prolonged periods of time, such as for more than a few months, has remained a challenge. In addition, requiring end users to store aceclidine compositions at cold temperatures can be a challenge, leading to storage at temperatures not suitable for retaining efficacy for the intended uses of aceclidine products. As such, the instability of aceclidine in aqueous environments poses a challenge for preparing, shipping, and storing aqueous aceclidine compositions.

Provided in some embodiments herein are compositions and systems, that have acceptable aceclidine stability profiles at room temperature (or higher temperatures) for extended periods of time, even when filled and loaded into a container under non-inert conditions, such as under an oxygen containing gas, e.g., air. Additionally, in some embodiments, compositions described herein and systems provided herein comprising such compositions, such as aqueous aceclidine compositions described herein, have aceclidine stability profiles that are acceptable for manufacture, shipment, and/or (e.g., long-term and end-user) storage of aceclidine at room temperature (e.g., up to 25 degrees Celsius) (or higher temperatures). In certain instances, systems and compositions provided herein allowed for long term room temperature storage of compositions described herein, irrespective of whether or not other components were varied.

Provided herein are (e.g., aqueous) compositions (e.g., in a system provided herein) that are stable at room temperature, retaining high (purity) levels (e.g., 90% or more, 95% or more, or even 98% or more) of aceclidine in the composition (e.g., compared to a baseline or an initial amount of aceclidine in the composition) at room temperature for extended periods of time, such as for up to 3 months. In some embodiments, provided herein are methods involving storing of a composition for up to 3 months or 6 months or the like. In certain embodiments, storage of a composition for up to x months (e.g., 3 months), indicates that the composition is suitable for storage under the indicated conditions for any time period up to x months (e.g., 3 months). For example, in some embodiments, when a composition is stored for up to x months according to a composition or method provided herein, the composition is suitable for subsequent use (e.g., having at least 90% initial aceclidine) at any point up to x months.

Provided herein are (e.g., aqueous) compositions (e.g., in a system provided herein) that are stable (e.g., under specified conditions, such as at room temperature). In some embodiments, stable compositions retain high (purity) levels (e.g., 90% or more, 95% or more, or even 98% or more) of aceclidine in the composition (e.g., compared to a baseline or an initial amount of aceclidine in the composition) (e.g., under specified conditions, such as at room temperature). In some embodiments, composition provided herein is stable (e.g., under specified conditions, such as at room temperature), for extended periods of time, such as for up to 3 months or more. In some embodiments, a stable composition that is stable for up to a specified duration of time (x), the stable composition is stable for any amount of time, up to the specified duration of time, inclusive of the terminal time point. For example, a stable composition that is stable for up to 3 months is stable for 1 week, 1 month, 2 months, and 3 months, provided that it has not already been used prior to the specified time point. In other words, in some instances (e.g., wherein the stability is inclusive of the terminal time point), if a stable composition that is stable for up to 3 months is used after 3 months, it was stable for the entirety of the 3 months. However, if that same composition was used at the 2 months, it was stable for the entirety of the 2 months and would have been stable for the entirety of the 3 months, if it had not been used at the 2 months. As used herein, any disclosure of a composition having a stability of up to a specified time point, includes a disclosure of the composition having a stability of up to a specified time point, inclusive of that time point (e.g., assuming that it had not been previously used).

In some embodiments, compositions provided herein retain high (purity) levels (e.g., 90% or more, 95% or more, or even 98% or more) of aceclidine in the composition (e.g., compared to a baseline or an initial amount of aceclidine in the composition) at even higher temperatures (e.g., 40 degrees Celsius (° C.)) for extended periods of time, such as for up to 2 months. In some embodiments, compositions provided herein retain high (purity) levels (e.g., 90% or more, 95% or more, or even 98% or more) of aceclidine in the composition (e.g., compared to a baseline or an initial amount of aceclidine in the composition) during manufacture, shipment, and/or storage of the composition, such as at temperatures ranging from 0° C. to room temperature, or higher temperatures.

In some embodiments, provided herein is a system comprising a single-patient-use container and an ophthalmological composition. In specific embodiments, the ophthalmological composition comprises aceclidine or a salt thereof. In some embodiments, the single-patient-use container comprises an enclosed chamber. In specific embodiments, the ophthalmological composition is configured within the enclosed chamber of the single patient-use-container. In some embodiments, the single-patient-use container is configured to be irreversibly opened, and single-patient-use container being configured, when open, to dispense a first drop and a second drop of the ophthalmological composition through an opening (e.g., an opening formed upon irreversibly opening of the container).

In some embodiments, a single-patient-use container provided herein is a vial or an ampoule. In some embodiments, single-patient-use container is a vial (e.g., plastic vial).

In certain embodiments, the single-patient-use container comprises a container body, a container neck, and a container head, the container body and the container head having a larger cross-sectional dimension than the container neck, the enclosed chamber extending from the container body into the container neck, and the single-patient-use container being configured to be opened at the container neck.

In some embodiments, a single-patient-use container provided herein (e.g., prior to opening) is sterile. In specific embodiments, the enclosed chamber of the container is sterile.

In some embodiments, a single-patient-use container provided herein is transparent.

In certain embodiments, a single-patient-use container provided herein comprises polyethylene. In specific embodiments, the container comprises a low-density polyethylene (LDPE).

In some embodiments, a system provided herein comprises about 0.2 mL to about 2 mL of the ophthalmological composition. In specific embodiments, the system comprises about 0.2 mL to about 1 ml of the ophthalmological composition. In more specific embodiments, the system comprises about 0.5 mL of the ophthalmological composition.

In certain embodiments, an ophthalmological composition provided herein comprises aceclidine or a salt thereof in a concentration of about 1 wt. % to about 2 wt. %. In specific embodiments, the ophthalmological composition comprises aceclidine or a salt thereof in a concentration of about 1.75 wt. % (e.g., based on the weight of a salt form of aceclidine formulated into the composition).

In some embodiments, the ophthalmological composition comprises aceclidine hydrochloride in a concentration of about 1.75 wt. %. In some embodiments, the ophthalmological composition comprises aceclidine in a concentration of about 1.44 wt. % based on the free base concentration of aceclidine.

In some embodiments, a system provided herein comprises a package and at least 3 identical containers and at least 3 identical ophthalmological compositions.

Provided in certain embodiments herein, is a method for treating presbyopia in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye.

Provided in certain embodiments herein, is a method for treating presbyopia and improving distance vision in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye.

In some embodiments, a method provided herein comprises administering to a second eye of the individual a third drop and a fourth drop of an ophthalmological composition to the second eye of the individual. In some embodiments, the fourth drop is administered to the eye of the individual about 5 minutes or less after the third drop is administered to the eye. In some embodiments, the fourth drop is administered to the eye of the individual about 2 minutes after the third drop is administered to the eye. In some embodiments, third drop is administered to the second eye prior to the second drop being administered to the first eye.

In certain embodiments, provided herein is a method comprising opening a second single-patient-use container on a second day and subsequently administering to the first eye of the individual a second container first drop and a second container second drop of a second container ophthalmological composition. In some embodiments, the second container ophthalmological composition provided herein (e.g., comprising a miotic, such as aceclidine or a salt thereof). In specific embodiments, the first and second days are different days. In some embodiments, the second drop is administered to the eye of the individual about 5 minutes or less after the first drop is administered to the eye. In some embodiments, the second drop is administered to the eye of the individual about 2 minutes after the first drop is administered to the eye.

In specific embodiments, the ophthalmological composition and the second container ophthalmological composition are identical.

In some embodiments, any system provided herein comprises a container provided herein, with a composition provided herein and a gas within the chamber thereof. In certain embodiments, the gas within the chamber need not be an inert gas. In some instances, a composition of a system provided herein is stable (e.g., good stability of aceclidine, such as provided herein), including at room temperature, even without the need for an inert gas.

In some embodiments, a system provided herein comprises a container provided herein, with a composition provided herein and an oxygen containing gas within the chamber thereof. In specific embodiments, the oxygen containing gas is air (e.g., sterile air).

In certain instances, previously unreported extended effect of two drop doses achievable with a limited amount of time between drops allows for the use a (e.g., sterile and preservative free) composition with a single use container. In some instances, longer delay between drops may require multiple containers for a single dose because long duration between drop administration may be problematic with an aceclidine solution, particularly one that is preservative free.

In some instances, compositions described herein having a pH of about 6 or less, or less than 6 (e.g., a pH of about 4.5 to about 5.5) have substantially better aceclidine stability profiles than compositions described herein having a pH of greater than 6, or 6 or more. In some instances, a delineation exists between the stability of aceclidine compositions described herein having a pH of 6 or less (e.g., pH of about 4.5 to about 5.5) and equivalent compositions having a pH of 6 or more. In some instances, even changing other aceclidine composition parameters, such as buffer concentration or adding a preservative, has little or no effect on the stability of aceclidine in the compositions described herein, such as compositions having a pH of less than 6.

In some embodiments, a composition provided herein comprises aceclidine or a salt thereof and a pH of about 4.5 to about 5.5. In some embodiments, a composition provided herein comprises aceclidine or a salt thereof, a viscosity agent, and a pH of about 4.5 to about 5.5. In some embodiments, a composition provided herein comprises aceclidine or a salt thereof, a (nonionic) surfactant, and a pH of about 4.5 to about 5.5. In some embodiments, a composition provided herein comprises aceclidine or a salt thereof, a (nonionic) surfactant, a viscosity agent, and a pH of about 4.5 to about 5.5.

In certain embodiments, an individual treated according to a method provided herein has moderate presbyopia. In certain embodiments, an individual treated according to a method provided herein has advanced presbyopia.

In certain embodiments, an individual treated according to a method provided herein has an improvement in near vision (e.g., at 40 cm) of at least 4 lines. In certain embodiments, the individual has an improvement in near vision (e.g., at 40 cm) of at least 5 lines. In certain embodiments, the individual has an improvement in near vision (e.g., at 40 cm) of at least 6 lines.

In certain embodiments, an individual treated according to a method provided herein has an improvement in distance vision (e.g., at 4 m) of at least 1 line.

In certain embodiments, an individual treated according to a method provided herein has an improvement in distance vision (e.g., at 4 m) of at least 3 letters.

In certain embodiments, an individual treated according to a method provided herein is at least 60 years old. In certain embodiments, the individual is 61-65 years old. In certain embodiments, the individual is 66-70 years old.

In some embodiments, a method provided herein comprises (e.g., topically) administering a first drop of an ophthalmological composition to an eye (e.g., an ocular surface thereof) of an individual and subsequently administering a second drop of the ophthalmological composition to the eye (e.g., an ocular surface thereof) of the individual.

In some embodiments, a composition provided herein comprises a composition comprising a miotic (e.g., aceclidine or a salt thereof).

Provided in certain embodiments herein is a method of treating presbyopia in an individual, the method comprising administering an ophthalmological composition to an eye of the individual. In specific embodiments, the ophthalmological composition comprises a miotic. In still more specific embodiments, the treated eye of the individual previously underwent ocular surgery.

Provided in certain embodiments herein is a method of treating presbyopia in an individual, the method comprising administering an ophthalmological composition to an eye of the individual, the ophthalmological composition comprising aceclidine or a salt thereof.

Provided in certain embodiments herein, is a method for treating presbyopia and improving distance vision in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye.

In some embodiments, the treated eye of the individual previously underwent ocular surgery. In some embodiments, an individual treated with a method provided herein previously underwent post-refractive surgery. In some embodiments, an individual treated with a method provided herein previously underwent laser assisted in situ keratomileusis (LASIK) surgery. In some embodiments, an individual treated with a method provided herein previously underwent photorefractive keratectomy (PRK) surgery. In some embodiments, the individual is a pseudophakia individual.

In certain embodiments, the ophthalmological composition is a pupil selective miotic composition. In some embodiments, the miotic is a pupil selective miotic. In certain embodiments, the pupil selective miotic is aceclidine or an ophthalmically acceptable salt thereof.

In some embodiments, prior to surgery the individual wore a corrective contact lens or corrective glasses (e.g., bifocals), and after surgery and administration of the ophthalmological composition, the individual does not need to (or does not) wear the corrective contact lens or corrective glasses (e.g., bifocals).

In some embodiments, following administration of the ophthalmological composition to the eye, the individual has 3-lines or more improvement in the eye (e.g., at 40 cm, by BCDVA). In certain embodiments, following administration of the ophthalmological composition to the eye, the individual has 3-lines or more improvement in the eye within 0.5 hours of administering the second drop to the eye (e.g., at 40 cm, by BCDVA). In some embodiments, following administration of the ophthalmological composition to the eye, the individual has 3-lines or more improvement for at least 8 hours in the eye (e.g., at 40 cm, by BCDVA). In specific embodiments, following administration of the ophthalmological composition to the eye, the individual has 3-lines or more improvement for at least 10 hours in the eye (e.g., at 40 cm, by BCDVA).

In some embodiments, following administration of the ophthalmological composition to the eye, the pupil size of the eye is about 1.5 mm to about 2 mm. In specific embodiments, following administration of the ophthalmological composition to the eye, the pupil size of the eye is about 1.5 mm to about 2 mm within 0.5 hours of administering the second drop to the eye. In certain embodiments, following administration of the ophthalmological composition to the eye, the pupil size of the eye is about 1.5 mm to about 2 mm for at least 8 hours. In specific embodiments, following administration of the ophthalmological composition to the eye, the pupil size of the eye is about 1.5 mm to about 2 mm for about 10 hours or more. In some embodiments, following administration of the ophthalmological composition to the eye, the pupil size of the eye is about 1.5 mm to about 2 mm for at least 8 hours and no more than about 2.1 mm for at least 10 hours.

In certain embodiments, the reduction in pupil size is maintained in low light conditions.

In some embodiments, the reduction in pupil size is maintained for an entire workday (e.g., over a period of about 8 hours).

In certain embodiments, a miotic provided herein is aceclidine or a salt thereof. In some embodiments, an ophthalmological composition provided herein comprises a miotic, such as aceclidine or a salt thereof, at a concentration of about 1.2 wt. % to about 1.8 wt. %. In specific embodiments, the ophthalmological composition comprises aceclidine in a free base concentration of about 1.4 wt. % to about 1.5 wt. %. In some embodiments, the ophthalmological composition is formulated with about 1.7 wt. % to about 1.8 wt. % aceclidine hydrochloride.

In some embodiments, an ophthalmological composition provided herein does not comprise a cycloplegic. In some embodiments, an ophthalmological composition provided herein does not comprise tropicamide.

In certain embodiments, an ophthalmological composition is (substantially) preservative-free (e.g., less than 0.2 wt. %, less than 0.1 wt. %, or 0 wt. %). In specific embodiments, the composition does not comprise a preservative.

In some embodiments, an ophthalmological composition provided herein is clear and colorless.

In some embodiments, an ophthalmological composition provided herein ophthalmological composition is sterile.

In some embodiments, an ophthalmological composition provided herein is aqueous.

In some embodiments, an ophthalmological composition provided herein comprises a thickening agent. In specific embodiments, the thickening agent is hydroxypropyl methylcellulose. In some embodiments, the thickening agent is present in the ophthalmological composition in a concentration of about 1 wt. % to about 1.5 wt. % (e.g., about 1.25 wt. %).

In some embodiments, an ophthalmological composition provided herein comprises a tonicity agent. In specific embodiments, the tonicity agent is mannitol. In some embodiments, a tonicity agent is present in the ophthalmological composition in a concentration of about 2 wt. % to about 3 wt. % (e.g., about 2.5 wt. %).

In some embodiments, an ophthalmological composition provided herein comprises a lubricant. In specific embodiments, the lubricant is polysorbate 80. In some embodiments, the lubricant is present in the ophthalmological composition in a concentration of about 3 wt. % to about 5 wt. % (e.g., about 4 wt. %).

In some embodiments, an ophthalmological composition provided herein comprises a chelating agent. In specific embodiments, the chelating agent is edetate (e.g., formulated with edetate disodium dihydrate). In some embodiments, the chelating agent is present or formulated into the ophthalmological composition in a concentration of about 0.05 wt. % to about 0.2 wt. % (e.g., formulated with edetate disodium dihydrate at a concentration of about 0.1 wt. %).

In some embodiments, an ophthalmological composition provided herein comprises a buffering agent. In specific embodiments, the buffering agent is citrate (e.g., formulated with sodium citrate). In some embodiments, the buffering agent is present or formulated into the ophthalmological composition in a concentration of about 0.05 wt. % to about 0.15 wt. % (e.g., formulated with sodium citrate at a concentration of about 0.08 wt. %).

In some embodiments, an ophthalmological composition provided herein has a pH of about 4.5 to about 5.5.

In some embodiments, an ophthalmological composition provided herein is stored at room temperature (e.g., up to 25° C.) (e.g., up to 3 months or up to 6 months) prior to administration. In some embodiments, an ophthalmological composition provided herein is stored at 2° C. to 8° C. (e.g., up to 12 months or up to 18 months) prior to administration. In certain embodiments, an ophthalmological composition provided herein is stored at 2° C. to 8° C. up to 12 months prior to administration. In certain embodiments, an ophthalmological composition provided herein is stored at 2° C. to 8° C. up to 18 months prior to administration. In certain embodiments, an ophthalmological composition provided herein is stored at 2° C. to 8° C. up to 24 months prior to administration.

In certain embodiments, an ophthalmological composition provided herein comprises at least 95 wt. % of the aceclidine present in the composition prior to storage after the composition is stored at 2° C. to 8° C. up to 12 months. In certain embodiments, an ophthalmological composition provided herein comprises at least 95 wt. % of the aceclidine present in the composition prior to storage after the composition is stored at 2° C. to 8° C. up to 18 months. In certain embodiments, an ophthalmological composition provided herein comprises at least 95 wt. % of the aceclidine present in the composition prior to storage after the composition is stored at 2° C. to 8° C. up to 24 months.

In some embodiments, an ophthalmological composition provided herein is stored at a temperature up to 40° C. (e.g., up to 8 days) prior to administration.

In some embodiments, an ophthalmological composition provided herein is an eye drop (e.g., slightly viscous ophthalmic solution).

In certain embodiments, two drops of the ophthalmological composition are administered to the eye (e.g., wherein the two drops are administered about two minutes apart).

In certain embodiments, an individual treated according to a method provided herein is, following treatment, less dependent on or no longer requires wearing a bifocal glasses, progressive glasses, reading glasses, or a contact lens to correct near vision. In certain embodiments, the bifocal glasses, progressive glasses, reading glasses, or contact lens corrects near vision by at least +0.75. In certain embodiments, the bifocal glasses, progressive glasses, reading glasses, or contact lens corrects near vision by at least +1.5. In certain embodiments, the bifocal glasses, progressive glasses, reading glasses, or contact lens corrects near vision by at least +2.0. In certain embodiments, the bifocal glasses, progressive glasses, reading glasses, or contact lens corrects near vision by at least +2.5. In certain embodiments, the bifocal glasses, progressive glasses, reading glasses, or contact lens corrects near vision by at least +3.0. In certain embodiments, the bifocal glasses, progressive glasses, reading glasses, or contact lens corrects near vision by at least +3.5.

In certain embodiments, an individual treated according to a method provided herein has moderate presbyopia. In certain embodiments, an individual treated according to a method provided herein has advanced presbyopia.

In certain embodiments, an individual treated according to a method provided herein has an improvement in near vision (e.g., at 40 cm) of at least 4 lines. In certain embodiments, the individual has an improvement in near vision (e.g., at 40 cm) of at least 5 lines. In certain embodiments, the individual has an improvement in near vision (e.g., at 40 cm) of at least 6 lines.

In certain embodiments, an individual treated according to a method provided herein has an improvement in distance vision (e.g., at 4 m) of at least 1 line.

In certain embodiments, an individual treated according to a method provided herein has an improvement in distance vision (e.g., at 4 m) of at least 3 letters.

In certain embodiments, an individual treated according to a method provided herein is at least 60 years old. In certain embodiments, the individual is 61-65 years old. In certain embodiments, the individual is 66-70 years old.

Provided in certain embodiments herein are systems, compositions, and methods, such as for improving ocular function, such as reducing contact lens wear time and/or treating presbyopia. In specific embodiments, provided herein are systems, compositions, and methods for reducing contact lens wear time.

In some embodiments, provided herein is a method of treating presbyopia in an individual wearing a contact lens. In certain embodiments, the method comprises administering (e.g., topically) one or more drop of an ophthalmological composition comprising aceclidine to an eye of the individual described herein. In specific embodiments, the method comprises removing the contact lens from the eye before administering the ophthalmological composition to the eye. In more specific embodiments, the method comprises reinserting the contact lens onto the eye (e.g., about 10 minutes or more) after administering (e.g., dosing) the ophthalmological composition.

Provided in certain embodiments herein are systems, compositions, and methods, such as for treating ocular disorders, such as presbyopia. In some embodiments, provided herein is a method of improving vision. In some embodiments, provided herein is a method of improving near vision. In some embodiments, provided herein is a method of improving distance vision. In some embodiments, provided herein is a method of treating presbyopia. In some embodiments, a composition provided herein comprises a composition comprising a miotic (e.g., aceclidine or a salt thereof). In some embodiments, a system provided herein comprises such a composition (e.g., and a vessel containing the composition). In some embodiments, a method provided herein comprises administering such a composition, such as to an eye (e.g., surface) of an individual.

Provided in some embodiments herein is a method of treating presbyopia in an individual (e.g., in need thereof). In certain embodiments provided herein is a method of treating presbyopia in an individual, the method comprising administering an ophthalmological composition to an eye (e.g., an ocular surface thereof) of the individual.

Provided in some embodiments herein is a method of treating presbyopia with a concomitant improvement in myopia in an individual (e.g., in need thereof). In certain embodiments provided herein is a method of treating presbyopia with a concomitant improvement in myopia in an individual, the method comprising administering an ophthalmological composition to an eye (e.g., an ocular surface thereof) of the individual.

Provided in some embodiments herein is a method of treating presbyopia with a concomitant improvement in distance vision in an individual (e.g., in need thereof). In certain embodiments provided herein is a method of treating presbyopia with a concomitant improvement in distance vision in an individual, the method comprising administering an ophthalmological composition to an eye (e.g., an ocular surface thereof) of the individual.

In some embodiments, a method provided herein comprises (e.g., topically) administering a first drop of an ophthalmological composition to an eye (e.g., an ocular surface thereof) of an individual and subsequently administering a second drop of the ophthalmological composition to the eye (e.g., an ocular surface thereof) of the individual. In some embodiments, a composition provided herein comprises a composition comprising a miotic (e.g., aceclidine or a salt thereof).

Provided in certain embodiments herein, is a method of treating presbyopia in an individual wearing a contact lens, the method comprising: administering (e.g., topically) one or more drop of an ophthalmological composition comprising aceclidine to an eye of the individual; removing the contact lens from the eye before administering the ophthalmological composition to the eye; and reinserting the contact lens onto the eye about 10 minutes or more after administering (e.g., dosing) the ophthalmological composition.

Provided in certain embodiments herein, is a method for treating presbyopia in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye.

Provided in certain embodiments herein, is a method for treating presbyopia and improving distance vision in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye.

In some embodiments, provided herein is a method of reducing a corrective lens (e.g., bifocal or contact lens) wear time in an individual, the method comprising administering a composition comprising a miotic to an eye of the individual. In some embodiments, provided herein is a method of reducing a corrective lens (e.g., corrective glasses, such as bifocal, or contact lens) wear time in an individual, the method comprising administering a composition comprising a miotic to an eye of the individual.

In some embodiments, a lens is a bifocal glasses, progressive glasses, or a contact lens.

In certain embodiments, an individual treated according to a method provided herein is less dependent on wearing bifocals (e.g., glasses, progressive glasses, reading glasses), and/or contacts, such as during the workday. In certain embodiments, an individual treated according to a method provided herein is less dependent on wearing correctives glasses (e.g., bifocal glasses, progressive glasses, reading glasses), and/or contacts, such as during the workday.

In some embodiments, an individual treated according to a method provided herein no longer requires wearing a bifocal glasses, progressive glasses, reading glasses, or a contact lens (e.g., to correct vision). In certain embodiments, an individual treated according to a method provided herein prior to administration regularly wears corrective lens or at least half a day (e.g., during a workday, such as an 8 hour workday) and after administration no longer wears (or needs to wear) a corrective lens during the day. In some embodiments, the individual prior to administration regularly wears a multi-powered corrective lens or at least half a day (e.g., during a workday, such as an 8 hour workday) and after administration no longer wears (or needs to wear) a multi-powered corrective lens during the day (e.g., prior to administration wears a bifocal or progressive glasses and after administration wears a single powered lens such as for treating myopia or astigmatism).

In some embodiments, an individual treated according to a method provided herein is a post-refractive surgery individual and wherein prior to administration and refractive surgery regularly wore a multi-powered corrective lens or at least half a day (e.g., during a workday, such as an 8 hour workday) and after administration and refractive surgery no longer wears (or needs to wear) a corrective lens during the day (e.g., prior to administration wears a bifocal or progressive glasses and after administration no longer wears any corrective lens).

In some embodiments, an ophthalmological composition provided herein and/or administered according to a method provided herein is a pupil selective miotic composition. In some embodiments, the miotic is a pupil selective miotic. In specific embodiments, the pupil selective miotic is aceclidine or an ophthalmically acceptable salt thereof.

In certain embodiments, following administration of the ophthalmological composition according to a method provided herein to the eye, the individual has 3-lines or more improvement in the eye (e.g., at 40 cm, by BCDVA). In some embodiments, following administration of the ophthalmological composition to the eye, the individual has 3-lines or more improvement in the eye within 0.5 hours of administering the second drop to the eye. In certain embodiments, following administration of the ophthalmological composition to the eye, the individual has 3-lines or more improvement for at least 8 hours in the eye. In specific embodiments, following administration of the ophthalmological composition to the eye, the individual has 3-lines or more improvement for at least 10 hours in the eye.

In some embodiments, following administration of the ophthalmological composition to the eye according to a method provided herein, the pupil size of the eye is about 1.5 mm to about 2 mm. In specific embodiments, following administration of the ophthalmological composition to the eye, the pupil size of the eye is about 1.5 mm to about 2 mm within 0.5 hours of administering the second drop to the eye. In some embodiments, following administration of the ophthalmological composition to the eye, the pupil size of the eye is about 1.5 mm to about 2 mm for at least 8 hours. In specific embodiments, following administration of the ophthalmological composition to the eye, the pupil size of the eye is about 1.5 mm to about 2 mm for at least 10 hours. In some embodiments, following administration of the ophthalmological composition to the eye, the pupil size of the eye is about 1.5 mm to about 2 mm for at least 8 hours and no more than about 2.1 mm for at least 10 hours. In some embodiments, the reduction in pupil size is maintained in low light conditions.

In certain embodiments, a composition provided herein comprises a miotic. In specific embodiments, the miotic is aceclidine or a salt thereof. In still more specific embodiments, aceclidine or salt thereof is present in the ophthalmological composition at a concentration of about 1.2 wt. % to about 1.8 wt. %. In some embodiments, the aceclidine is present in the ophthalmological composition at a free base concentration of about 1.4 wt. % to about 1.5 wt. %. In some embodiments, the ophthalmological composition is formulated with about 1.7 wt. % to about 1.8 wt. % aceclidine hydrochloride.

In certain embodiments, an ophthalmological composition provided herein does not comprise a cycloplegic. In certain embodiments, an ophthalmological composition provided herein does not comprise tropicamide.

In certain embodiments, an ophthalmological composition provided herein is preservative-free.

In certain embodiments, an ophthalmological composition provided herein is clear and colorless.

In certain embodiments, an ophthalmological composition provided herein is sterile.

In certain embodiments, an ophthalmological composition provided herein is aqueous.

In certain embodiments, an ophthalmological composition provided herein comprises a thickening agent. In specific embodiments, the thickening agent is hydroxypropyl methylcellulose. In some embodiments, the thickening agent is present in the ophthalmological composition in a concentration of about 1 wt. % to about 1.5 wt. % (e.g., about 1.25 wt. %).

In certain embodiments, an ophthalmological composition provided herein comprises a tonicity agent. In specific embodiments, the tonicity agent is mannitol. In more specific embodiments, the tonicity agent is present in the ophthalmological composition in a concentration of about 2 wt. % to about 3 wt. % (e.g., about 2.5 wt. %).

In certain embodiments, an ophthalmological composition provided herein comprises a lubricant. In specific embodiments, the lubricant is polysorbate 80. In still more specific embodiments, the lubricant is present in the ophthalmological composition in a concentration of about 3 wt. % to about 5 wt. % (e.g., about 4 wt. %).

In certain embodiments, an ophthalmological composition provided herein comprises a chelating agent. In specific embodiments, the chelating agent is edetate (e.g., formulated with edetate disodium dihydrate). In more specific embodiments, the chelating agent is present or formulated into the ophthalmological composition in a concentration of about 0.05 wt. % to about 0.2 wt. % (e.g., formulated with edetate disodium dihydrate at a concentration of about 0.1 wt. %).

In certain embodiments, an ophthalmological composition provided herein comprises a buffering agent. In specific embodiments, the buffering agent is citrate (e.g., formulated with sodium citrate). In more specific embodiments, the buffering agent is present or formulated into the ophthalmological composition in a concentration of about 0.05 wt. % to about 0.15 wt. % (e.g., formulated with sodium citrate at a concentration of about 0.08 wt. %).

In certain embodiments, an ophthalmological composition provided herein has a pH of about 4.5 to about 5.5.

In certain embodiments, an ophthalmological composition provided herein is stored at room temperature (e.g., up to 25° C.) (e.g., up to 3 months, such as for 2-3 months, or up to 6 months) prior to administration.

In certain embodiments, an ophthalmological composition provided herein is stored at 2° C. to 8° C. (e.g., up to 12 months or up to 18 months, such as for 12-18 months) prior to administration. In certain embodiments, an ophthalmological composition provided herein is stored at 2° C. to 8° C. up to 12 months prior to administration. In certain embodiments, an ophthalmological composition provided herein is stored at 2° C. to 8° C. up to 18 months prior to administration. In certain embodiments, an ophthalmological composition provided herein is stored at 2° C. to 8° C. up to 24 months prior to administration.

In certain embodiments, an ophthalmological composition provided herein comprises at least 95 wt. % of the aceclidine present in the composition prior to storage after the composition is stored at 2° C. to 8° C. up to 12 months. In certain embodiments, an ophthalmological composition provided herein comprises at least 95 wt. % of the aceclidine present in the composition prior to storage after the composition is stored at 2° C. to 8° C. up to 18 months. In certain embodiments, an ophthalmological composition provided herein comprises at least 95 wt. % of the aceclidine present in the composition prior to storage after the composition is stored at 2° C. to 8° C. up to 24 months.

In certain embodiments, an ophthalmological composition provided herein is stored at a temperature up to 40° C. (e.g., up to 8 days) prior to administration.

In certain embodiments, an ophthalmological composition provided herein is an eye drop (e.g., slightly viscous ophthalmic solution). In certain embodiments, an ophthalmological composition provided herein, wherein two drops of the ophthalmological composition are administered to the eye (e.g., wherein the two drops are administered about two minutes apart).

In certain embodiments, an individual treated according to a method provided herein is, following treatment, less dependent on or no longer requires wearing a bifocal glasses, progressive glasses, reading glasses, or a contact lens to correct near vision. In certain embodiments, the bifocal glasses, progressive glasses, reading glasses, or contact lens corrects near vision by at least +0.75. In certain embodiments, the bifocal glasses, progressive glasses, reading glasses, or contact lens corrects near vision by at least +1.5. In certain embodiments, the bifocal glasses, progressive glasses, reading glasses, or contact lens corrects near vision by at least +2.0. In certain embodiments, the bifocal glasses, progressive glasses, reading glasses, or contact lens corrects near vision by at least +2.5. In certain embodiments, the bifocal glasses, progressive glasses, reading glasses, or contact lens corrects near vision by at least +3.0. In certain embodiments, the bifocal glasses, progressive glasses, reading glasses, or contact lens corrects near vision by at least +3.5.

In certain embodiments, an individual treated according to a method provided herein has moderate presbyopia. In certain embodiments, an individual treated according to a method provided herein has advanced presbyopia.

In certain embodiments, an individual treated according to a method provided herein has an improvement in near vision (e.g., at 40 cm) of at least 4 lines. In certain embodiments, the individual has an improvement in near vision (e.g., at 40 cm) of at least 5 lines. In certain embodiments, the individual has an improvement in near vision (e.g., at 40 cm) of at least 6 lines.

In certain embodiments, an individual treated according to a method provided herein has an improvement in distance vision (e.g., at 4 m) of at least 1 line.

In certain embodiments, an individual treated according to a method provided herein has an improvement in distance vision (e.g., at 4 m) of at least 3 letters.

In certain embodiments, an individual treated according to a method provided herein is at least 60 years old. In certain embodiments, the individual is 61-65 years old. In certain embodiments, the individual is 66-70 years old.

Provided in certain embodiments herein are systems, compositions, and methods, such as for improving ocular function, such as increasing comfortable screen time and/or treating presbyopia. In specific embodiments, provided herein are systems, compositions, and methods for increasing comfortable screen time.

Provided in certain embodiments herein are systems, compositions, and methods, such as for treating ocular disorders, such as presbyopia. In some embodiments, provided herein is a method of improving vision. In some embodiments, provided herein is a method of improving near vision. In some embodiments, provided herein is a method of improving distance vision. In some embodiments, provided herein is a method of treating presbyopia. In some embodiments, a composition provided herein comprises a composition comprising a miotic (e.g., aceclidine or a salt thereof). In some embodiments, a system provided herein comprises such a composition (e.g., and a vessel containing the composition). In some embodiments, a method provided herein comprises administering such a composition, such as to an eye (e.g., surface) of an individual.

Provided in some embodiments herein is a method of treating presbyopia in an individual (e.g., in need thereof). In certain embodiments provided herein is a method of treating presbyopia in an individual, the method comprising administering an ophthalmological composition to an eye (e.g., an ocular surface thereof) of the individual.

In some embodiments, a method provided herein comprises (e.g., topically) administering a first drop of an ophthalmological composition to an eye (e.g., an ocular surface thereof) of an individual and subsequently administering a second drop of the ophthalmological composition to the eye (e.g., an ocular surface thereof) of the individual. In some embodiments, a composition provided herein comprises a composition comprising a miotic (e.g., aceclidine or a salt thereof).

In some embodiments, provided herein is a method of increasing comfortable screen time in an individual, the method comprising administering an ophthalmological composition comprising a miotic to an eye of the individual. In some embodiments, increasing comfortable screen time comprises increasing the duration of usage of the computer screen before onset of discomfort (e.g., discomfort associated with the eye, such as eye blurriness, eye strain, eye pain, eye irritation, eye associate migraine or headache, computer vision syndrome, or a combination thereof). In certain embodiments, comfortable screen time in the individual lasts for a duration of at least 4 (e.g., consecutive) hours (e.g., 5 hours or more, 6 hours or more, 7 hours or more, or 8 hours or more). In some embodiments, comfortable screen time in the individual lasts for a duration of at least 1 hours (e.g., 2 hours or more, 3 hours or more, 4 hours or more, or 6 hours or more) more than otherwise would have been achieved in the absence of administration of the ophthalmological composition to the eye. In some embodiments, comfortable screen time in the individual is improved for an entire workday (e.g., over a period of about 8 hours) or longer, such as compared to a period of time before administering the ophthalmological composition to the eye. In certain embodiments, increasing comfortable screen time comprises increasing comfortable use of time in a smart phone, computer, electronic tablet, or a combination thereof. In some embodiments, increasing comfortable screen time comprises increasing the duration of usage of the computer screen before onset of eye blurriness, eye strain, eye pain, eye irritation, eye associate migraine or headache, computer vision syndrome, or a combination thereof.

In some embodiments, an ophthalmic composition provided herein is a pupil selective miotic composition.

In some embodiments, an ophthalmic composition provided herein comprises a miotic. In specific embodiments, the miotic is a pupil selective miotic. In some embodiments, the pupil selective miotic is aceclidine or an ophthalmically acceptable salt thereof.

In certain embodiments, following administration of an ophthalmological composition provided herein to an eye, the individual has 3-lines or more improvement in the eye (e.g., at 40 cm, by BCDVA). In some embodiments, following administration of an ophthalmological composition to the eye, the individual has 3-lines or more improvement in the eye within 0.5 hours of administering the second drop to the eye. In certain embodiments, following administration of the ophthalmological composition to the eye, the individual has 3-lines or more improvement for at least 8 hours in the eye. In some embodiments, following administration of an ophthalmological composition to the eye, the individual has 3-lines or more improvement for at least 10 hours in the eye.

In some embodiments, following administration of an ophthalmological composition provided herein to an eye, the pupil size of the eye is about 1.5 mm to about 2 mm. In some embodiments, following administration of an ophthalmological composition to an eye, the pupil size of the eye is about 1.5 mm to about 2 mm within 0.5 hours of administering the second drop to an eye. In certain embodiments, following administration of an ophthalmological composition to an eye, the pupil size of the eye is about 1.5 mm to about 2 mm for at least 8 hours. In some embodiments, an ophthalmological composition to the eye, the pupil size of the eye is about 1.5 mm to about 2 mm for at least 10 hours. In certain embodiments, following administration of an ophthalmological composition to an eye, the pupil size of the eye is about 1.5 mm to about 2 mm for at least 8 hours and no more than about 2.1 mm for at least 10 hours. In some embodiments, reduction in pupil size is maintained in low light conditions.

In certain embodiments, a composition provided herein comprises a miotic. In specific embodiments, the miotic is aceclidine or a salt thereof and is present in the ophthalmological composition at a concentration of about 1.2 wt. % to about 1.8 wt. %. In some embodiments, aceclidine is present in the ophthalmological composition at a free base concentration of about 1.4 wt. % to about 1.5 wt. %. In some embodiments, an ophthalmological composition provided herein is formulated with about 1.7 wt. % to about 1.8 wt. % aceclidine hydrochloride.

In some embodiments, an ophthalmic composition provided herein does not comprise cycloplegic. In some embodiments, an ophthalmic composition provided herein does not comprise tropicamide.

In some embodiments, an ophthalmic composition provided herein is preservative-free (free of an antimicrobial preservative).

In some embodiments, an ophthalmic composition provided herein is clear and colorless.

In some embodiments, an ophthalmic composition provided herein is sterile.

In some embodiments, an ophthalmic composition provided herein is aqueous.

In some embodiments, an ophthalmic composition provided herein comprises a thickening agent. In specific embodiments, the thickening agent is hydroxypropyl methylcellulose. In some embodiments, the thickening agent is present in the ophthalmological composition in a concentration of about 1 wt. % to about 1.5 wt. % (e.g., about 1.25 wt. %).

In some embodiments, an ophthalmic composition provided herein comprises a tonicity agent. In specific embodiments, the tonicity agent is mannitol. In some embodiments, the tonicity agent is present in the ophthalmological composition in a concentration of about 2 wt. % to about 3 wt. % (e.g., about 2.5 wt. %).

In some embodiments, an ophthalmic composition provided herein comprises a lubricant. In specific embodiments, the lubricant is polysorbate 80. In some embodiments, the lubricant is present in the ophthalmological composition in a concentration of about 3 wt. % to about 5 wt. % (e.g., about 4 wt. %).

In some embodiments, an ophthalmic composition provided herein comprises a chelating agent. In specific embodiments, the chelating agent is edetate (e.g., formulated with edetate disodium dihydrate). In some embodiments, the chelating agent is present or formulated into the ophthalmological composition in a concentration of about 0.05 wt. % to about 0.2 wt. % (e.g., formulated with edetate disodium dihydrate at a concentration of about 0.1 wt. %).

In some embodiments, an ophthalmic composition provided herein comprises a buffering agent. In specific embodiments, the buffering agent is citrate (e.g., formulated with sodium citrate). In some embodiments, the buffering agent is present or formulated into the ophthalmological composition in a concentration of about 0.05 wt. % to about 0.15 wt. % (e.g., formulated with sodium citrate at a concentration of about 0.08 wt. %).

In some embodiments, an ophthalmic composition provided herein has a pH of about 4.5 to about 5.5.

In some embodiments, an ophthalmic composition provided herein is stored at room temperature (e.g., up to 25° C.) (e.g., up to 3 months, such as 2-3 months, or up to 6 months) prior to administration.

In some embodiments, an ophthalmic composition provided herein is stored at 2° C. to 8° C. (e.g., up to 12 months or up to 18 months, such as 12-18 months) prior to administration. In certain embodiments, an ophthalmological composition provided herein is stored at 2° C. to 8° C. up to 12 months prior to administration. In certain embodiments, an ophthalmological composition provided herein is stored at 2° C. to 8° C. up to 18 months prior to administration. In certain embodiments, an ophthalmological composition provided herein is stored at 2° C. to 8° C. up to 24 months prior to administration.

In certain embodiments, an ophthalmological composition provided herein comprises at least 95 wt. % of the aceclidine present in the composition prior to storage after the composition is stored at 2° C. to 8° C. up to 12 months. In certain embodiments, an ophthalmological composition provided herein comprises at least 95 wt. % of the aceclidine present in the composition prior to storage after the composition is stored at 2° C. to 8° C. up to 18 months. In certain embodiments, an ophthalmological composition provided herein comprises at least 95 wt. % of the aceclidine present in the composition prior to storage after the composition is stored at 2° C. to 8° C. up to 24 months.

In some embodiments, an ophthalmic composition provided herein is stored at a temperature up to 40° C. (e.g., up to 8 days, such as 1-8 days) prior to administration.

In some embodiments, an ophthalmic composition provided herein is an eye drop (e.g., slightly viscous ophthalmic solution).

In some embodiments, two drops of the ophthalmological composition are administered to the eye (e.g., wherein the two drops are administered about two minutes apart), such as in any method provided herein.

Provided in certain embodiments herein, is a method for treating presbyopia in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye.

Provided in certain embodiments herein, is a method for treating presbyopia and improving distance vision in an individual (e.g., in need thereof), the method comprising opening a first single-patient-use container on a first day and subsequently administering to a first eye of the individual a first drop and a second drop of an ophthalmological composition provided herein (e.g., comprising a miotic, such as aceclidine or a salt thereof) to the first eye of the individual. In some embodiments, the second drop is administered to the eye of the individual about 5 minutes or less after the first drop is administered to the eye. In some embodiments, the second drop is administered to the eye of the individual about 2 minutes after the first drop is administered to the eye.

In certain embodiments, an individual treated according to a method provided herein has moderate presbyopia. In certain embodiments, an individual treated according to a method provided herein has advanced presbyopia.

In certain embodiments, an individual treated according to a method provided herein has an improvement in near vision (e.g., at 40 cm) of at least 4 lines. In certain embodiments, the individual has an improvement in near vision (e.g., at 40 cm) of at least 5 lines. In certain embodiments, the individual has an improvement in near vision (e.g., at 40 cm) of at least 6 lines.

In certain embodiments, an individual treated according to a method provided herein has an improvement in distance vision (e.g., at 4 m) of at least 1 line.

In certain embodiments, an individual treated according to a method provided herein has an improvement in distance vision (e.g., at 4 m) of at least 3 letters.

In certain embodiments, an individual treated according to a method provided herein is at least 60 years old. In certain embodiments, the individual is 61-65 years old. In certain embodiments, the individual is 66-70 years old.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein) of which:

DETAILED DESCRIPTION

Figure 1A:
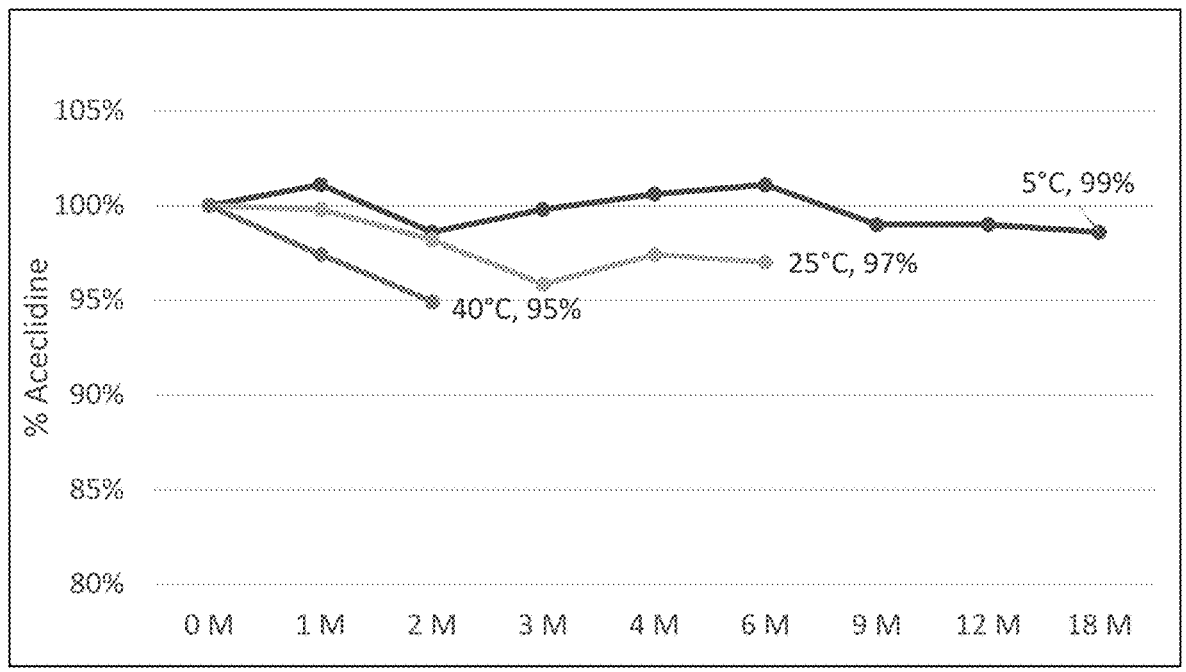
FIG. 1A illustrates the extended stability at temperatures up to 40° C. for an exemplary aceclidine composition described herein comprising a pH of 5.0.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "up to," "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

In some instances, a value is "about" a recited value if the value is within +10% of the recited value. For example, if it is stated, that "the temperature is about 20 Celsius" a value may be "about" 20° C. if it is within ±10% of 20° C., or from 18° C. to 22° C. In more specific instances, a value is "about" a recited value if the value is within ±5% of the recited value. In some instances, a value is "about" a recited value if the value is within ±one significant figure of the recited value. For example, if it is stated, that a concentration is about 2.0 wt. %, the concentration may be about 2.0 wt. % if it is within ±one significant figure of 2.0 wt. %, or from 1.9 wt. % to about 2.1 wt. %. It is also understood that any disclosure provided herein to "about" a number, also includes disclosure of that number itself (i.e., without "about").

The term "comprise" and variations thereof, such as, "comprises" and "comprising" are to be construed in an open, inclusive sense, that is, as "including, but not limited to." It is also to be understood that disclosure of "comprising" is also intended to include disclosures of "consisting essentially of" and "consisting of" the same recited elements. Generally, "consisting essentially of" is to construed at partially open, being directed to those elements set forth and to those other elements that do not materially affect the basic and novel characteristics of the invention described. Generally, "consisting of" means that the claim is directed only to the specified elements.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "optional" or "optionally" denotes that a subsequently described event or circumstance can but need not occur, and that the description includes instances where the event or circumstance occurs and instances in which it does not.

The term "amount of" a component as used herein refers to "volume of" and/or "mass of" of the particular component.

As used herein, the term "weight percent" or "wt. %" refers to weight-weight percent (% w/w) or weight-volume percent (% w/v). In some instances, compositions provided herein comprise or are said to comprise various compounds and salts. In certain instances, compositions provided herein comprise a solvent, such as an aqueous medium. In some instances, compositions provided herein may be described as comprising a salt. In certain instances, the salt of a composition (e.g., aqueous composition) provided herein may be partially or completely dissolved in the composition. However, it is to be understood that irrespective of the form, a composition provided herein that is formulated with a salt comprises that salt, irrespective of whether or not that salt is partially or wholly dissolved in that composition. In some instances, for example, an aqueous composition provided herein that is said to be comprising an aceclidine hydrochloride in an amount of about 1.75 wt. % is understood to comprise aceclidine hydrochloride if (a) the composition was formulated using aceclidine hydrochloride in the appropriate amount (about 1.75 wt. %), or (b) the composition comprises an amount of aceclidine free base (or protonated cation) and a sufficient amount of chloride in the composition that would correspond to aceclidine hydrochloride in an amount of about 1.75 wt. %.

Provided herein is a composition comprising an ophthalmological drug described herein (e.g., aceclidine) and having a pH of 6 or less, such as a pH of about 4 to about 6. In some embodiments, the composition has a pH of about 4.5 to about 6. In some embodiments, the composition has a pH of about 4.5 to about 5.5. In some embodiments, the composition has a pH of about 5 to about 6. In some embodiments, the composition has a pH of about 5.0 to about 5.5. In some embodiments, the composition has a pH of about 5.5 to about 6. In some embodiments, the composition has a pH of about 5. In some embodiments, the composition has a pH of about 5.5. In some embodiments, the composition further comprises a buffer (e.g., an acetate buffer or a citrate buffer), such as at a concentration of about 0.01% to about 1% (e.g., about 0.05% to about 0.2%). In some embodiments, the composition is suitable for ophthalmic administration. In some embodiments, an ophthalmological drug described herein is aceclidine or a salt thereof.

Provided in certain embodiments herein are systems, compositions, and methods, such as for improving ocular function, such as reducing corrective lens wear time and/or treating presbyopia. In specific embodiments, provided herein are systems, compositions, and methods for reducing corrective lens wear time.

Provided in certain embodiments herein are systems, compositions, and methods, such as for treating ocular disorders, such as presbyopia. In some embodiments, an individual described herein does not have or has not been diagnosed with glaucoma. In some embodiments, an individual described herein has presbyopia and does not have or has not been diagnosed with glaucoma.

In some embodiments, provided herein is a method of treating short distance vision.

In some aspects, provided herein is a method of treating presbyopia in an individual using any composition of the disclosure. In some embodiments, the method of treating presbyopia comprises administering the composition to the eye of an individual.

Provided in some embodiments herein is a method of treating presbyopia in an individual (e.g., in need thereof). In certain embodiments provided herein is a method of treating presbyopia in an individual, the method comprising administering an ophthalmological composition to an eye (e.g., an ocular surface thereof) of the individual.

Provided in some embodiments herein is a method of treating presbyopia in an individual (e.g., in need thereof), wherein the individual wears a corrective lens (e.g., a contact lens, reading glasses, or progressive glasses). In certain embodiments provided herein is a method of treating presbyopia in an individual, the method comprising administering an ophthalmological composition to an eye (e.g., an ocular surface thereof) of the individual. In some embodiments, the individual wears reading glasses having a power of at least +0.75. In some embodiments, the individual wears reading glasses having a power of at least +1.0. In some embodiments, the individual wears reading glasses having a power of at least +1.5. In some embodiments, the individual wears reading glasses having a power of at least +2.0. In some embodiments, the individual wears reading glasses having a power of at least +2.5. In some embodiments, the individual wears reading glasses having a power of at least +3.0. In some embodiments, the individual wears reading glasses having a power of at least +3.5. In certain embodiments, the individual wears a progressive lens with a near vision correction of any reading glasses described herein.

Provided in some embodiments herein is a method of reducing corrective lens usage in an individual (e.g., in need thereof), wherein the individual wears a corrective lens (e.g., a contact lens, reading glasses, or progressive glasses). In certain embodiments provided herein is a method of treating presbyopia in an individual, the method comprising administering an ophthalmological composition to an eye (e.g., an ocular surface thereof) of the individual. In some embodiments, the individual wears reading glasses having a power of at least +0.75. In some embodiments, the individual wears reading glasses having a power of at least +1.0. In some embodiments, the individual wears reading glasses having a power of at least +1.5. In some embodiments, the individual wears reading glasses having a power of at least +2.0. In some embodiments, the individual wears reading glasses having a power of at least +2.5. In some embodiments, the individual wears reading glasses having a power of at least +3.0. In some embodiments, the individual wears reading glasses having a power of at least +3.5. In certain embodiments, the individual wears a progressive lens with a near vision correction of any reading glasses described herein.

Provided in some embodiments herein is a method of treating presbyopia with a concomitant improvement in myopia in an individual (e.g., in need thereof). In certain embodiments provided herein is a method of treating presbyopia with a concomitant improvement in myopia in an individual, the method comprising administering an ophthalmological composition to an eye (e.g., an ocular surface thereof) of the individual.

Provided in some embodiments herein is a method of treating presbyopia with a concomitant improvement in distance vision in an individual (e.g., in need thereof). In certain embodiments provided herein is a method of treating presbyopia with a concomitant improvement in distance vision in an individual, the method comprising administering an ophthalmological composition to an eye (e.g., an ocular surface thereof) of the individual.

In some embodiments, increasing comfortable screen time comprises increasing the duration of usage of the computer screen. In specific embodiments, increasing comfortable screen time comprises increasing the duration of usage of the computer screen before onset of discomfort (e.g., discomfort associated with the eye). In more specific embodiments, discomfort associated with the eye is eye blurriness, eye strain, eye pain, eye irritation, eye associate migraine or headache, computer vision syndrome, or a combination thereof.

In some embodiments, comfortable screen time in the individual lasts for a duration of about 2 (e.g., continuous) hours or more. In some embodiments, comfortable screen time in the individual lasts for a duration of about 3 (e.g., continuous) hours or more. In some embodiments, comfortable screen time in the individual lasts for a duration of about 4 (e.g., continuous) hours or more. In some embodiments, comfortable screen time in the individual lasts for a duration of about 5 (e.g., continuous) hours or more. In some embodiments, comfortable screen time in the individual lasts for a duration of about 6 (e.g., continuous) hours or more. In some embodiments, comfortable screen time in the individual lasts for a duration of about 7 (e.g., continuous) hours or more. In some embodiments, comfortable screen time in the individual lasts for a duration of about 8 (e.g., continuous) hours or more.

In some embodiments, comfortable screen time in the individual lasts for a duration of about 30 (e.g., continuous) minutes or more than otherwise would have been achieved in the absence of administration of an ophthalmological composition provided herein to the eye. In some embodiments, comfortable screen time in the individual lasts for a duration of about 1 (e.g., continuous) hours or more than otherwise would have been achieved in the absence of administration of an ophthalmological composition provided herein to the eye. In some embodiments, comfortable screen time in the individual lasts for a duration of about 2 (e.g., continuous) hours or more than otherwise would have been achieved in the absence of administration of an ophthalmological composition provided herein to the eye. In some embodiments, comfortable screen time in the individual lasts for a duration of about 3 (e.g., continuous) hours or more than otherwise would have been achieved in the absence of administration of an ophthalmological composition provided herein to the eye. In some embodiments, comfortable screen time in the individual lasts for a duration of about 4 (e.g., continuous) hours or more than otherwise would have been achieved in the absence of administration of an ophthalmological composition provided herein to the eye. In some embodiments, comfortable screen time in the individual lasts for a duration of about 5 (e.g., continuous) hours or more than otherwise would have been achieved in the absence of administration of an ophthalmological composition provided herein to the eye. In some embodiments, comfortable screen time in the individual lasts for a duration of about 6 (e.g., continuous) hours or more than otherwise would have been achieved in the absence of administration of an ophthalmological composition provided herein to the eye. In some embodiments, comfortable screen time in the individual lasts for a duration of about 7 (e.g., continuous) hours or more than otherwise would have been achieved in the absence of administration of an ophthalmological composition provided herein to the eye.

In some embodiments, comfortable screen time in an individual described herein is improved, such as to last for an entire workday (e.g., over a period of about 8 hours) or longer.

In some embodiments, comfortable screen time in an individual described herein is improved compared to a period of time before administering an ophthalmological composition provided herein to the eye.

In some embodiments, increasing comfortable screen time comprises increasing comfortable use of time of any suitable electronic device (e.g., with a screen). In specific embodiments, increasing comfortable screen time comprises increasing comfortable use of time of a smart phone, computer, electronic tablet, or a combination thereof.

In some embodiments, a method provided herein comprises (e.g., topically) administering a first drop of an ophthalmological composition to an eye (e.g., an ocular surface thereof) of an individual and subsequently administering a second drop of the ophthalmological composition to the eye (e.g., an ocular surface thereof) of the individual.

In some embodiments, a first drop and a second drop of an ophthalmological composition (e.g., provided herein) is administered to an eye of an individual within less than 5 minutes of each other. In specific embodiments, the first drop and the second drop are administered within 3 minutes of each other. In more specific embodiments, the second drop is administered about 1 to about 3 minutes after the first drop. In still more specific embodiments, the second drop is administered about 2 minutes after the first drop. In yet more specific embodiments, the second drop is administered 2 minutes after the first drop. In some embodiments, a drop is administered in a first eye and a second eye immediately (e.g., within 15 seconds) after the drop is administered to the first eye and about 2 minutes later, another drop is administered in a first eye and a second eye immediately (e.g., within 15 seconds) after the drop is administered to the first eye. In some instances, it is surprising that extended duration of the effect of the method can be achieved by administering 2 drops within 5 minutes of each other, including as little as about 2 minutes of each other. In certain instances, administration of 2 drops within as little as about 2 minutes can improve patient compliance with the administration protocol (e.g., of 2 drops administration) and/or decrease potential for contamination of an open composition between administration of the 2 drops for a longer period.

Provided in some embodiments herein is a method of treating presbyopia in an individual (e.g., in need thereof). In some embodiments, a method provided herein consists essentially of (e.g., topically) administering (e.g., instilling) a first drop of an ophthalmological composition to an eye (e.g., an ocular surface thereof) of an individual and subsequently administering a second drop of the ophthalmological composition to the eye (e.g., an ocular surface thereof) of the individual, wherein the second drop is administered within about 2 minutes of the first drop. In specific embodiments, the second drop is administered about 2 minutes after the first drop.

Provided in some embodiments herein is a method of treating presbyopia in an individual (e.g., in need thereof), the method comprising (e.g., topically) administering a dose of an ophthalmological composition to an eye (e.g., an ocular surface thereof) of an individual. In certain embodiments, the dose of the ophthalmological composition comprises a first drop of the ophthalmological composition and subsequently administering a second drop of the ophthalmological composition. In some embodiments, the first drop and the second drop are administered at any suitable frequency, such as a frequency described herein (e.g., a second drop being administered 2 minutes after the first drop).

In some embodiments provided herein is a method for treating presbyopia, the method comprising administering a dose once daily. In some embodiments provided herein is a method for treating presbyopia, the method consisting essentially of administering a dose once daily. In some embodiments, the once daily dose is administered 5 days a week (or any suitable number of days a week), such as during the work week.

In some embodiments provided herein is a method for treating presbyopia, the method comprising administering a dose on a first day and a second day. In some embodiments, the first day dose comprises administering a first drop and a second drop on the first day. In some embodiments, the second day dose comprises administering a third drop and a fourth drop on the second day.

In some embodiments provided herein is a method for treating presbyopia, the method comprising administering a first dose (e.g., a first drop and a second drop is administered, such as about 2 minutes apart) to a first eye of an individual and a second dose (e.g., a third drop and a fourth drop is administered, such as about 2 minutes apart) to a second eye of an individual. In certain embodiments, (i) a first dose is administered to a first eye on a first day, (ii) a second dose is administered to a second eye on the first day, (iii) a third dose is administered to the first eye on a second day, and (iv) a fourth dose is administered to the second eye on the second day.

In some embodiments provided herein is a system comprising a (e.g., single-use) container and an ophthalmological composition. In certain embodiments, provided herein is a method of using any system or composition provided herein, such as improving vision (e.g., improving near vision, or improving distance vision). In certain embodiments, provided herein is a method of using any system or composition provided herein, such as in the treatment of presbyopia. In some embodiments, the method comprises administering a composition provided herein. In certain embodiments, provided herein is a method comprising opening a container of a system provided herein and dispensing a composition provided herein.

Provided in some embodiments herein is a method of improving vision (e.g., improving near vision, or improving distance vision) in an individual (e.g., in need thereof). In certain embodiments provided herein is a method of improving vision (e.g., improving near vision, or improving distance vision) in an individual, the method comprising administering an ophthalmological composition to an eye (e.g., an ocular surface thereof) of the individual.

Provided in some embodiments herein is a method of improving near vision in an individual (e.g., in need thereof). In certain embodiments provided herein is a method of improving near vision in an individual, the method comprising administering an ophthalmological composition to an eye (e.g., an ocular surface thereof) of the individual.

Provided in some embodiments herein is a method of improving distance vision in an individual (e.g., in need thereof). In certain embodiments provided herein is a method of improving distance vision in an individual, the method comprising administering an ophthalmological composition to an eye (e.g., an ocular surface thereof) of the individual.

Provided in some embodiments herein is a method of improving near vision and improving distance vision in an individual (e.g., in need thereof). In certain embodiments provided herein is a method of improving near vision and improving distance vision in an individual, the method comprising administering an ophthalmological composition to an eye (e.g., an ocular surface thereof) of the individual.

In some embodiments, a single-use container (also referred interchangeably herein as a single-patient-use container) comprises an enclosed chamber. In specific embodiments, any ophthalmological composition provided herein is configured within the enclosed chamber (of a single use container described herein).

In certain embodiments, the single-use container is configured to be opened in any suitable manner. In specific embodiments, the single-use container is configured to be irreversibly opened (e.g., wherein when opened, the chamber of the single-use container is no longer enclosed, instead having an opening having fluid connectivity to the exterior of the chamber). In some embodiments, a single-use container provided herein is configured when open (or after being opened) to dispense (e.g., from the chamber of the single-use container to the exterior of the chamber or container) at least one drop of any composition, such as a composition provided herein.

In some embodiments, a method provided herein comprises opening a single-use container, such as provided herein, administering a first drop and a second drop (e.g., about 2 minutes apart) (e.g., a first dose) of an ophthalmological composition from the single-use container to a first eye of an individual. In specific embodiments, the method comprises administering a third drop and a fourth drop (e.g., about 2 minutes apart) (e.g., a second dose) of the ophthalmological composition from the single-use container to a second eye of an individual. In certain embodiments, such administration can occur on multiple days, a first day and a second day, or other suitable frequency, such as daily or every workday or the like.

In some embodiments, a container provided or used herein comprises a container body, a container neck, and a container head (e.g., wherein the head and body are connected at the neck). In specific embodiments, the container body and the container head having a larger cross-sectional dimension than the container neck. In some embodiments, an enclosed chamber extends from the container body into the container neck (e.g., enclosed within the container, such as before the container is opened). In some embodiments, the container is configured to be opened in any suitable manner. In specific embodiments, the container is configured to be opened at the container neck (e.g., by separating the head from the body, such as by unscrewing a threaded portion or by breaking the container at the container neck). In some embodiments, the container neck is configured for ease of breaking, such as through use of scoring on the neck or through use of a thinner material in the neck (e.g., relative to the body and/or head).

Figure 12:
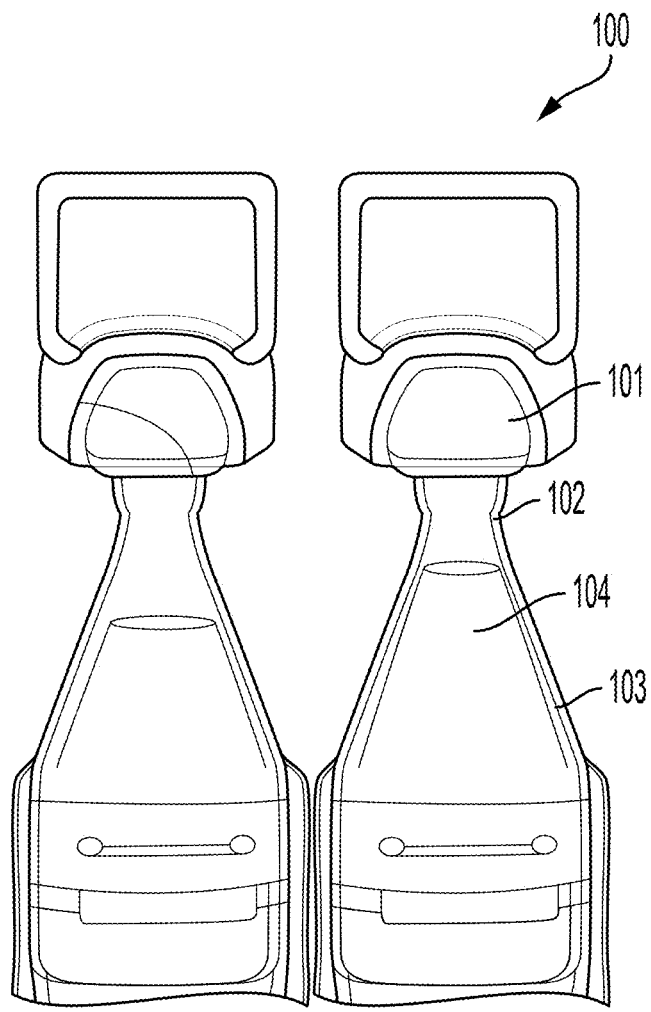
FIG. 12 illustrates a pair of exemplary single use containers that when taken together with a composition provided herein forms an exemplary system provided herein.

FIG. 12 illustrates a pair of exemplary single use containers 100 that when taken together with a composition provided herein forms an exemplary system provided herein. As demonstrated in FIG. 1, a container provided herein may comprise a head 101, a neck 102, and a body 103. As illustrated the neck 102 may be narrower than the head 101 and/or body 103. In some instances, such a configuration facilitates opening the vial at the neck 102, such as by breaking the head 101 from the body 103. In some instances, an enclosed chamber 104 resides within the body 103 and may extend into the neck 102 and head 101, such that when the head 101 is separated from the body 103, such as at the neck 102, an opening or orifice is formed, from which one or more drop of a composition contained within the enclosed chamber 104 may be dispensed.

In certain embodiments, the container of a system or method described herein is an ampoule or vial, such as made from or comprising any suitable material. In some embodiments, the ampoule is a plastic ampoule or vial (e.g., wherein the ampoule or vial comprises plastic, or is substantially, such as at least 95%, comprised of plastic). In other embodiments, the ampoule or vial is a glass ampoule or vial (e.g., wherein the ampoule or vial comprises glass, or is substantially, such as at least 95%, comprised of glass).

In some embodiments, a container provided herein is sterile, such as sterile within the chamber. In certain embodiments, the chamber of the container if sterile prior to opening of an enclosed chamber of the container. In specific embodiments, the container is an ampoule or vial and the ampoule or vial is sterile (e.g., before and/or after filling the ampoule or vial with a composition provided herein).

In certain embodiments, the container comprises or is comprised of any suitable material. In specific embodiments, the container comprises (or is comprised of) a plastic. In some embodiments, the container comprises (or is comprised of) polyethylene. In specific embodiments, the container or container body or container body/neck consists essentially of polyethylene. In some embodiments, the container comprises (or is comprised of) low-density polyethylene (LDPE). In specific embodiments, the container or container body or container body/neck consists essentially of low-density polyethylene (LDPE).

In some embodiments, the container is transparent (e.g., the material from which the container is made is transparent). In certain embodiments, the container is sufficiently transparent to see the composition within, such as the amount of composition within and/or the color of the composition within.

In some embodiments, a container provided herein is configured to hold about 0.05 ml to about 5 mL of a composition within an enclosed chamber thereof (e.g., prior to opening). In specific embodiments, the container provided herein is configured to hold about 0.1 mL to about 1 ml of a composition within an enclosed chamber thereof (e.g., prior to opening). In some embodiments, the container provided herein is configured to hold about 0.2 mL to about 2 mL of a composition within an enclosed chamber thereof (e.g., prior to opening). In specific embodiments, the container provided herein is configured to hold about 0.2 mL to about 1 mL of a composition within an enclosed chamber thereof (e.g., prior to opening). In more specific embodiments the container provided herein is configured to hold about 0.5 ml of a composition within an enclosed chamber thereof (e.g., prior to opening).

In certain embodiments, any container provided herein is configured to dispense a drop from an opening thereof (e.g., an opening created after opening or irreversibly opening the container). In specific embodiments, the container is configured to dispense a drop having a volume of about 0.01 mL to about 0.06 mL. In more specific embodiments, the container is configured to dispense a drop having a volume of about 0.02 mL to about 0.05 mL. In still more specific embodiments, the container is configured to dispense a drop having a volume of about 0.03 mL to about 0.04 mL.

In certain embodiments, provided herein is a system comprising a single use container (also referred to herein as a single-patient-use container) and a (e.g., ophthalmological) composition comprising aceclidine or a salt thereof. In some instances, systems provided herein facilitate the use of a dissolved aceclidine that has good stability, including at extended storage times (e.g., including under refrigerated and room temperature storage conditions).

In some embodiments, systems provided herein comprise a composition providing good stability, such as during storage (e.g., at room temperature and/or cold storage). In some instances, stability of a composition such as described herein is provided by using a system described herein. In certain instances, good stability of a composition provided herein is achieved in a system described herein even in the absence of an inert gas filling in the headspace (e.g., the void of the chamber not filled by a composition described herein) in the chamber of a container described herein.

In some embodiments, a system provided herein comprises a composition contained within a chamber of a container described herein. In certain embodiments, the remaining space with the chamber (the headspace) is filled with the gas. In some embodiments, the headspace does not need to be filled with an inert gas. In some embodiments, the headspace is not filled with an inert gas. In certain embodiments, the headspace is filled with a gas comprising oxygen, such as an air. In some embodiments, such a system surprisingly provides good long time storage stability such as described herein even in the absence of an inert gas overlay (e.g., in the headspace).

In certain embodiments, no more than 2 drops (e.g., a first drop and a second drop) of an ophthalmological composition are administered to an eye of an individual in a single day. In certain embodiments, no more than 4 drops of an ophthalmological composition are administered to an individual in a single day (e.g., no more than 2 drops to a first eye and 2 drops to a second eye). In certain instances, limiting dose to no more than 2 drops in an eye in a day provides good therapeutic effect while also reducing potential for adverse effect that can be caused by alternative product that may use or require more frequent daily dosing.

In some embodiments, a method provided herein provides a therapeutic effect, such as in treating presbyopia. In some embodiments, a therapeutic effect provided by a method provided herein includes improving near vision, targeted pupil size, or a combination thereof. In certain instances, a therapeutic effect provided by a method described herein extends for a desirable duration such as for 8 hours or more (e.g., 10 hours or more). In some instances, a therapeutic effect provided by a method described herein is achieved without substantial loss of distance vision, dimming, or a combination thereof.

In some embodiments, a method provided herein provides a therapeutic effect, such as in treating presbyopia. In some embodiments, a method provided herein provides a therapeutic effect, such as in improving near-vision. In some embodiments, a therapeutic effect provided by a method provided herein includes improving near vision, targeted pupil size, or a combination thereof. In certain instances, a therapeutic effect provided by a method described herein extends for a duration of 10 hours or more. In some instances, a therapeutic effect provided by a method described herein is achieved without substantial loss of distance vision, dimming, or a combination thereof.

In some embodiments, a method provided herein provides a therapeutic effect, such as in treating presbyopia. In some embodiments, a method provided herein provides a therapeutic effect, such as in improving near-vision. In some embodiments, a therapeutic effect provided by a method provided herein includes improving near vision, targeted pupil size, or a combination thereof. In certain instances, a therapeutic effect is provided within 30 minutes following administration of a composition according to a method described herein (e.g., extends for a duration of 10 hours or more). In some instances, a therapeutic effect provided by a method described herein is achieved without substantial loss of distance vision, dimming, or a combination thereof.

In some embodiments, a pupil size of an eye of an individual following administration of an ophthalmological composition described herein (e.g., according to a method provided herein) to the eye is about 1.5 mm to about 2.0 mm. In some embodiments, a pupil size of about 1.5 mm to about 2.0 mm is achieved within 30 minutes of administration of the dose (e.g., 2 drops about 2 minutes apart) to the eye. In some embodiments, a pupil size of about 1.5 mm to about 2.0 mm is maintained (e.g., after being achieved) for at least 8 hours following administration of the dose (e.g., 2 drops about 2 minutes apart) to the eye. In some embodiments, a pupil size of about 1.5 mm to about 2.0 mm is maintained (e.g., after being achieved) for at least 9 hours following administration of the dose (e.g., 2 drops about 2 minutes apart) to the eye. In some embodiments, a pupil size of about 1.5 mm to about 2.0 mm is maintained (e.g., after being achieved) for at least 10 hours following administration of the dose (e.g., 2 drops about 2 minutes apart) to the eye. In some embodiments, a pupil size of no more than 2.1 mm is maintained (e.g., after being achieved) for at least 10 hours following administration of the dose (e.g., 2 drops about 2 minutes apart) to the eye. In some embodiments, a pupil size of no more than 2.35 mm is maintained (e.g., after being achieved) for at least 10 hours following administration of the dose (e.g., 2 drops about 2 minutes apart) to the eye. In some embodiments, effect of a method provided herein is maintained for sufficient amount of time, such as an entire workday (e.g., over a period of about 8 hours).

In some embodiments, the reduction in pupil size is maintained in low light conditions. In certain embodiments, the reduction in pupil size is maintained indoor, such as in an office. In some instances, benefits of a composition provided herein being administered to the eye can be maintained even in conditions such as low light in an office, etc. where pupil dilation would normally be expected to occur. In some embodiments, low light condition is less than about 2000 candela per square meter ($cd/m^2$). In some embodiments, low light condition is less than about 200 $cd/m^2$. In some embodiments, low light condition is less than about 20 $cd/m^2$.

In some embodiments, near vision of an eye of an individual following administration of an ophthalmological composition described herein (e.g., according to a method provided herein) to the eye is improved by at least 2 lines. In some embodiments, the near vision is improved by 3 lines or more in the eye.

In some embodiments, near vision improvement (e.g., at least 2 lines) is achieved within 30 minutes of administration of the dose (e.g., 2 drops about 2 minutes apart) to the eye. In some embodiments, near vision improvement (e.g., at least 3 lines) is achieved within 30 minutes of administration of the dose (e.g., 2 drops about 2 minutes apart) to the eye. In some embodiments, near vision improvement (e.g., at least 2 lines) is achieved within 60 minutes of administration of the dose (e.g., 2 drops about 2 minutes apart) to the eye. In some embodiments, near vision improvement (e.g., at least 3 lines) is maintained (e.g., after being achieved) for at least 8 hours following administration of the dose (e.g., 2 drops about 2 minutes apart) to the eye. In some embodiments, near vision improvement (e.g., at least 2 lines) is maintained (e.g., after being achieved) for at least 10 hours following administration of the dose (e.g., 2 drops about 2 minutes apart) to the eye. In some embodiments, near vision improvement (e.g., at least 3 lines) is maintained (e.g., after being achieved) for at least 9 hours following administration of the dose (e.g., 2 drops about 2 minutes apart) to the eye. In some embodiments, near vision improvement (e.g., at least 3 lines) is maintained (e.g., after being achieved) for at least 10 hours following administration of the dose (e.g., 2 drops about 2 minutes apart) to the eye.

In some embodiments, a method of treating presbyopia provided herein is a method of treating moderate presbyopia (e.g., the method comprising administrating a composition provided herein, such as using any method provided herein). In some instances, an individual with moderate presbyopia has 20/50 to 20/80 vision at 40 cm. In some embodiments, the method of treating moderate presbyopia in an individual provides at least 3-line improvement in near vision (e.g., at 40 cm) in the individual. In some embodiments, the method of treating moderate presbyopia in an individual provides at least 4-line improvement in near vision (e.g., at 40 cm) in the individual.

In some embodiments, a method of treating presbyopia provided herein is a method of treating advanced presbyopia (e.g., the method comprising administrating a composition provided herein, such as using any method provided herein). In some instances, an individual with advanced presbyopia has >20/80 vision (i.e., worse than 20/80 vision) at 40 cm. In some embodiments, the method of treating advanced presbyopia in an individual provides at least 4-line improvement in near vision (e.g., at 40 cm) in the individual. In some embodiments, the method of treating advanced presbyopia in an individual provides at least 5-line improvement in near vision (e.g., at 40 cm) in the individual. In some embodiments, the method of treating advanced presbyopia in an individual provides at least 6-line improvement in near vision (e.g., at 40 cm) in the individual.

Figure 9:
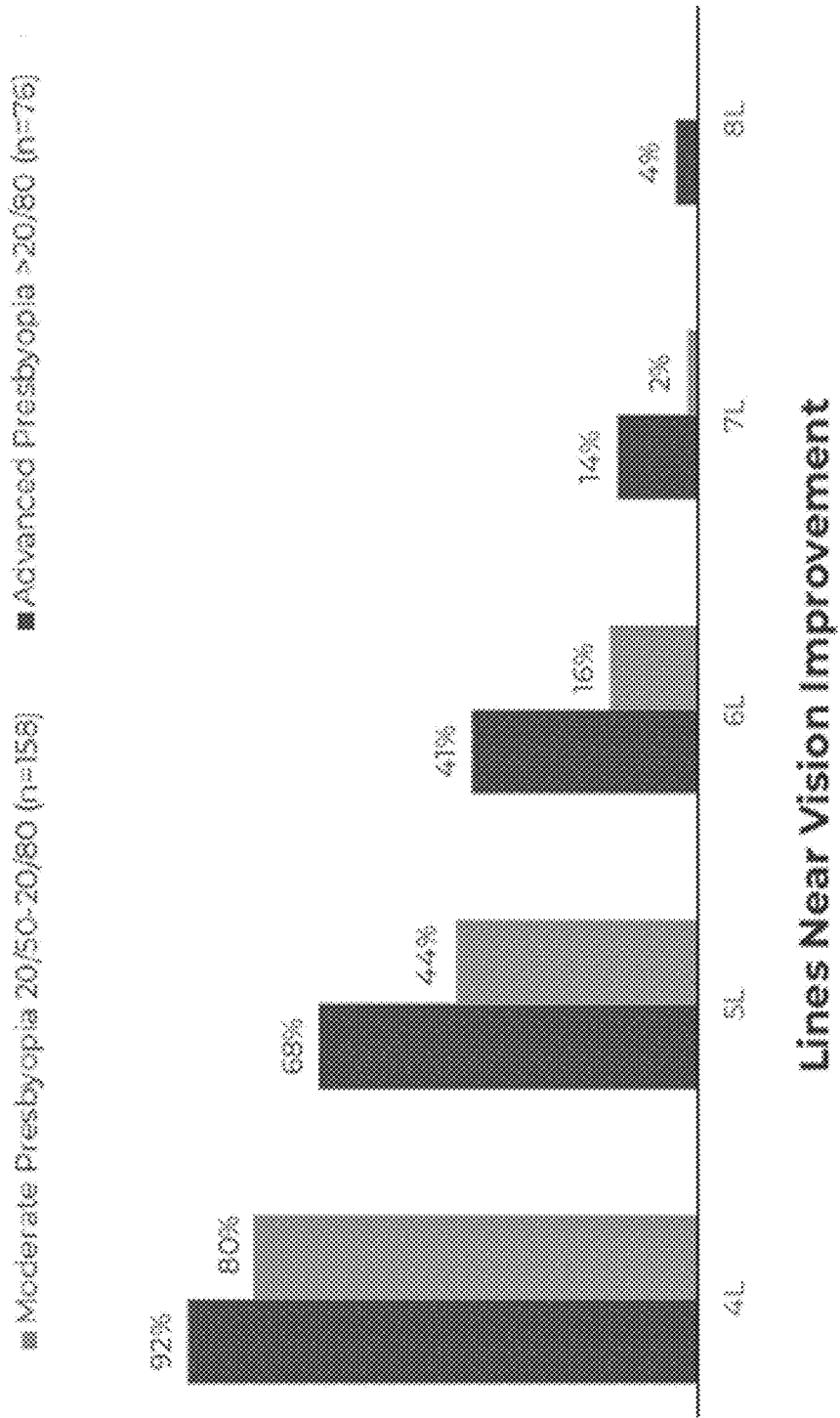
FIG. 9 illustrates near vision improvement in individuals with moderate and advanced presbyopia.

In some embodiments, a method of treating presbyopia provided herein (e.g., a method of treating moderate or advanced presbyopia) in an individual provides a vision of 20/32 or better in the individual (e.g., at 40 cm). FIG. 9 illustrates near vision improvement in individuals with moderate and advanced presbyopia.

In some embodiments, a method of treating presbyopia provided herein is a method of treating presbyopia in an individual needing greater than a 3-line improvement in near vision (e.g., at 40 cm). In some embodiments, a method of treating presbyopia provided herein is a method of treating presbyopia in an individual needing greater than a 4-line improvement in near vision (e.g., at 40 cm). In some embodiments, a method of treating presbyopia provided herein is a method of treating presbyopia in an individual needing greater than a 5-line improvement in near vision (e.g., at 40 cm). In some embodiments, a method of treating presbyopia provided herein is a method of treating presbyopia in an individual needing greater than a 6-line improvement in near vision (e.g., at 40 cm).

In some embodiments, the method of treating presbyopia in an individual provides at least 3-line improvement in near vision (e.g., at 40 cm) in the individual. In some embodiments, the method of treating presbyopia in an individual provides at least 4-line improvement in near vision (e.g., at 40 cm) in the individual. In some embodiments, the method of treating presbyopia in an individual provides at least 5-line improvement in near vision (e.g., at 40 cm) in the individual. In some embodiments, the method of treating presbyopia in an individual provides at least 6-line improvement in near vision (e.g., at 40 cm) in the individual.

Figure 11:
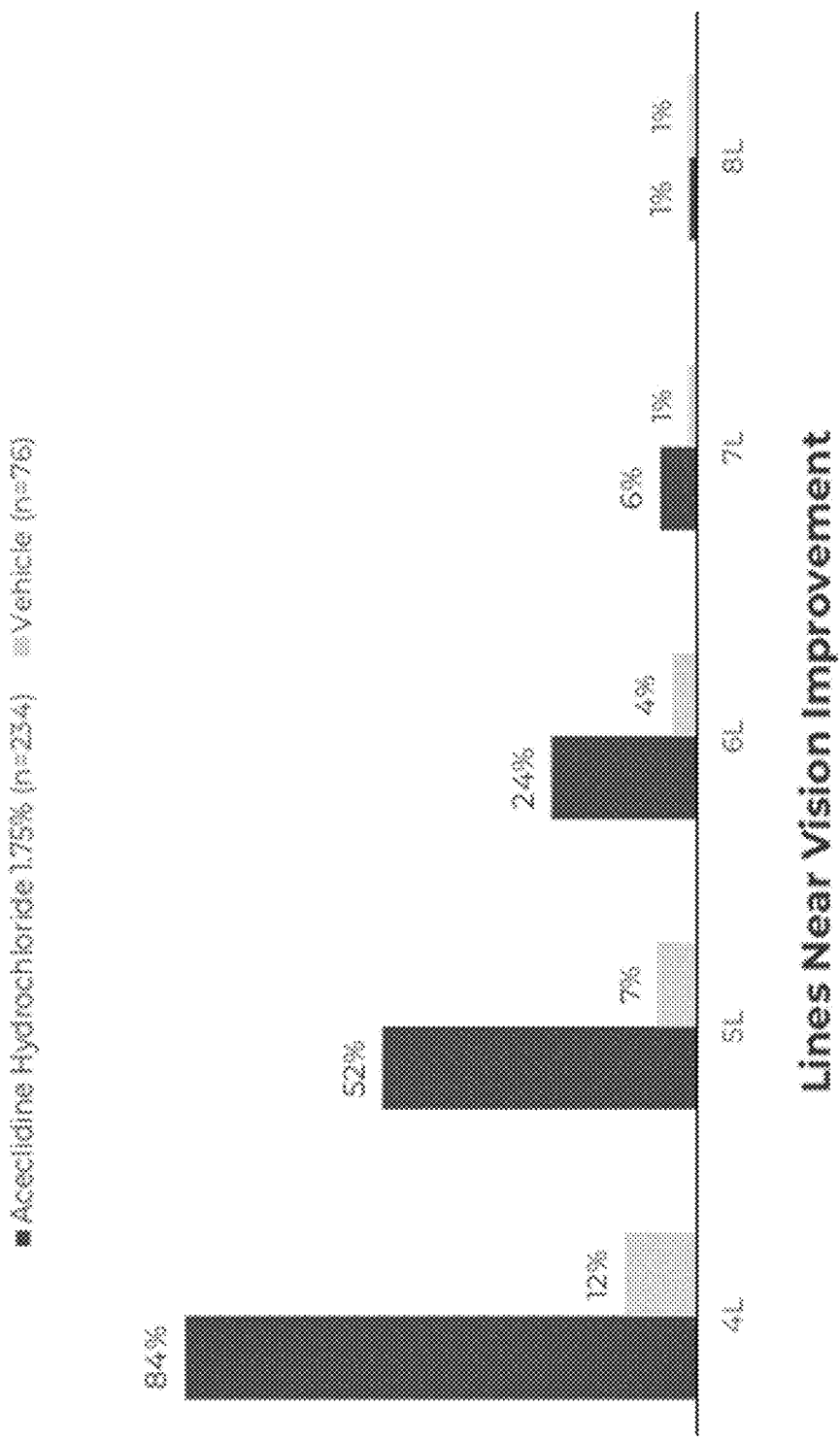
FIG. 11 illustrates near vision improvement of at least 4 lines and up to 8 lines in individuals with presbyopia.

FIG. 11 illustrates near vision improvement of at least 4 lines and up to 8 lines in individuals with presbyopia.

In some instances, near vision improvement is determined in any suitable manner. In specific instances, near vision improvement is determined by (e.g., high contrast) best corrected distance visual acuity (BCDVA) at 40 cm, such as High Contrast BCDVA. In some instances, BCDVA protocols are understood by the skilled artisan, such as provided in DIAMOND BCdVA & Refraction Guideline Version 1.0_Final_01/12/2016.

In some embodiments, no loss of 1 line or more (e.g., greater than or equal to 5 letters) of distance vision is achieved following administration of an ophthalmological composition described herein (e.g., according to a method provided herein, such as 2 drops about 2 minutes apart) to the eye (e.g., within 8 or 10 hours).

In some embodiments, a method provided herein provides improvement of at least 2 letters of distance vision (e.g., following administration of an ophthalmological composition described herein (e.g., according to a method provided herein, such as 2 drops about 2 minutes apart) to the eye (e.g., for 8 or 10 hours)). In some embodiments, a method provided herein provides improvement of 2-4 letters of distance vision (e.g., following administration of an ophthalmological composition described herein (e.g., according to a method provided herein, such as 2 drops about 2 minutes apart) to the eye (e.g., for 8 or 10 hours)). In some embodiments, a method provided herein provides improvement of at least 3-4 letters of distance vision (e.g., following administration of an ophthalmological composition described herein (e.g., according to a method provided herein, such as 2 drops about 2 minutes apart) to the eye (e.g., for 8 or 10 hours)). In some embodiments, a method provided herein provides improvement of at least 1 line of distance vision (e.g., following administration of an ophthalmological composition described herein (e.g., according to a method provided herein, such as 2 drops about 2 minutes apart) to the eye (e.g., for 8 or 10 hours)). In some embodiments, the distant vision is improved for at least 8 hours. In some embodiments, the distant vision is improved for at least 10 hours. In some embodiments, the distant vision is improved within 30 minutes.

In some instances, distance vision loss is determined in any suitable manner. In specific instances, distance vision loss is determined by best corrected distance visual acuity (BCDVA) at 4 meters.

In some embodiments, the ophthalmological composition can be administered to the eye for any suitable or desirable duration. In certain embodiments, dosing according to a method provided herein can last at least 6 weeks. In certain embodiments, dosing according to a method provided herein can last at least 24 weeks.

In certain embodiments, an ophthalmological composition provided herein (e.g., in any system described herein) comprises a miotic agent (e.g., aceclidine) or a salt thereof. In some embodiments, the miotic is a pupil selective miotic, such as aceclidine or a salt thereof. In certain embodiments, an ophthalmological composition provided herein (e.g., in any system described herein) comprises aceclidine or a salt thereof. In specific embodiments, the ophthalmological composition comprises (or is formulated with) aceclidine or a salt thereof in a concentration of about 1 wt. % to about 2 wt. %. In specific embodiments, the ophthalmological composition is formulated with an aceclidine salt, such as aceclidine hydrochloride, in an amount of about 1.6 wt. % to about 1.8 wt. % (e.g., about 1.75 wt. %). In certain embodiments, the ophthalmological composition comprises aceclidine in an amount of about 1.4 wt. % to about 1.5 wt. %, such as about 1.44 wt. % to about 1.46 wt. % (e.g., based on free base concentration of aceclidine).

In some embodiments, an ophthalmological composition provided herein is a pupil selective miotic composition (e.g., comprising a pupil selective miotic such as aceclidine or a salt thereof). In some embodiments, a pupil selective miotic composition or a pupil selective miotic selectively (but not necessarily exclusively) constricts the pupil relative to the ciliary muscle. In some instances, selectivity includes greater activity on the pupil relative to the ciliary such as at least 1.2×, at least 1.5×, at least 2×, at least 3×, at least 5×, at least 10×, at least 20×, or the like (e.g., as determined by the concentration required to produce 50% of a maximum ciliary response (longitudinal or circular) divided by a concentration required to reduce 50% maximum iris sphincter response).

In some instances, a selective miotic reduces risk of adverse effects. In certain instances, this may allow more efficacy of a longer therapies, particularly in individuals who have previously had ocular surgeries such as an ocular surgery described herein.

Provided in some embodiments herein is a method of treating presbyopia in an individual, the method comprising administering an ophthalmological composition to an eye of the individual, and the eye of the individual having previously undergone ocular surgery.

Also, provided in some embodiments herein is a method of treating presbyopia in an individual, the method comprising administering aceclidine or a salt thereof to an eye of the individual, and the eye of the individual having previously undergone ocular surgery.

In some embodiments, an individual treated by any method provided herein has previously undergone ocular surgery and that ocular surgery is a post-refractive surgery (e.g., in an eye treated according to a method provided herein).

In some embodiments, an individual treated by any method provided herein has previously undergone ocular surgery and that ocular surgery is a laser assisted in situ keratomileusis (LASIK) surgery (e.g., in an eye treated according to a method provided herein).

In some embodiments, an individual treated by any method provided herein has previously undergone ocular surgery and that ocular surgery is a photorefractive keratectomy (PRK) surgery (e.g., in an eye treated according to a method provided herein).

In some embodiments, an individual treated by any method provided herein is a pseudophakia individual.

In some embodiments, an individual treated by any method provided herein has previously undergone ocular surgery and that ocular surgery is a post cataract-intraocular lens (IOL) surgery (e.g., in an eye treated according to a method provided herein).

In some embodiments, an individual treated by any method provided herein has previously undergone ocular surgery and that ocular surgery is a post-installation of fake lens surgery (e.g., in an eye treated according to a method provided herein).

In certain instances, an individual treated according to a method provided herein prior to surgery wore a corrective contact lens or corrective glasses (e.g., bifocals), and after surgery and administration of the ophthalmological composition, the individual does not need to (or does not) wear the corrective contact lens or corrective glasses (e.g., bifocals).

In certain instances, an individual treated according to a method provided herein prior to surgery wore a corrective contact lens or corrective glasses (e.g., bifocals), and after surgery and administration of the ophthalmological composition, the individual has less of a need to wear (or can wear a lower power of) the corrective contact lens or corrective glasses (e.g., bifocals).

In some embodiments, provided herein is a method of treating presbyopia in an individual wearing a corrective lens (e.g., contact lens). In some embodiments, provided herein is a method of treating presbyopia in an individual wearing a contact lens. In certain embodiments, the method comprises administering (e.g., topically) one or more drop of an ophthalmic composition comprising aceclidine to an eye (e.g., an ocular surface thereof) of the individual described herein. In specific embodiments, the method comprises removing the contact lens from the eye before administration of an ophthalmological composition provided herein to the eye. In more specific embodiments, the method comprises reinserting the contact lens onto the eye (e.g., about 10 minutes or more) after administration of the ophthalmological composition.

In some embodiments, any ophthalmological composition provided herein comprises an alpha-2 agonist (e.g., brimonidine) or a salt thereof. In some embodiments, any ophthalmological composition provided herein comprises brimonidine or a salt thereof. In some embodiments, the ophthalmological composition comprises (or is formulated with) brimonidine or a salt thereof in a concentration of about 0.05 wt. % to about 0.15 wt. %. In some embodiments, the ophthalmological composition comprises (or is formulated with) brimonidine or a salt thereof in a concentration of 0.07 wt. % to about 0.15 wt. %. In specific embodiments, the ophthalmological composition comprises (or is formulated with) brimonidine or a salt thereof in a concentration of 0.07 wt. % to about 0.1 wt. %. In more specific embodiments, the ophthalmological composition comprises (or is formulated with) brimonidine or a salt thereof in a concentration of about 0.08 wt. %. In some embodiments, the ophthalmological composition is formulated with a brimonidine salt, such as brimonidine tartrate, in an amount of 0.7 wt. % to about 0.1 wt. % (e.g., about 0.08 wt. %). In certain embodiments, the ophthalmological composition comprises brimonidine in an amount of about 0.4 wt. % to about 1 wt. %, such as about 0.5 wt. % to about 0.6 wt. % (e.g., based on free base concentration of brimonidine).

In some embodiments, a composition provided herein comprises aceclidine or a salt thereof and brimonidine or a salt thereof. In some embodiments, a composition provided herein comprises aceclidine hydrochloride in a concentration of about 1.6 wt. % to about 1.8 wt. % and brimonidine tartrate in a concentration of 0.07 wt. % to about 0.15 wt. %. In specific embodiments, a composition provided herein comprises aceclidine hydrochloride in a concentration of about 1.75 wt. % and brimonidine tartrate in a concentration of about 0.08 wt. %.

In some embodiments, a composition provided herein comprises aceclidine in an amount of about 1.4 wt. % to about 1.5 wt. %, such as about 1.44 wt. % to about 1.46 wt. % (e.g., based on free base concentration of aceclidine) and brimonidine in an amount of about 0.4 wt. % to about 1 wt. %, such as about 0.5 wt. % to about 0.6 wt. % (e.g., based on free base concentration of brimonidine).

In some embodiments, an agent (e.g., an active agent such as aceclidine and/or brimonidine) provided herein may comprise one or more of any suitable isotope, such as a hydrogen isotope (e.g., deuterium) and/or a carbon isotope.

In certain embodiments, a composition provided herein has a pH of 6 or less, such as a pH of about 4 to about 6. In some embodiments, the composition has a pH of about 4.5 to about 6. In some embodiments, the composition has a pH of about 4.5 to about 5.5. In some instances, use of a single use container, such as provided herein, in combination with a pH described herein allows the use of aceclidine in an aqueous composition that has good stability, including room temperature (e.g., up to 25° C.) stability.

Provided in certain embodiments herein is an aqueous ophthalmic composition comprising an aceclidine or a salt thereof and a pH of about 4 to about 6 (e.g., about 4.5 to about 5.5). In specific embodiments, the composition comprises a buffer. FIGS. 1A-1D, FIGS. 2A-2D, FIGS. 3A-3D, illustrate stability (% aceclidine relative to initial aceclidine) of an exemplary aqueous aceclidine composition (solution) provided herein when stored at refrigerated (e.g., 2° C. to 8° C.), room temperature (e.g., up to 25° C.), and elevated (up to 40° C.). Specifically, FIG. 1A, FIG. 2A, and FIG. 3A, demonstrate excellent stability for compositions having a pH of 5, in a largely buffer independent manner. Excellent stability is demonstrated at buffer concentrations of 0.06%, 0.08%, and 0.1% (FIG. 1A, FIG. 2A, and FIG. 3A, respectively). All three formulations demonstrate >90% stability for aqueous aceclidine compositions (solutions) when stored for at least 6 months at room temperature and at least 18 months when refrigerated. All three formulations also demonstrate >90% stability when stored for at least 1 month at elevated temperature (40° C.).

Figure 1B:
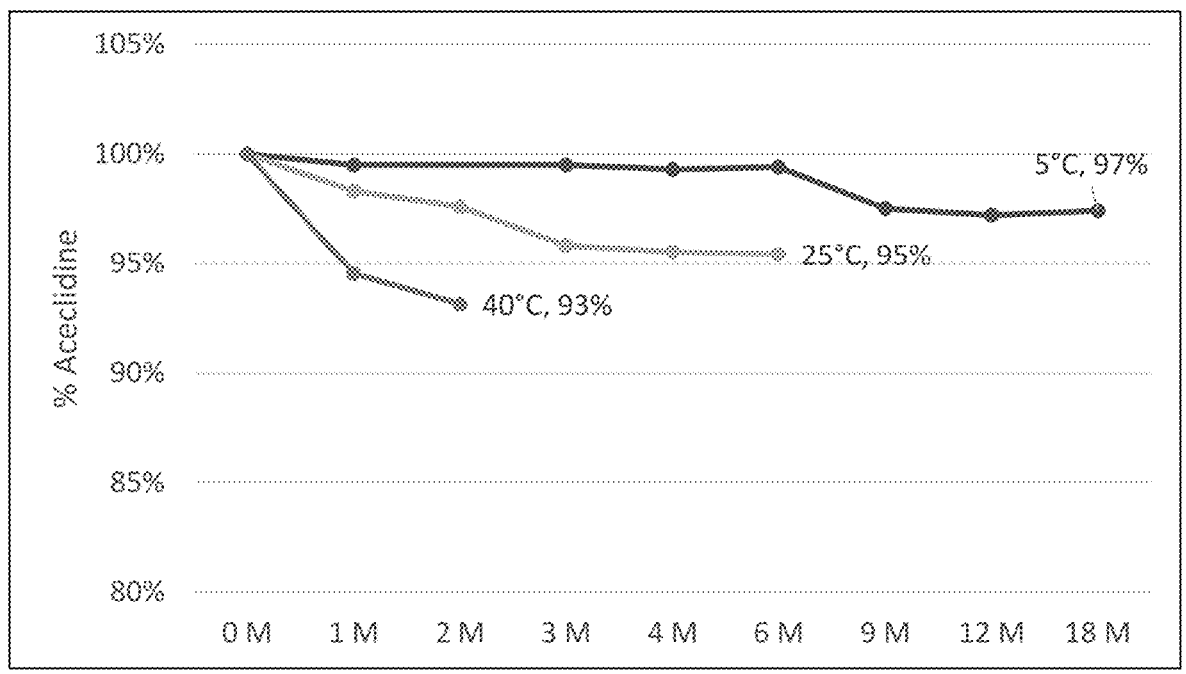
FIG. 1B illustrates the good stability at 0 degrees Celsius (C) to 40° C. for an exemplary aceclidine composition described herein comprising a pH of 5.5.
Figure 2A:
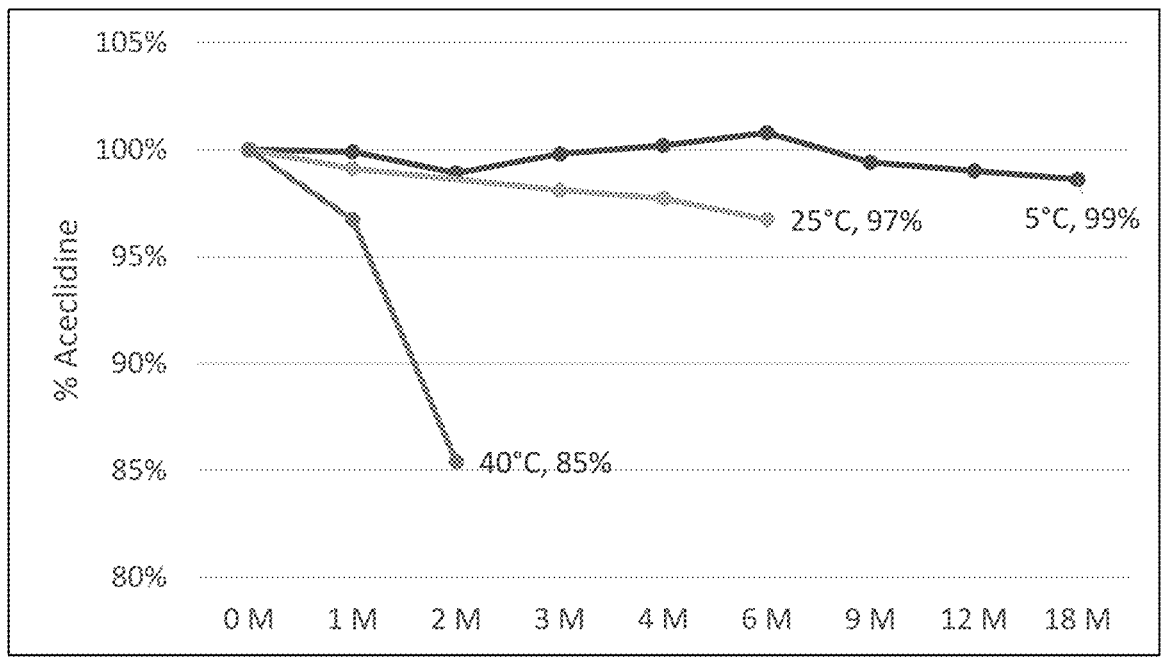
FIG. 2A illustrates the extended stability at temperatures up to 40° C. for an exemplary aceclidine composition described herein comprising a pH of 5.0.
Figure 2B:
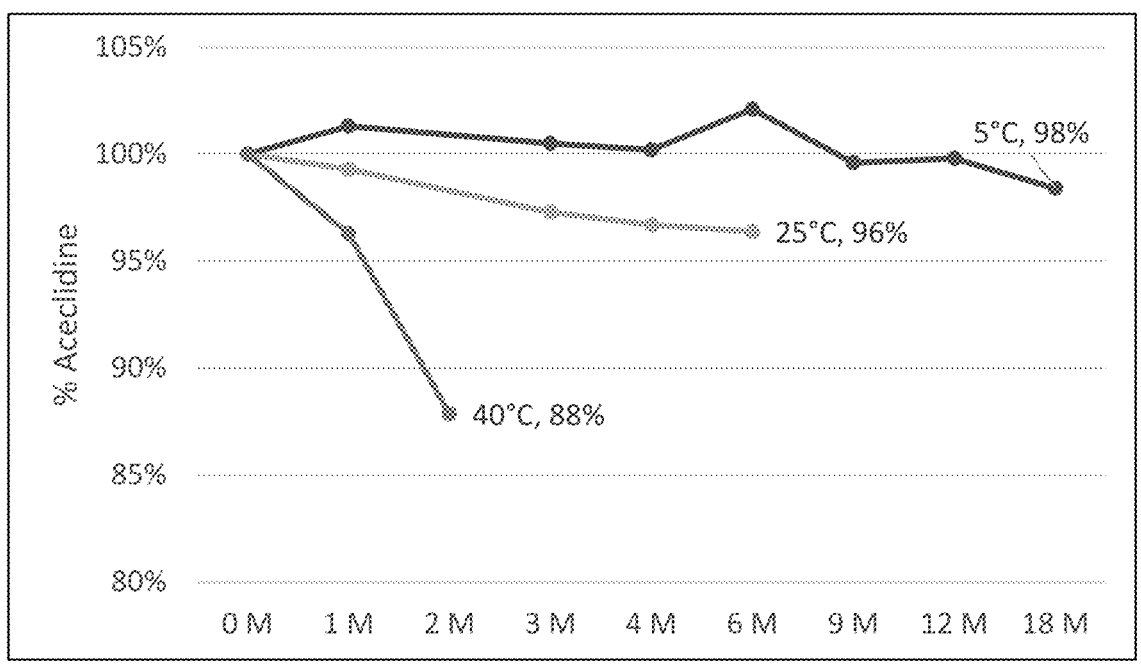
FIG. 2B illustrates the extended stability at temperatures up to 40° C. for an exemplary aceclidine composition described herein comprising a pH of 5.5.
Figure 3A:
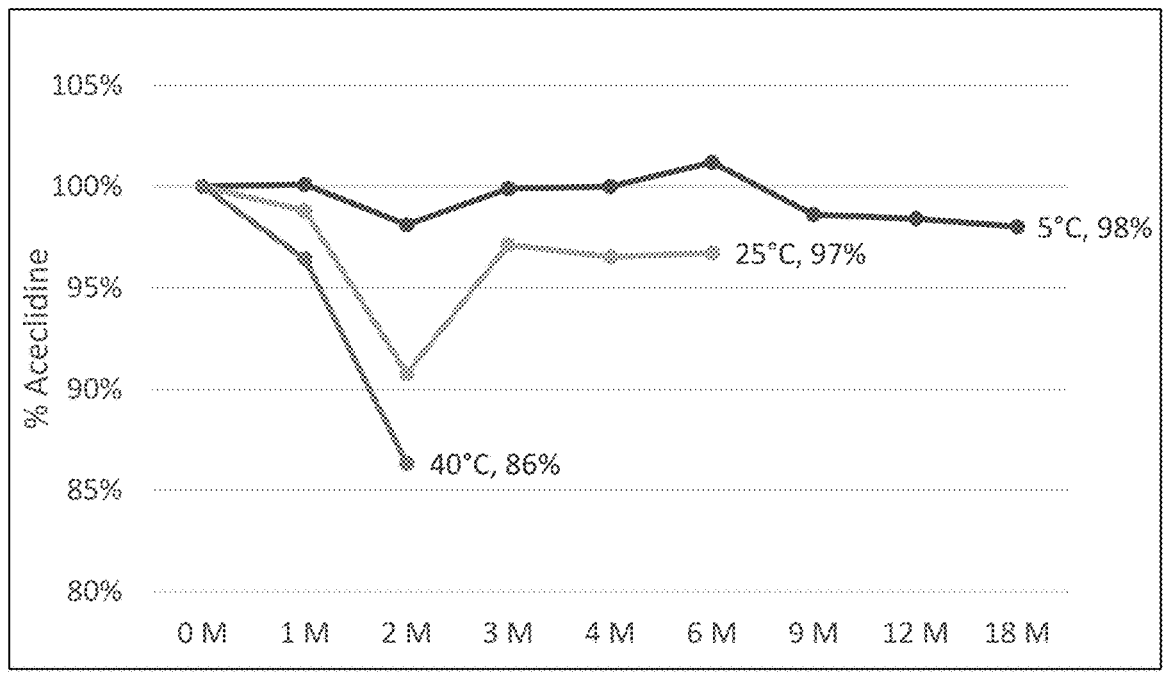
FIG. 3A illustrates the extended stability at temperatures up to 40° C. for an exemplary aceclidine composition described herein comprising a pH of 5.0.
Figure 3B:
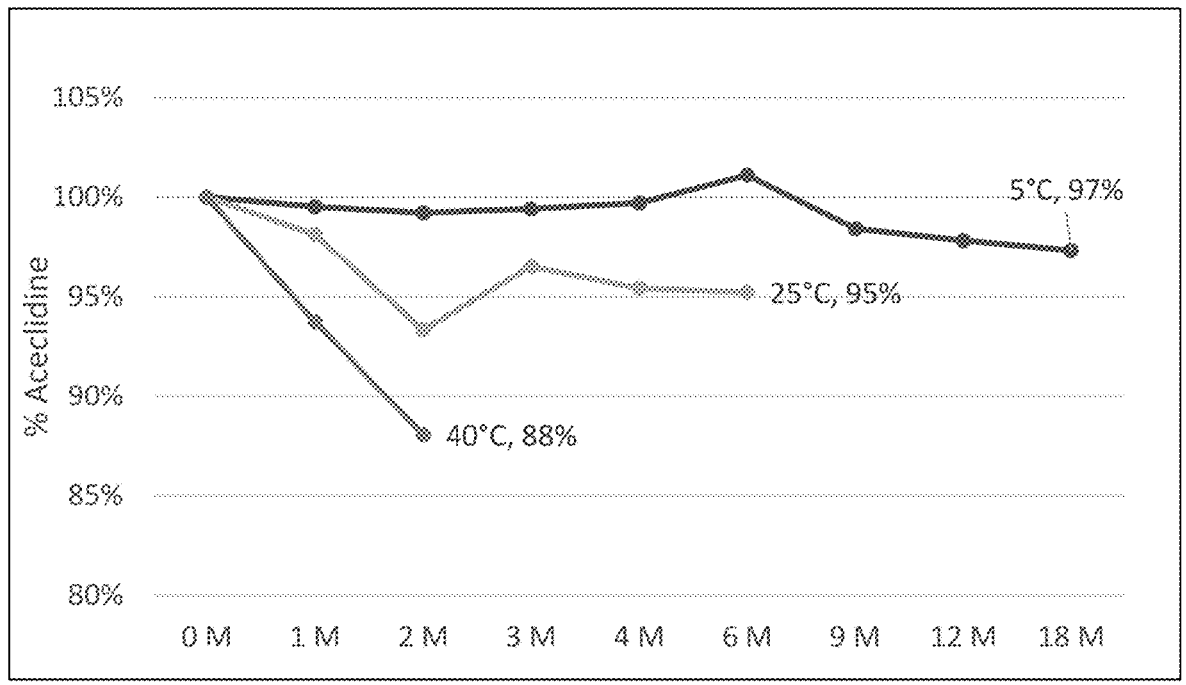
FIG. 3B illustrates the extended stability at temperatures up to 40° C. for an exemplary aceclidine composition described herein comprising a pH of 5.5.

Similarly, FIG. 1B, FIG. 2B, and FIG. 3B, demonstrate excellent stability for compositions having a pH of 5.5, in a largely buffer independent manner. Excellent stability is demonstrated at buffer concentrations of 0.06%, 0.08%, and 0.1% (FIG. 1B, FIG. 2B, and FIG. 3B, respectively). All three formulations demonstrate >90% stability for aqueous aceclidine compositions (solutions) when stored for at least 6 months at room temperature and at least 18 months when refrigerated. All three formulations also demonstrate >90% stability when stored for at least 1 month at elevated temperature (40° C.).

Figure 1C:
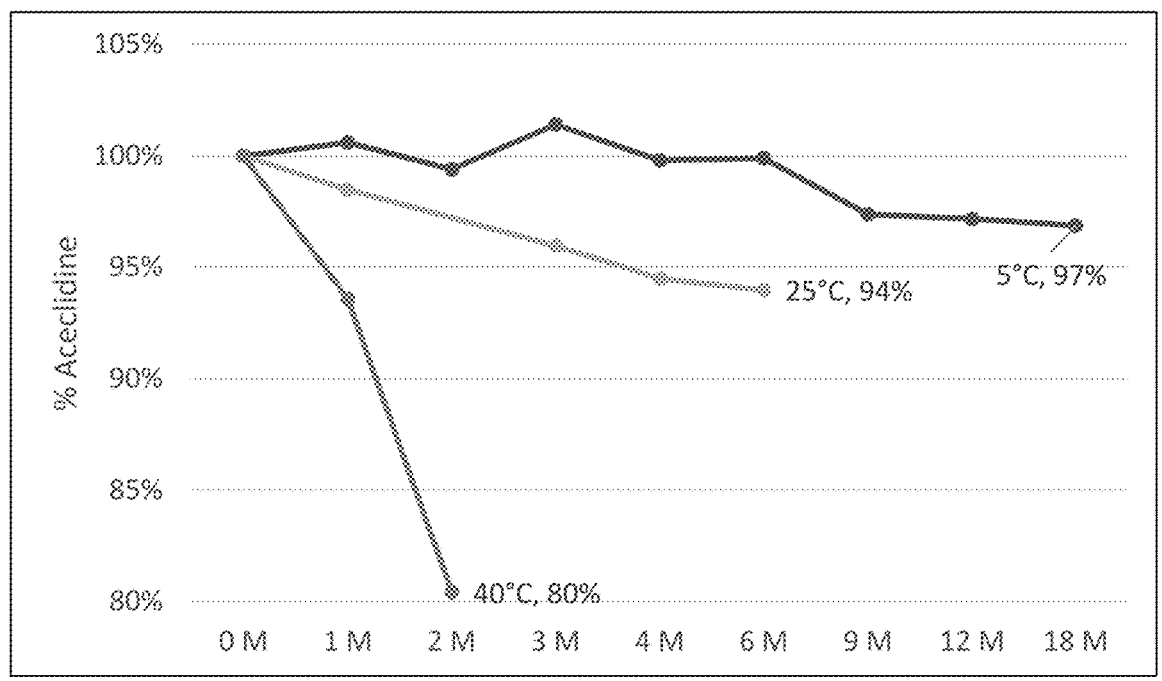
FIG. 1C illustrates the good stability at temperatures up to 40° C. for an exemplary aceclidine composition described herein comprising a pH of 6.0.
Figure 2C:
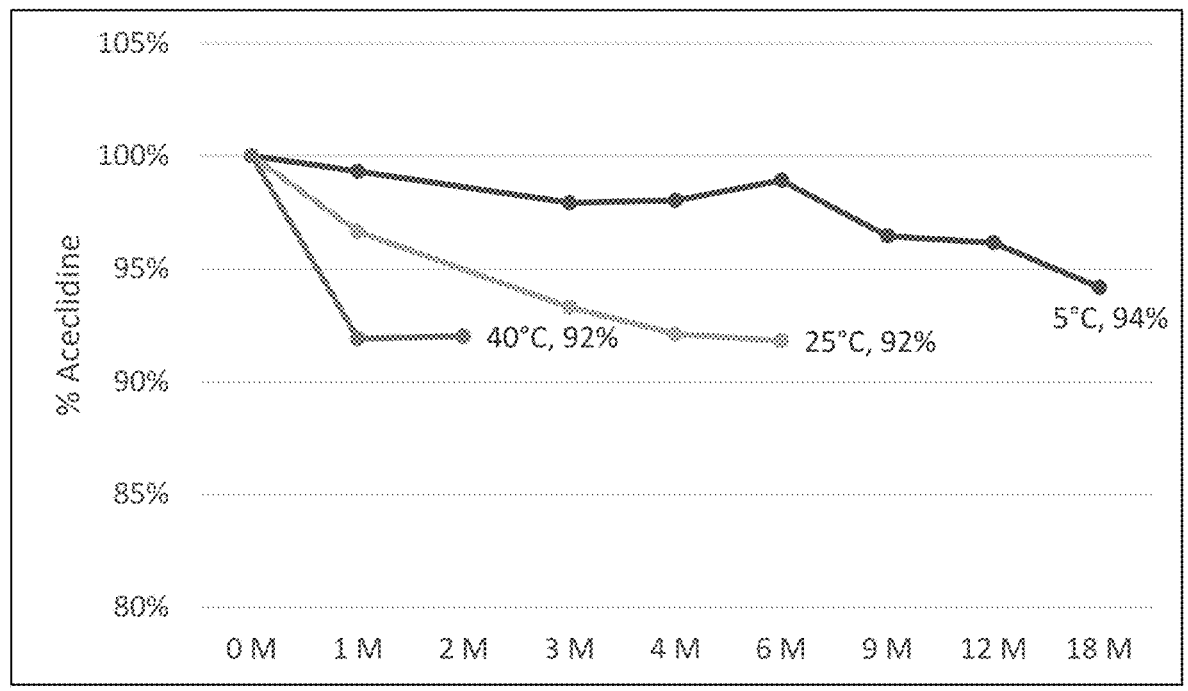
FIG. 2C illustrates the good stability at temperatures up to 40° C. for an exemplary aceclidine composition described herein comprising a pH of 6.0.
Figure 3C:
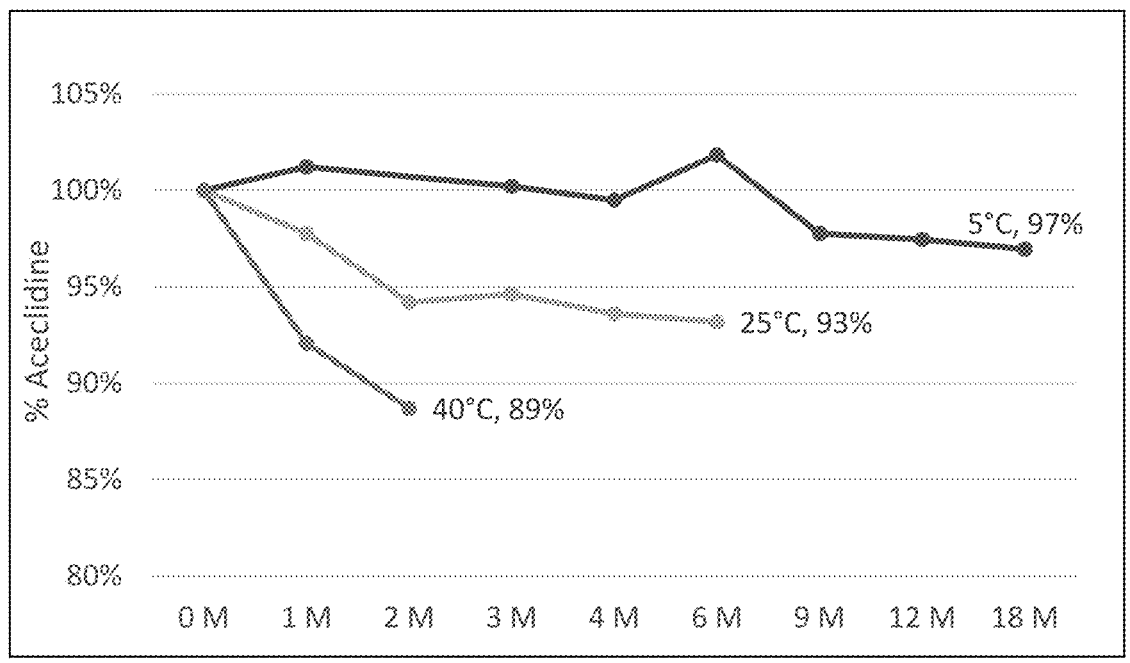
FIG. 3C illustrates the good stability at temperatures up to 40° C. for an exemplary aceclidine composition described herein comprising a pH of 6.0.

FIG. 1C, FIG. 2C, and FIG. 3C, demonstrate good stability (slightly less than at pH of 5 or 5.5) for compositions having a pH of 6, in a largely buffer independent manner. Good stability is demonstrated at buffer concentrations of 0.06%, 0.08%, and 0.1% (FIG. 1C, FIG. 2C, and FIG. 3C, respectively). All three formulations demonstrate >90% stability for aqueous aceclidine compositions (solutions) when stored for at least 6 months at room temperature and at least 18 months when refrigerated. All three formulations also demonstrate >90% stability when stored for at least 1 month at elevated temperature (40° C.).

Figure 1D:
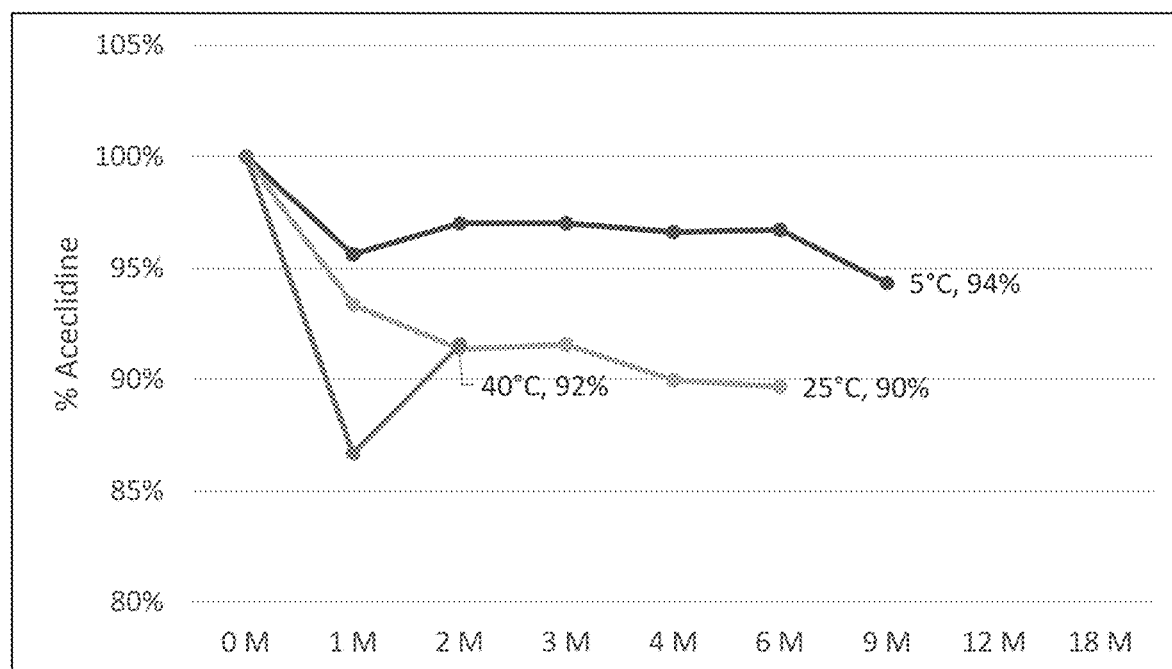
FIG. 1D illustrates the stability at temperatures up to 40° C. for an exemplary aceclidine composition described herein comprising a pH of 6.5.
Figure 2D:
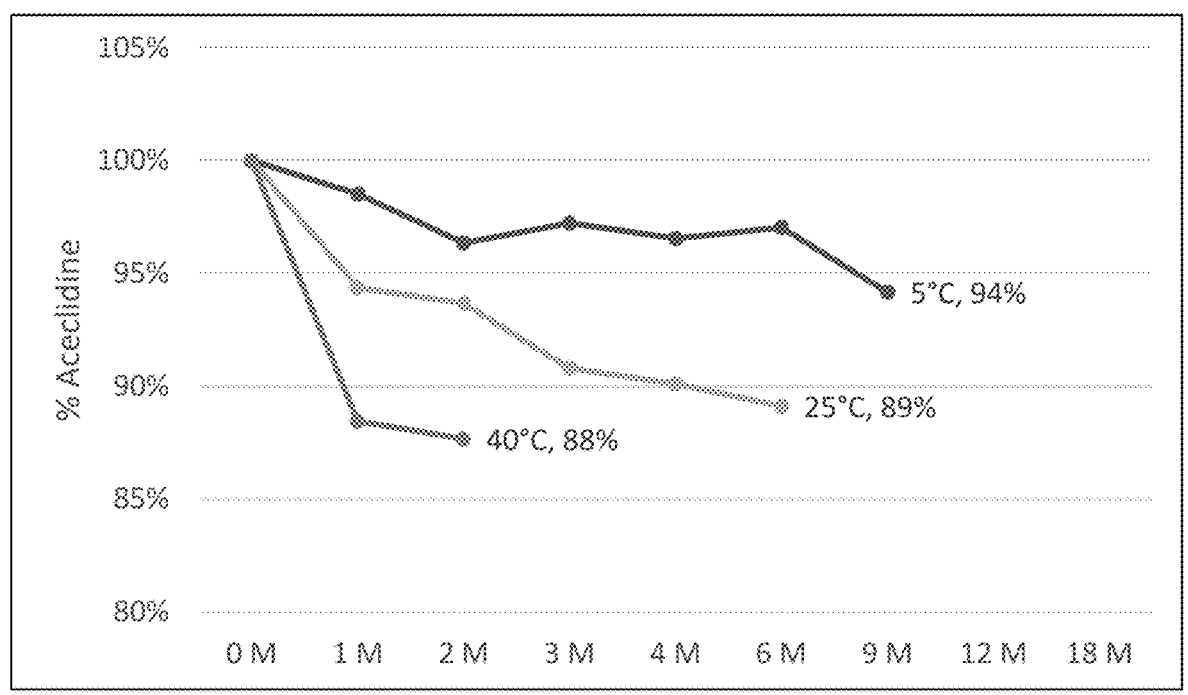
FIG. 2D illustrates the stability at temperatures up to 40° C. for an exemplary aceclidine composition described herein comprising a pH of 6.5.
Figure 3D:
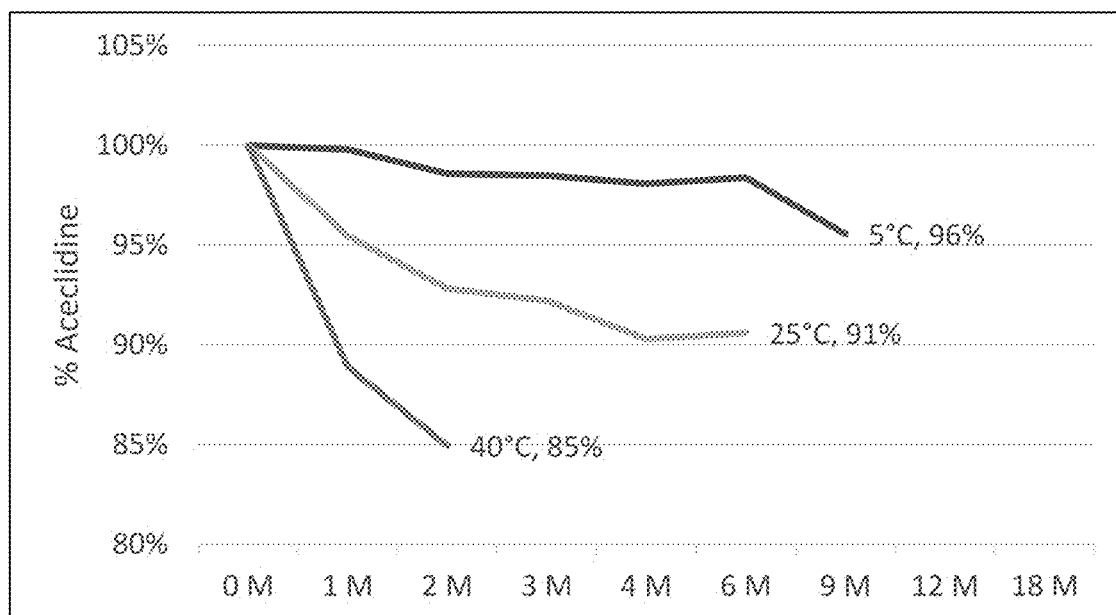
FIG. 3D illustrates the stability at temperatures up to 40° C. for an exemplary aceclidine composition described herein comprising a pH of 6.5.

FIG. 1D, FIG. 2D, and FIG. 3D, demonstrate reduced stability (relative to pH of 5, 5.5, or 6) for compositions having a pH of 6.5, in a largely buffer independent manner. Stability is demonstrated at buffer concentrations of 0.06%, 0.08%, and 0.1% (FIG. 1D, FIG. 2D, and FIG. 3D, respectively). All three formulations demonstrate approximately 90% stability or less for aqueous aceclidine compositions (solutions) when stored for 6 months at room temperature. All three formulations also demonstrate <90% stability when stored for at least 1 month at elevated temperature (40° C.).

Figure 4A:
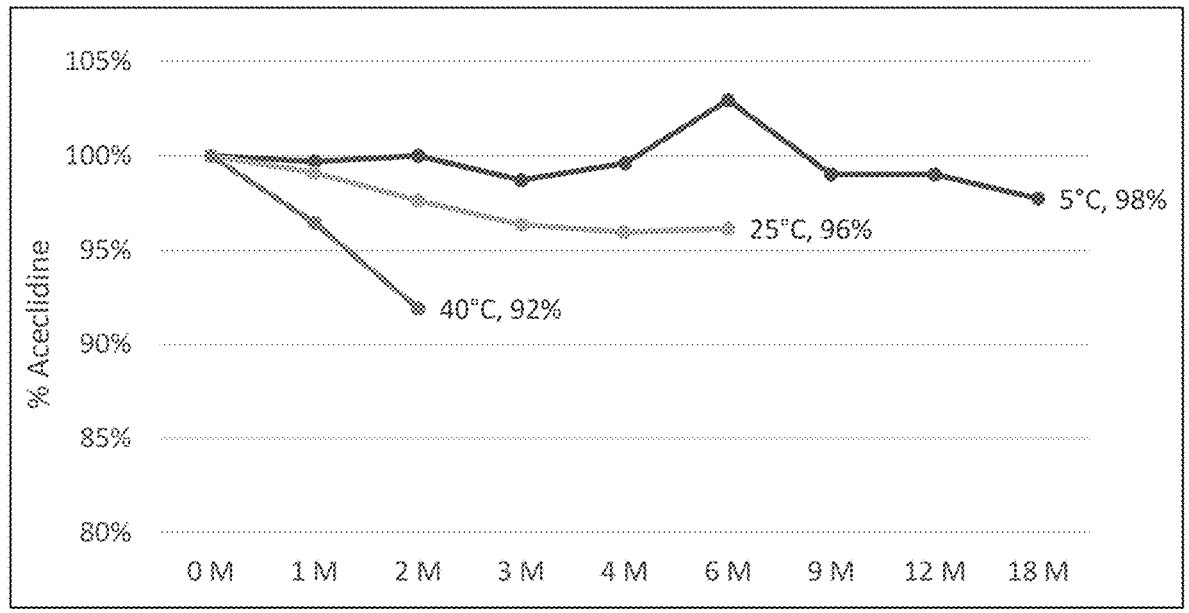
FIG. 4A illustrates the extended stability at temperatures up to 40° C. for an exemplary aceclidine composition described herein comprising a preservative.
Figure 4B:
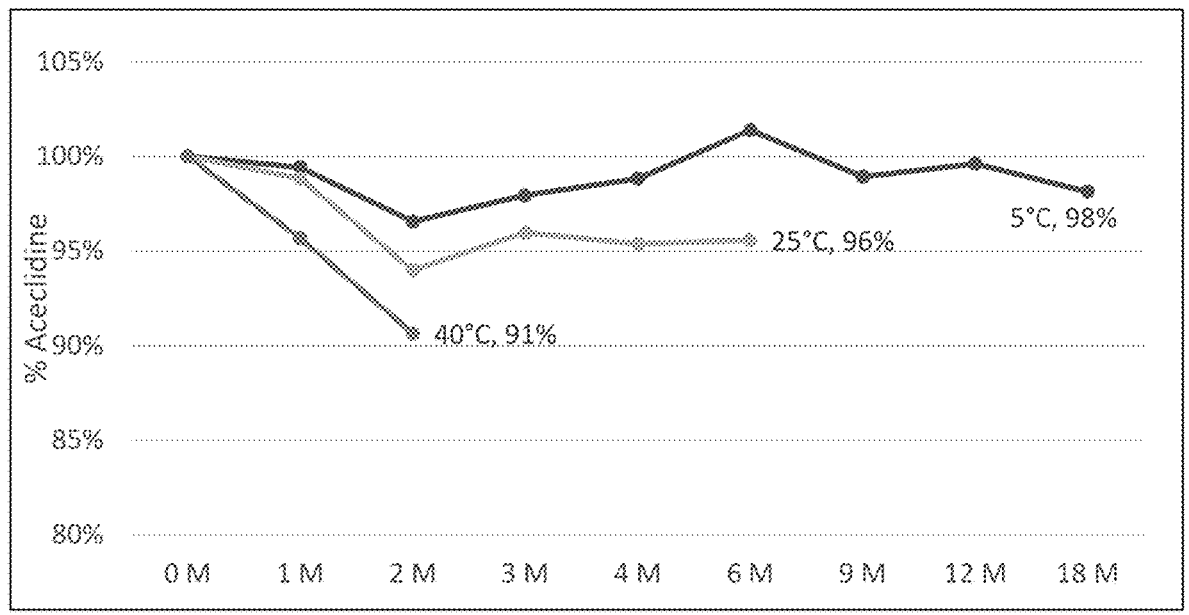
FIG. 4B illustrates the extended stability at temperatures up to 40° C. for an exemplary preservative-free aceclidine composition described herein.

Moreover, FIG. 4A and FIG. 4B demonstrate excellent stability in such aqueous aceclidine compositions (solutions) in a substantially preservative independent manner. Similarly, FIG. 4C, FIG. 4D, and FIG. 4E demonstrate excellent stability in such aqueous aceclidine compositions (solutions) in a substantially viscosity agent (HPMC) independent manner. Surprisingly, varying certain components, such as buffer concentration or adding a preservative, was not observed to substantially no effect on aceclidine stability of aceclidine compositions described herein.

In some instances, compositions provided herein (e.g., comprising aceclidine and a pH of 4.5 to 6) have stability profiles that are acceptable for manufacture, shipment, and/or (e.g., long-term) storage of aceclidine.

In some embodiments, composition comprises or is formulated with salt (e.g., NaCl), an acid (e.g., HCl), and/or a base (e.g., NaOH), such as to adjust osmolarity or pH.

In some embodiments, any suitable salt can be used in an agent (e.g., aceclidine and brimonidine) provided herein. In some embodiments, the salt is a hydrochloride, hydrobromide, sulfate, acetate, phosphate or diphosphate, chloride, bromide, maleate, citrate, mesylate, nitrate, tartrate, or gluconate.

In some instances, a system provided herein allows for the room temperature (e.g., up to 25° C.) storage (e.g., by an end user) for (e.g., up to) 3 months. In specific instances, a system provided herein allows for the room temperature (e.g., up to 25° C.) storage (e.g., by an end user) for (e.g., up to) 6 months.

In some embodiments, a composition provided herein comprises a buffer, such as any suitable buffer (e.g., a buffer suitable for ophthalmic use). In certain embodiments, the buffer is a citrate, such as sodium citrate, or an acetate, such as sodium acetate. In another embodiment, the buffer is a phosphate, Tris, or borate buffer. In certain embodiments, a composition provided herein comprises a buffer, such as in any suitable concentration (e.g., a concentration suitable for providing a pH provided herein).

In certain embodiments, a composition provided herein comprises citrate or a salt thereof (e.g., sodium citrate) or acetate or a salt thereof (e.g., sodium acetate) in a concentration of about 0.01% to about 1% (e.g., about 0.05% to about 0.2%). In specific embodiments, a composition provided herein comprises citrate or a salt thereof (e.g., sodium citrate) in a concentration of about 0.01% to about 0.1% (e.g., about 0.05% to about 0.08%). In some embodiments, a buffering agent is present or formulated into the ophthalmological composition provided herein is in a concentration of about 0.05 wt. % to about 0.15 wt. % (e.g., formulated with sodium citrate at a concentration of about 0.08 wt. %).

In some embodiments, a composition described herein comprises an ophthalmological drug. In some embodiments, the ophthalmological drug is aceclidine or a salt thereof.

In some embodiments, a composition described herein comprises an ophthalmological drug and a viscosity agent.

In some embodiments, a composition described herein comprises an ophthalmological drug and a surfactant.

In some embodiments, a composition described herein comprises an ophthalmological drug and a buffer.

In some embodiments, a composition described herein comprises an ophthalmological drug and tonicity agent.

In some embodiments, a composition described herein comprises an ophthalmological drug and an antioxidant.

In some embodiments, a composition described herein comprises an ophthalmological drug, a viscosity agent, and a surfactant.

In some embodiments, a composition described herein comprises an ophthalmological drug, a viscosity agent, a surfactant, and a buffer.

In some embodiments, a composition described herein comprises an ophthalmological drug, a viscosity agent, a surfactant, and a tonicity agent.

In some embodiments, a composition described herein comprises an ophthalmological drug, a viscosity agent, a surfactant, a buffer, and a tonicity agent.

In some embodiments, a composition described herein comprises an ophthalmological drug, a viscosity agent, a surfactant, a buffer, a tonicity agent, and an antioxidant.

In some embodiments, a composition provided herein comprises a viscosity agent, such as any suitable viscosity agent. In some instances, a viscosity agent (e.g., a viscosity enhancing agent or thickening agent, which terms are used interchangeably herein) enhances permeation of an ophthalmological drug described herein into an eye (e.g., cornea) of an individual described herein. In some instances, a viscosity agent (e.g., a viscosity enhancing agent) increases the residence time of an ophthalmological drug described herein on an eye of an individual described herein. In some embodiments, an ophthalmological composition provided herein is an eye drop (e.g., slightly viscous ophthalmic solution).

In some embodiments, the composition further comprises a viscosity agent described herein (e.g., a cellulose derivative), such as at a concentration described herein. In some embodiments, a viscosity agent provided herein is guar gum, hydroxypropyl-guar ("hp-guar"), xanthan gum, alginate, chitosan, gelrite, hyaluronic acid, dextran, Carbopol® (polyacrylic acid or carbomer) including Carbopol® 900 series including Carbopol® 940 (carbomer 940), Carbopol® 910 (carbomer 910) and Carbopol® 934 (carbomer 934), cellulose derivatives such as high molecular weight carboxymethyl cellulose ("CMC"), methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxypropylethyl cellulose, and hydroxyethyl cellulose, polyethylene glycol, polyvinyl alcohol, polyvinyl chloride, polyvinyl pyrrolidone, gellan, carrageenan, alginic acid, carboxyvinyl polymer or combinations thereof. In certain embodiments, a viscosity agent is a cellulose derivative. In some embodiments, a viscosity agent is a high molecular weight carboxymethyl cellulose (CMC). In some embodiments, a viscosity agent is methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxypropylethyl cellulose, hydroxyethyl cellulose, or a combination thereof. In some embodiments, a viscosity agent is hydroxypropylmethyl cellulose (HPMC).

In some embodiments, a composition described herein comprises any suitable concentration of a viscosity agent. In some embodiments, the concentration of a viscosity agent in a composition described herein is about 5 wt. %, or less. In some embodiments, the concentration of a viscosity agent in a composition described herein is about 0.01 wt. % to about 5 wt. %. In some embodiments, the concentration of a viscosity agent in a composition described herein is about 0.1 wt. % to about 4 wt. %. In some embodiments, the concentration of a viscosity agent in a composition described herein is about 0.5 wt. % to about 2 wt. %. In some embodiments, the concentration of a viscosity agent in a composition described herein is about 1 wt. % to about 2 wt. %. In some embodiments, the concentration of a viscosity agent in a composition described herein is about 1 wt. % to about 1.5 wt. % (e.g., about 1.25 wt. %).

In some embodiments, the composition provided herein, such as enclosed in a chamber of a container (e.g., of a system) provided herein, has any suitable viscosity. In certain embodiments, the composition has relatively high viscosity at low shear (e.g., 0 or 1 per second shear rate), such as to inhibit degradation of active ingredients and/or to improve residence time on an ocular surface upon installation.

In some embodiments, the composition provided herein, such as enclosed in a chamber of a container (e.g., of a system) provided herein, has a viscosity at low shear (e.g., 0 or 1 per second shear rate) of at least 50 centipoise (cP). In specific embodiments, the viscosity of low shear is about 100 to about 1,000 cP. In more specific embodiments, the viscosity of low shear is about 200 to about 500 cP. In still more specific embodiments, the viscosity of low shear is about 300 to about 400 cP. In certain embodiments, any viscosity agent, such as a viscosity agent provided herein, is included in the composition in an amount sufficient to provide a desired viscosity (e.g., at low shear), such as a viscosity described herein.

In some embodiments, the composition provided herein, such as enclosed in a chamber of a container (e.g., of a system) provided herein, has a viscosity of at least 500 centipoise (cP). In specific embodiments, the viscosity is about 500 to about 1,500 cP. In more specific embodiments, the viscosity is about 600 to about 1,200 cP. In still more specific embodiments, the viscosity is about 750 to about 1000 cP. In some embodiments, the viscosity is about 800 to about 900 cP. In some instances, the viscosity is measured at 20 degrees Celsius+0.1 degrees Celsius, such as at 12 rpm. In some instances, protocols for determining viscosity are set forth in the examples provided herein.

In some embodiments, the composition further comprises a surfactant (e.g., a nonionic surfactant), such as at a concentration described herein. In some embodiments, the surfactant is alpha cyclodextrin, beta cyclodextrin, or gamma cyclodextrin. In some embodiments, a beta cyclodextrin is 2-hydroxypropyl beta-cyclodextrin ("HPBCD"). In some embodiments, a beta cyclodextrin is sulfobutyl ether derivative of β-cyclodextrin (Captisol®). In some embodiments, a surfactant is a polyoxyl alkyl. In some embodiments, a surfactant is polyoxyl 40 stearate or polyoxyl 35 castor oil. In some embodiments, a surfactant is a poloxamer. In some embodiments, a surfactant is poloxamer 108 or poloxamer 407. In some embodiments, a surfactant is a polysorbate. In some embodiments, a surfactant is polysorbate 80 or Brij® 35 (Brij is a registered trademark of Uniqema Americas LLC). In some embodiments, a surfactant is polysorbate 80. In some embodiments, a surfactant is a polysorbate, a tyloxapol, a poloxamer, a cyclodextrin, vitamin E TPGS, a polyoxyl castor oil, a polyoxyl stearate, polyethylene glycol, a polyoxyethylene glycol alkyl ether or 2-[[10,13-dimethyl-17-(6-methylheptan-2-yl)-2,3,4,7,8,9, 11,12,14,15,16,17-dodecahydro-1H-cyclopenta[a] phenanthren-3-yl]oxy]ethanol. In some embodiments, a surfactant is Poloxamer 80, Poloxamer 188, Poloxamer 407, Polysorbate 20, Polysorbate 80, ionically charged (e.g., anionic) beta-cyclodextrins with or without a butyrated salt (Captisol®) 2-hydroxypropyl beta cyclodextrin ("HPBCD"), alpha cyclodextrins, gamma cyclodextrins, Polyoxyl 35 castor oil, and Polyoxyl 40 hydrogenated castor oil or combinations thereof.

In some embodiments, a composition described herein comprises any suitable concentration of a surfactant. In some embodiments, the concentration of a surfactant in a composition described herein is about 15 wt. %, or less. In some embodiments, the concentration of a surfactant in a composition described herein is about 0.1 wt. % to about 15 wt. %. In some embodiments, the concentration of a surfactant in a composition described herein is about 1 wt. % to about 10 wt. %. In some embodiments, the concentration of a surfactant in a composition described herein is about 1 wt. % to about 5 wt. %. In some embodiments, the concentration of a surfactant in a composition described herein is about 2 wt. % to about 5 wt. %. In some embodiments, the concentration of a surfactant in a composition described herein is about 3 wt. % to about 5 wt. %.

In some instances, a surfactant provided herein (e.g., polysorbate 80) functions in a composition described herein as a lubricant when administered to an ocular surface such as to relieve burning, irritation, or discomfort in the eye/ocular surface.

In some embodiments, an ophthalmological composition provided herein comprises a lubricant. In some embodiments, the lubricant is a surfactant provided herein. In some embodiments, the concentration of a lubricant provided herein is about 3 wt. % to about 5 wt. % (e.g., about 4 wt. %).

In some embodiments, an ophthalmological composition provided herein comprises a chelating agent. In some embodiments, the chelating agent is edetate (e.g., formulated with edetate disodium dihydrate). In some embodiments, the concentration of a chelating agent provided herein is about 0.05 wt. % to about 0.2 wt. % (e.g., formulated with edetate disodium dihydrate at a concentration of about 0.1 wt. %).

In some embodiments, a composition described herein comprises a tonicity agent. In some embodiments, composition described herein comprises any suitable tonicity agent. In some instances, a tonicity agent reduces irritation on the eye of an individual when applied to the eye. In some instances, a tonicity agent reduces irritation at the application site (e.g., eye) by preventing or reducing osmotic shock. Osmotic shock may occur at the application site upon a sudden change in salt concentration. In some embodiments, a composition described herein comprising a tonicity agent reduces or prevents osmotic shock at the application site relative to an otherwise similar composition not comprising a tonicity agent.

In some embodiments, a composition provided herein comprises any suitable tonicity agent. In specific embodiments, the tonicity agent is a polyol or salt. In some embodiments, a tonicity agent is a polyol. In some embodiments, a polyol is two or more hydroxyl groups. In some embodiments, a polyol is glycerin, pentaerythritol, ethylene glycol, sucrose, dextrose, glucose, mannitol, glycerol, erythritol, lactitol, xylitol, sorbitol, isosorbide, propylene glycol, maltitol, threitol, arabitol, ribitol, or a combination thereof. In some embodiments, a tonicity agent is mannitol. In some embodiments, a tonicity agent is glycerin. In some embodiments, a tonicity agent is dextrose. In some embodiments, a tonicity agent is a salt. In some embodiments, a tonicity agent is sodium chloride or potassium chloride. In some embodiments, a composition described herein comprises any suitable concentration of a tonicity agent. In some embodiments, the concentration of a tonicity agent in a composition described herein is about 5 wt. %, or less. In some embodiments, the concentration of a tonicity agent in a composition described herein is about 4 wt. %, or less. In some embodiments, the concentration of a tonicity agent in a composition described herein is about 0.01 wt. % to about 4 wt. %. In some embodiments, the concentration of a tonicity agent in a composition described herein is about 1 wt. % to about 4 wt. %. In some embodiments, the concentration of a tonicity agent in a composition described herein is about 2 wt. % to about 3 wt. % (e.g., about 2.5 wt. %).

In some embodiments, a composition provided herein preservative-free. In certain embodiments, a composition provided herein is free of benzalkonium chloride (BAK).

In certain embodiments, the system and/or container and/or composition is sterile. In some instances, use of a single use container, such as described herein, allows for the use of a preservative free composition. In addition, efficacious use of a two-drop dose, wherein the two drops are administered in a short time period (e.g., only 2 minutes versus 5 minutes or more) allows for the use of a single container that may be used to administer two drops to a single eye or four drops to two eyes of an individual. In some instances, if longer periods of time were used, there could be a higher chance of spillage, which may be result in insufficient volume of composition for appropriate dosing. It is surprising that use of two drop administration within 2 minutes facilitates long term efficacious use (e.g., relative to a single drop dose) and it is surprising that such a short time period may facilitate extended duration of efficacy (e.g., and that a longer delay, such as 5 minutes or more is not required).

In some embodiments, a composition provided herein is clear and colorless. In some instances, it is surprising that a composition comprising the components such as described herein is clear and colorless. In certain embodiments, such characteristics are important for commercial use so that end users can readily determine whether or not a composition may be suitable for use. free.

In some embodiments, provided herein is a method for treating presbyopia in an individual (e.g., in need thereof). In specific embodiments, the method comprises administering to the individual (e.g., at least one eye thereof) a (e.g., ophthalmological) composition, such as any composition described herein. In some embodiments, the method comprises providing a system or container provided herein, such as wherein the method comprises opening a container (e.g., of a system) provided herein.

In certain embodiments, a method provided herein comprises opening a (e.g., single use) container, such as a container provided herein. In specific embodiments, opening the container provides an opening in the container. In some embodiments, the opening provides access to an enclosure of the container. In some embodiments, a composition provided herein is configured within the container.

In some embodiments, a method provided herein comprises administering to an (e.g., eye of the) individual a drop of a composition from the container (e.g., wherein the composition is configured within the container, such as an enclosure thereof), such as through an opening of the container. In certain embodiments, the method further comprises administering to (e.g., an eye of the) individual a second drop of a composition from the container. In specific embodiments, the second drop is administered 30 seconds to 4 minutes (or less than 5 minutes) after the first drop. In more specific embodiments, the second drop is administered 1 to 3 minutes after the first drop. In still more specific embodiments, the second drop is administered about 2 minutes after the first drop.

In certain embodiments, a method provided herein comprising administering a first and a second drop of a composition (e.g., from a container provided herein) to a first eye of an individual and a third and a fourth drop of a composition (e.g., from a container provided herein) to a second eye of an individual. In specific embodiments, the first, second, third, and fourth drops are all administered from a single container. In some embodiments, the second drop is administered 30 seconds to 4 minutes (or less than 5 minutes) after the first drop. In more specific embodiments, the second drop is administered 1 to 3 minutes after the first drop. In still more specific embodiments, the second drop is administered about 2 minutes after the first drop. In certain embodiments, the fourth drop is administered 30 seconds to 4 minutes (or less than 5 minutes) after the third drop. In more specific embodiments, the fourth drop is administered 1 to 3 minutes after the third drop. In still more specific embodiments, the fourth drop is administered about 2 minutes after the third drop. In certain embodiments, the first and third drop are administered prior to the second and third drop. In some embodiments, the third drop is administered immediately (within 30 seconds) following administration of the first drop. In certain embodiments, the fourth drop is administered immediately (within 30 seconds) following administration of the second drop.

In some embodiments, additional compositions are similarly administered on subsequent days. For example, in certain embodiments, a second system is provided, with a second container being opened and drops administered to the eye(s) of the individual on a second day. In some embodiments, a third system is provided, with a third container being opened and drops administered to the eye(s) of the individual on a third day. In certain embodiments, additional containers are similarly used. In some embodiments, a kit is provided comprising two or more such containers and packaging material enclosing the two or more containers prior to use. In certain embodiments, three or more containers are provided in the kit. In specific embodiments, five containers are provided in the kit (e.g., to facilitate business weekday use of the compositions/systems).

In some embodiments, provided herein is a kit comprising at least two similar or identical systems and a package (e.g., housing the two or more systems). In some embodiments, the two similar or identical systems each comprise a separate container and separate but identical compositions, such as wherein the composition is (or the compositions are) any composition described herein. In certain instances, the containers of the kit are optionally connected to one another prior to use, such as in a manner whereby a container can be detached from the other containers prior to use (e.g., prior to opening and dispensing a composition therefrom).

In certain embodiments, a method provided comprises storing a composition (e.g., the system and container enclosing the composition) at room temperature (e.g., up to 25° C.) prior to use. In some embodiments, a method provided herein comprising using a composition (e.g., the system and container enclosing the composition) that has been stored at room temperature (e.g., up to 25° C.) prior to use. In certain embodiments, the composition is or has been stored for (e.g., up to) 3 months at room temperature (e.g., up to 25° C.). In certain embodiments, the composition is or has been stored for (e.g., up to) 6 months at room temperature (e.g., up to 25° C.). In some instances, a composition comprises at least 90% of the initial amount (e.g., upon initial formulation or immediately prior to room temperature storage) of aceclidine in the composition upon administration (e.g., after storing at room temperature as described herein). In specific instances, room temperature is a temperature above refrigerated temperature (e.g., about 8° C.).

In certain embodiments, a method provided comprises storing a composition (e.g., the system and container enclosing the composition) at refrigerated temperature (e.g., about 2° C. to about 8° C.) prior to use. In some embodiments, a method provided herein comprising using a composition (e.g., the system and container enclosing the composition) that has been stored at refrigerated temperature (e.g., about 2° C. to about 8° C.) prior to use. In certain embodiments, the composition is or has been stored for (e.g., up to) 12 months at refrigerated temperature (e.g., about 2° C. to about 8° C.) prior to use. In certain embodiments, the composition is or has been stored for (e.g., up to) 18 months at refrigerated temperature (e.g., about 2° C. to about 8° C.) prior to use. In some instances, a composition comprises at least 95% of the initial amount (e.g., upon initial formulation or immediately prior to room temperature storage) of aceclidine in the composition upon initial administration or after storing at refrigerated temperature, such as described herein. In some instances, a composition comprises at least 90% of the initial amount (e.g., upon initial formulation) of aceclidine in the composition upon administration (e.g., after storing at refrigerated and room temperature, such as described herein).

In certain embodiments, a composition provided herein has been stored at a temperature from about 0 degrees Celsius to about 10 degrees Celsius, such as for up to 24 months. In certain embodiments, a composition provided herein has been stored at a temperature from about 2 degrees Celsius to about 8 degrees Celsius, such as for up to 24 months.

In certain embodiments, a composition provided herein has been stored at a temperature from about 0 degrees Celsius to about 10 degrees Celsius, such as for up to 12-18 months. In certain embodiments, a composition provided herein has been stored at a temperature from about 2 degrees Celsius to about 8 degrees Celsius, such as for up to 12-18 months.

In certain embodiments, a composition provided herein has been stored up to 24 months (e.g., at 2 degrees Celsius to 8 degrees Celsius). In certain embodiments, a composition provided herein comprises at least 90 wt. % of the initial amount (e.g., the amount of aceclidine in the composition prior to such storage) of aceclidine after storage for 24 months (e.g., at 2 degrees Celsius to 8 degrees Celsius). In certain embodiments, a composition provided herein comprises at least 95 wt. % of the initial amount (e.g., the amount of aceclidine in the composition prior to such storage) of aceclidine after storage for 24 months (e.g., at 2 degrees Celsius to 8 degrees Celsius).

In certain embodiments, a composition provided herein has been stored up to 18 months (e.g., at 2 degrees Celsius to 8 degrees Celsius). In certain embodiments, a composition provided herein comprises at least 90 wt. % of the initial amount (e.g., the amount of aceclidine in the composition prior to such storage) of aceclidine after storage for 18 months (e.g., at 2 degrees Celsius to 8 degrees Celsius). In certain embodiments, a composition provided herein comprises at least 95 wt. % of the initial amount (e.g., the amount of aceclidine in the composition prior to such storage) of aceclidine after storage for 18 months (e.g., at 2 degrees Celsius to 8 degrees Celsius).

In certain embodiments, a composition provided herein has been stored up to 12 months (e.g., at 2 degrees Celsius to 8 degrees Celsius). In certain embodiments, a composition provided herein comprises at least 90 wt. % of the initial amount (e.g., the amount of aceclidine in the composition prior to such storage) of aceclidine after storage for 12 months (e.g., at 2 degrees Celsius to 8 degrees Celsius). In certain embodiments, a composition provided herein comprises at least 95 wt. % of the initial amount (e.g., the amount of aceclidine in the composition prior to such storage) of aceclidine after storage for 12 months (e.g., at 2 degrees Celsius to 8 degrees Celsius).

In certain embodiments, a composition provided herein has been stored up to 6 months (e.g., at room temperature, such as up to 25 degrees Celsius). In certain embodiments, a composition provided herein comprises at least 90 wt. % of the initial amount (e.g., the amount of aceclidine in the composition prior to such storage) of aceclidine after storage for 6 months (e.g., at room temperature, such as up to 25 degrees Celsius). In certain embodiments, a composition provided herein comprises at least 95 wt. % of the initial amount (e.g., the amount of aceclidine in the composition prior to such storage) of aceclidine after storage for 6 months (e.g., at room temperature, such as up to 25 degrees Celsius).

In certain embodiments, a composition provided herein has been stored up to 3 months (e.g., at room temperature, such as up to 25 degrees Celsius). In certain embodiments, a composition provided herein comprises at least 90 wt. % of the initial amount (e.g., the amount of aceclidine in the composition prior to such storage) of aceclidine after storage for 3 months (e.g., at room temperature, such as up to 25 degrees Celsius). In certain embodiments, a composition provided herein comprises at least 95 wt. % of the initial amount (e.g., the amount of aceclidine in the composition prior to such storage) of aceclidine after storage for 3 months (e.g., at room temperature, such as up to 25 degrees Celsius).

In certain embodiments, a composition provided herein has been stored up to 2 weeks (e.g., at room temperature, such as up to 25 degrees Celsius). In certain embodiments, a composition provided herein comprises at least 90 wt. % of the initial amount (e.g., the amount of aceclidine in the composition prior to such storage) of aceclidine after storage for 2 weeks (e.g., at room temperature, such as up to 25 degrees Celsius). In certain embodiments, a composition provided herein comprises at least 95 wt. % of the initial amount (e.g., the amount of aceclidine in the composition prior to such storage) of aceclidine after storage for 2 weeks (e.g., at room temperature, such as up to 25 degrees Celsius).

In certain embodiments, an ophthalmological composition provided herein is stored at room temperature (e.g., up to 25° C.) (e.g., up to 3 months, such as for 2-3 months, or up to 6 months) prior to administration.

In certain embodiments, an ophthalmological composition provided herein is stored at 2° C. to 8° C. (e.g., up to 12 months or up to 18 months, such as for 12-18 months) prior to administration. In certain embodiments, an ophthalmological composition provided herein is stored at 2° C. to 8° C. up to 12 months prior to administration. In certain embodiments, an ophthalmological composition provided herein is stored at 2° C. to 8° C. up to 18 months prior to administration. In certain embodiments, an ophthalmological composition provided herein is stored at 2° C. to 8° C. up to 24 months prior to administration.

In certain embodiments, an ophthalmological composition provided herein comprises at least 95 wt. % of the aceclidine present in the composition prior to storage after the composition is stored at 2° C. to 8° C. up to 12 months. In certain embodiments, an ophthalmological composition provided herein comprises at least 95 wt. % of the aceclidine present in the composition prior to storage after the composition is stored at 2° C. to 8° C. up to 18 months. In certain embodiments, an ophthalmological composition provided herein comprises at least 95 wt. % of the aceclidine present in the composition prior to storage after the composition is stored at 2° C. to 8° C. up to 24 months.

In certain embodiments, a method provided comprises storing a composition (e.g., the system and container enclosing the composition) at elevated temperature (e.g., up to 40° C.) prior to use. In some embodiments, a method provided herein comprising using a composition (e.g., the system and container enclosing the composition) that has been stored at elevated temperature (e.g., up to 40° C.) prior to use. In certain embodiments, the composition is or has been stored for (e.g., up to) 8 days at elevated temperature (e.g., up to 40° C.) prior to use. In some instances, a composition comprises at least 90% of the initial amount (e.g., upon initial formulation) of aceclidine in the composition upon administration (e.g., after storing at refrigerated, elevated, and room temperature, such as described herein).

Concentration of the ophthalmological drug in a composition can be measured using any suitable technique known in the art. In some embodiments, a concentration of the ophthalmological drug is determined through any suitable analytical technique (e.g., liquid chromatography, titration, mass spectrometry, NMR, etc.). In some embodiments, High Pressure Liquid Chromatography (HPLC) is used to determine the concentration (e.g., purity and/or stability) of the ophthalmological drug in a composition. In some embodiments, a comparison of the concentration of the ophthalmological drug at a first time point and a second time point is an indicator of the stability of the ophthalmological drug in the composition and/or under storing conditions. For example, the concentration of aceclidine in a composition is measured to be about 1.75 wt. % at a first time point (e.g., when the composition is initially prepared) and is measured to be about 1.71 wt. % at a second point in time (e.g., after 12 months), therefore the percent aceclidine remaining in the composition is determined to be about 98% at the second point in time, which indicates the composition maintains good stability (e.g., minimal degradation) of aceclidine in the composition.

Provided in some embodiments herein is a method of treating presbyopia in an individual, the method comprising administering an ophthalmological composition to an eye of the individual. In some embodiments, the ophthalmological composition is administered according to any procedure or steps described herein.

Provided in some embodiments herein is a method of improving vision.

Provided in some embodiments herein is a method of improving near vision in an individual, the method comprising administering an ophthalmological composition to an eye of the individual. In some embodiments, the ophthalmological composition is administered according to any procedure or steps described herein.

Provided in some embodiments herein is a method of improving distant vision in an individual, the method comprising administering an ophthalmological composition to an eye of the individual. In some embodiments, the ophthalmological composition is administered according to any procedure or steps described herein.

In some embodiments, a method provided herein comprises administering a composition to an individual 45-75 years old. In some embodiments, a method provided herein comprises administering a composition to an individual 55-75 years old. In some embodiments, a method provided herein comprises administering a composition to an individual 65-75 years old. In some embodiments, a method provided herein comprises administering a composition to an individual 45-49 years old. In some embodiments, a method provided herein comprises administering a composition to an individual 50-55 years old. In some embodiments, a method provided herein comprises administering a composition to an individual 56-60 years old. In some embodiments, a method provided herein comprises administering a composition to an individual 61-65 years old. In some embodiments, a method provided herein comprises administering a composition to an individual 66-70 years old. In some instances, methods provided herein are surprisingly suitable for treating individuals in the 55-75 and 65-75 age groups, despite near vision loss generally being understood to be progressively worse as an individual ages.

In some embodiments, a method provided herein comprises administering a composition to an individual with a refractive range of −4D SE to +1D SE.

In some embodiments, a method provided herein comprises administering a composition to an individual with a near visual acuity of 20/50 or worse.

In some embodiments, a method provided herein is well tolerated. In some embodiments, a method provided herein is well tolerated in an individual to whom an ophthalmological composition is administered according to a method described herein.

In some embodiments, an ophthalmological composition is administered to an individual in accordance with a method provided herein at least once a week. In some embodiments, an ophthalmological composition is administered to an individual in accordance with a method provided herein at least twice a week. In some embodiments, an ophthalmological composition is administered to an individual in accordance with a method provided herein at least thrice a week. In some embodiments, an ophthalmological composition is administered to an individual in accordance with a method provided herein at least four times a week. In some embodiments, an ophthalmological composition is administered to an individual in accordance with a method provided herein daily. In some embodiments, an ophthalmological composition is administered to an individual in accordance with a method provided herein no more than once a day (e.g., 2 drops once a day per eye).

In some embodiments, an ophthalmological composition is administered to an individual in accordance with a method provided herein for at least one week. In some embodiments, an ophthalmological composition is administered to an individual in accordance with a method provided herein for at least two weeks. In some embodiments, an ophthalmological composition is administered to an individual in accordance with a method provided herein for at least three weeks. In some embodiments, an ophthalmological composition is administered to an individual in accordance with a method provided herein for at least four weeks. In some instances, daily administration of a composition provided herein provides substantially similar therapeutic benefit on day 28 as it does on day 1 (e.g., wherein the percent responders on day 28 is at least 80% of the percent responders on day 1, such as wherein a responder is as described herein (e.g., having a greater than 3-line improvement after 30 minutes, 1 hour, and/or 10 hours)).

In some embodiments, an ophthalmological composition provided herein does not comprise cycloplegic (e.g., tropicamide). In specific embodiments, the ophthalmological composition does not comprise tropicamide.

In some embodiments, a method provided herein further comprises administration of a second ophthalmological composition to an eye of an individual. In some embodiments, the second ophthalmological composition comprises a different active agent (not aceclidine or brimonidine). In certain embodiments, the ophthalmological composition or the second ophthalmological composition are administered at least 5 minutes after the last dose of the other of the ophthalmological composition or the second ophthalmological composition, which was administered first.

In some embodiments, the active agent of the second ophthalmological composition is any suitable agent, such as Moxifloxacin, Ciprofloxacin, Levofloxacin, Ofloxacin, Besifloxacin, Gatifloxacin, Azithromycin, Gentamicin, Tobramycin, Erythromycin, Bacitracin, Polymyxin B-Trimethoprim, Neomycin-Polymyxin B-Gramicidin, Neomycin-Polymyxin B-Bacitracin, Bacitracin-Polymyxin B, Sulfacetamide, Fluorometholone, Loteprednol, Rimexolone, Prenisolone, Difluprednate, Tobramycin-Loteprednol, Sulfacetamide sodium-Prednisolone, Neomycin-Bacitracin-Hydrocortisone, Neomycin-Polymyxin B-Dexamethasone, Tobramycin-Dexamethasone, Natamycin, Ganciclovir, Trifluiridine, Cysteamine, Cenegerminbkbj, Apraclonidine, Dorzolamide, Brinzolamide, Timolol, Betaxolol, Levobunolol, Metipranolol, Latanoprost, Bimatoprost, Travoprost, Tafluprost, Latanoprostene, Pilocarpine, Carbachol, Netarsudil, Dorzolamide+Timolol, Atropine, Scopolamine, Homatropine, Cyclopentolate, Tropicamide, Phenylephrine, or Hydroxyamphetamine.

In some embodiments, a method provided herein further comprises instillation of contact lens into an eye (e.g., onto a surface of an eye) of an individual.

In some embodiments, prior to administration of an ophthalmological composition provided herein (e.g., by a method described herein), the individual removes the contact lens from the eye of the individual.

In some embodiments, the individual inserts or reinserts the contact lens onto the eye at least about 10 minutes (e.g., at least about 15 minutes) after administering the second drop of the ophthalmological composition. In some instances, delay in instillation of the contact lens after administration of the ophthalmological composition is desirable to avoid interaction between the ophthalmological composition and the contact lens, such as to increase interaction between the ophthalmological composition and the ocular surface.

In some embodiments, provided herein is a method of reducing a corrective lens (e.g., bifocal or contact lens) wear time in an individual, the method comprising administering a composition comprising a miotic to an eye of the individual. In some embodiments, provided herein is a method of reducing a corrective lens (e.g., corrective glasses, such as bifocal, or contact lens) wear time in an individual, the method comprising administering a composition comprising a miotic to an eye of the individual.

In some embodiments, a lens is a bifocal glasses, progressive glasses, or a contact lens.

In certain embodiments, an individual treated according to a method provided herein is less dependent on wearing bifocals (e.g., glasses, progressive glasses, reading glasses), and/or contacts, such as during the workday. In certain embodiments, an individual treated according to a method provided herein is less dependent on wearing correctives glasses (e.g., bifocal glasses, progressive glasses, reading glasses), and/or contacts, such as during the workday.

In some embodiments, a method provided herein comprises inserting (e.g., reinserting) a contact lens onto an eye (e.g., an ocular surface thereof) about 5 minutes or more after administration of an ophthalmological composition provided herein. In some embodiments, a method provided herein comprises inserting (e.g., reinserting) a contact lens onto an eye (e.g., an ocular surface thereof) about 10 minutes or more after administration of an ophthalmological composition provided herein. In specific embodiments, a method provided herein comprises inserting (e.g., reinserting) a contact lens onto an eye (e.g., an ocular surface thereof) about 10 minutes after administration of an ophthalmological composition provided herein. In some embodiments, a method provided herein comprises inserting (e.g., reinserting) a contact lens onto an eye (e.g., an ocular surface thereof) about 15 minutes or more after administration of an ophthalmological composition provided herein.

In some embodiments, provided herein is a method of reducing a corrective lens (e.g., bifocal or contact lens) wear time in an individual described herein. In some embodiments, provided herein is a method of reducing a corrective lens (e.g., bifocal or contact lens) wear time in an individual described herein, the method comprising administering a composition comprising a miotic to an eye (e.g., an ocular surface thereof) of an individual described herein.

In some embodiments, reduction in corrective lens wear time in an individual described herein is for about 2 (e.g., continuous) hours or more. In some embodiments, reduction in corrective lens wear time in an individual described herein is for about 3 (e.g., continuous) hours or more. In some embodiments, reduction in corrective lens wear time in an individual described herein is for about 4 (e.g., continuous) hours or more. In some embodiments, reduction in corrective lens wear time in an individual described herein is for about 5 (e.g., continuous) hours or more. In some embodiments, reduction in corrective lens wear time in an individual described herein is for about 6 (e.g., continuous) hours or more. In some embodiments, reduction in corrective lens wear time in an individual described herein is for about 7 (e.g., continuous) hours or more. In some embodiments, reduction in corrective lens wear time in an individual described herein is for about 8 (e.g., continuous) hours or more.

In some embodiments, wear time of any desirable corrective lens is reduced according to a method provided herein such as for any desirable duration (e.g., a duration provided herein). In some embodiments, a corrective lens provided herein are any suitable corrective lens (e.g., bifocal glasses, progressive glasses, reading glasses, or contact lens). In specific embodiments, the corrective lens is bifocal glasses, progressive glasses, reading glasses, or a contact lens.

In some embodiments, provided herein is a method of reducing a corrective lens (e.g., bifocals glasses, progressive glasses, reading glasses, and/or contacts) wear time in an individual described herein, wherein (e.g., after administration of an ophthalmological composition provided herein) the individual is less dependent on wearing the corrective lens (e.g., relative to prior to administration of an ophthalmological composition provided herein).

In some embodiments, provided herein is a method of reducing a corrective lens (e.g., bifocals glasses, progressive glasses, reading glasses, and/or contacts) wear time in an individual described herein, wherein (e.g., after administration of an ophthalmological composition provided herein) the individual no longer requires wearing the corrective lens (e.g., on days when the ophthalmological composition is administered).

In some embodiments, provided herein is a method of reducing a corrective lens (e.g., bifocals glasses, progressive glasses, reading glasses, and/or contacts) wear time in an individual described herein, wherein the individual prior to administration of an ophthalmological composition provided herein regularly wears corrective lens for a substantial period of time and after administration of the ophthalmological composition no longer wears (or needs to wear) a corrective lens during the day (e.g., on days when the ophthalmological composition is administered). In specific embodiments, a substantial period of time provided herein is any undesirable duration of time. In some embodiments, a substantial period of time is at least half a day (e.g., during a workday, such as an 8 hour workday). In specific embodiments, a substantial period of time is a workday, such as an 8 hour workday.

In some embodiments, provided herein is a method of reducing a multi-powered corrective lens (e.g., bifocals glasses or progressive glasses) wear time in an individual described herein, wherein the individual prior to administration of an ophthalmological composition provided herein regularly wears the multi-powered corrective lens for a substantial period of time provided herein and after administration no longer wears (or needs to wear) a multi-powered corrective lens during the day (e.g., on days when the ophthalmological composition is administered). In some instances, prior to administration of an ophthalmological composition provided herein wears a bifocal or progressive glasses (e.g., for at least 4 hours a day). In some embodiments, no corrective lens is required after administration of an ophthalmological composition provided herein. In other embodiments, after administration of an ophthalmological composition provided herein, an individual described herein wears a single powered lens such as for treating myopia or astigmatism.

In some embodiments, an individual provided herein is a post-refractive surgery individual and wherein prior to administration of an ophthalmological composition provided herein and refractive surgery regularly, the individual wore a multi-powered corrective lens or at least half a day (e.g., during a workday, such as an 8 hour workday) and after administration of an ophthalmological composition provided herein and refractive surgery, the individual no longer wears (or needs to wear) a corrective lens during the day (e.g., prior to administration wears a bifocal or progressive glasses and after administration no longer wears any corrective lens).

In some embodiments, provided herein is a method for reducing contact lens wear time in an individual (e.g., in need thereof), the method comprising administering an ophthalmological composition comprising a miotic to an eye (e.g., an ocular surface thereof) of an individual described herein. In certain embodiments, the individual has presbyopia or myopia. In specific embodiments, the individual has presbyopia.

In certain embodiments, an individual treated according to a method provided herein is, following treatment, less dependent on or no longer requires wearing a bifocal glasses, progressive glasses, reading glasses, or a contact lens to correct near vision. In certain embodiments, the bifocal glasses, progressive glasses, reading glasses, or contact lens corrects near vision by at least +0.75. In certain embodiments, the bifocal glasses, progressive glasses, reading glasses, or contact lens corrects near vision by at least +1.5. In certain embodiments, the bifocal glasses, progressive glasses, reading glasses, or contact lens corrects near vision by at least +2.0. In certain embodiments, the bifocal glasses, progressive glasses, reading glasses, or contact lens corrects near vision by at least +2.5. In certain embodiments, the bifocal glasses, progressive glasses, reading glasses, or contact lens corrects near vision by at least +3.0. In certain embodiments, the bifocal glasses, progressive glasses, reading glasses, or contact lens corrects near vision by at least +3.5.

Provided in certain embodiments herein are systems, compositions, and methods, such as for improving ocular function, such as increasing comfortable screen time and/or treating presbyopia. In specific embodiments, provided herein are systems, compositions, and methods for increasing comfortable screen time.

In some embodiments, provided herein is a method for increasing comfortable screen time in an individual (e.g., in need thereof), the method comprising administering an ophthalmological composition comprising a miotic to an eye (e.g., an ocular surface thereof) of the individual. In certain embodiments, the individual has presbyopia or myopia. In specific embodiments, the individual has presbyopia.

EXAMPLES

Example 1A: Room Temperature Stable Formulations

Ophthalmic solutions comprising aceclidine hydrochloride (1.75%) were prepared. Formulation 1 was a solution prepared as a preservative-free, clear, colorless, sterile ophthalmic solution comprising aceclidine hydrochloride (1.75%) with a surfactant (polysorbate 80), a viscosity agent (hydroxypropylmethylcellulose (HPMC or Hypromellose)), a chelating agent (edetate disodium), a buffer (sodium citrate), and a tonicity agent (mannitol), and water (water for injection). The solution was adjusted to a pH of 4.5 to 5.5 using hydrochloric acid or sodium hydroxide, as needed. Formulation 2 was a solution prepared as a preservative-free, clear, colorless, sterile ophthalmic solution comprising aceclidine hydrochloride (1.75%) and brimonidine tartrate (0.08%) with a surfactant (polysorbate 80), a viscosity agent (hydroxypropylmethylcellulose (HPMC or Hypromellose)), a chelating agent (edetate disodium), a buffer (sodium citrate), and a tonicity agent (mannitol), and water (water for injection). The solution was adjusted to a pH of 4.5 to 5.5 using hydrochloric acid or sodium hydroxide, as needed.

Formulations 1 and 2 were separately configured into single-use vials with a 0.5 mL fill under air (e.g., class 4 air) and sealed. The formulations were stored at room temperature (25° C./60% RH) and evaluated by irreversibly opening a vial comprising the respective formulation at an initial time point, 1 month after the initial time point, and other time points up to 6 months after the initial time point. As demonstrated in Tables 1 and 2, good stability was achieved even after 6 months. Appearance was said to confirm if it was clear to opalescent, colorless to slightly yellow solution, and essentially free of visible particles.

TABLE 1

| Formulation 1 stability at 25° C./60% RH | | | | | |
|---|---|---|---|---|---|
| appearance | initial conforms | 1 month conforms | 2 month conforms | 3 month conforms | 6 month conforms |
| pH | 5.0 | 4.9 | 4.7 | 5.0 | 4.5 |
| aceclidine | 100.7% | 101.1% | 98.5% | 99.0% | 99.0% |

TABLE 2

| Formulation 2 stability at 25° C./60% RH | | | | |
|---|---|---|---|---|
| appearance | initial conforms | 1 month conforms | 3 month conforms | 6 month conforms |
| aceclidine | 102.5% | 103.6% | 103.8% | 104.1% |
| brimonidine | 101.8% | 100.1% | 102.4% | 104.7% |

The test was repeated, with similar results.

Example 1B: Effect on Stability in Aceclidine Solutions by Varying Formulation Various aqueous compositions were prepared similar to those described in Example 1A. Compositions were prepared with aceclidine at a concentration of about 1-2 wt. %. Compositions with varying amount of buffer (sodium citrate) were prepared. Compositions with varying pH were prepared. Compositions with varying viscosity agents (HPMC) were prepared. Compositions with and without preservative (BAK) were prepared.

Stability of aceclidine in each composition was determined as a percentage of aceclidine remaining in solution after storing in comparison to an initial amount of aceclidine present in each composition at baseline. HPLC methods were used to determine the concentration of aceclidine at each time point (e.g., initial time, after 1 month storing, after 2 months storing, after 3 months storing, after 4 months storing, after 6 months storing, after 9 months storing, after 12 months storing, and after 18 months storing).

Aqueous aceclidine solutions with pH values of 5.0, 5.5, 6.0, and 6.5 were prepared and evaluated for stability. Good refrigerated temperature (5° C.), room temperature (25° C.), and elevated temperature (40° C.) stability was observed for formulations having a pH of 6.0 and below with the best results observed at pH of about 5.5 and below.

FIGS. 1A-1D, FIGS. 2A-2D, and FIGS. 3A-3D illustrate stability (% aceclidine relative to initial aceclidine) of an exemplary aqueous aceclidine composition (solution) provided herein when stored at refrigerated (e.g., 2° C. to 8° C.), room temperature (e.g., up to 25° C.), and elevated (up to 40° C.). Specifically, FIG. 1A, FIG. 2A, and FIG. 3A, demonstrate excellent stability for compositions having a pH of 5, in a largely buffer independent manner. Excellent stability is demonstrated at buffer concentrations of 0.06%, 0.08%, and 0.1% (FIG. 1A, FIG. 2A, and FIG. 3A, respectively). All three formulations demonstrate >90% stability for aqueous aceclidine compositions (solutions) when stored for at least 6 months at room temperature and at least 18 months when refrigerated. All three formulations also demonstrate >90% stability when stored for at least 1 month at elevated temperature (40° C.). Similarly, FIG. 1B, FIG. 2B, and FIG. 3B, demonstrate excellent stability for compositions having a pH of 5.5, in a largely buffer independent manner. Excellent stability is demonstrated at buffer concentrations of 0.06%, 0.08%, and 0.1% (FIG. 1B, FIG. 2B, and FIG. 3B, respectively). All three formulations demonstrate >90% stability for aqueous aceclidine compositions (solutions) when stored for at least 6 months at room temperature and at least 18 months when refrigerated. All three formulations also demonstrate >90% stability when stored for at least 1 month at elevated temperature (40° C.). FIG. 1C, FIG. 2C, and FIG. 3C, demonstrate good stability (slightly less than at pH of 5 or 5.5) for compositions having a pH of 6, in a largely buffer independent manner. Good stability is demonstrated at buffer concentrations of 0.06%, 0.08%, and 0.1% (FIG. 1C, FIG. 2C, and FIG. 3C, respectively). All three formulations demonstrate >90% stability for aqueous aceclidine compositions (solutions) when stored for at least 6 months at room temperature and at least 18 months when refrigerated. All three formulations also demonstrate >90% stability when stored for at least 1 month at elevated temperature (40° C.). FIG. 1D, FIG. 2D, and FIG. 3D, demonstrate reduced stability (relative to pH of 5, 5.5, or 6) for compositions having a pH of 6.5, in a largely buffer independent manner. Stability is demonstrated at buffer concentrations of 0.06%, 0.08%, and 0.1% (FIG. 1D, FIG. 2D, and FIG. 3D, respectively). All three formulations demonstrate approximately 90% stability or less for aqueous aceclidine compositions (solutions) when stored for 6 months at room temperature. All three formulations also demonstrate <90% stability when stored for at least 1 month at elevated temperature (40° C.).

Aqueous aceclidine solutions with or without preservative (BAK) were prepared and evaluated for stability. Good refrigerated temperature, room temperature, and elevated temperature stability was observed for formulations with and without preservative. FIG. 4A and FIG. 4B demonstrate excellent stability in such aqueous aceclidine compositions (solutions) in a substantially preservative independent manner.

Figure 4C:
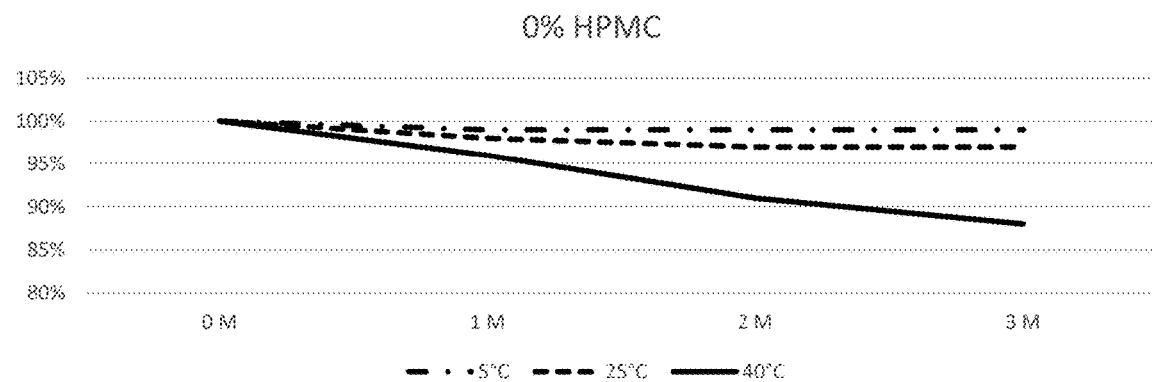
FIG. 4C, FIG. 4D, and FIG. 4E illustrate excellent stability in such aqueous aceclidine compositions (solutions) in a substantially viscosity agent (HPMC) independent manner.
Figure 4D:
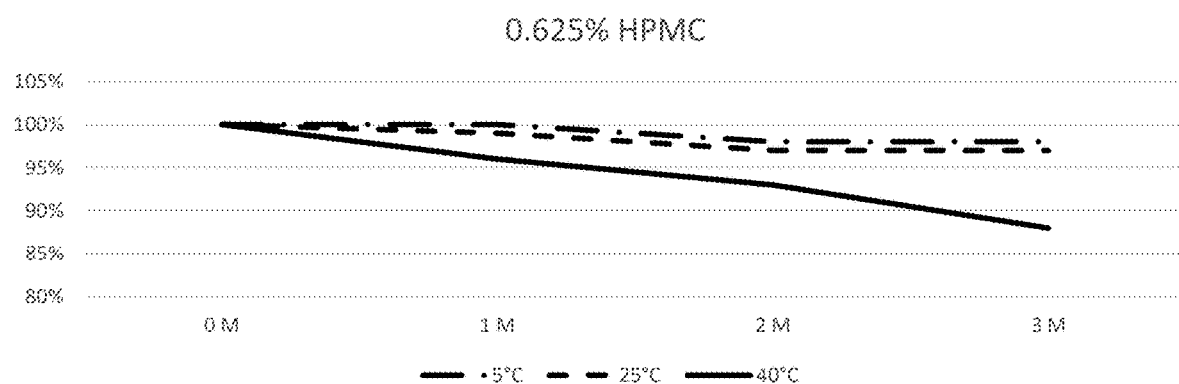
Figure 4E:
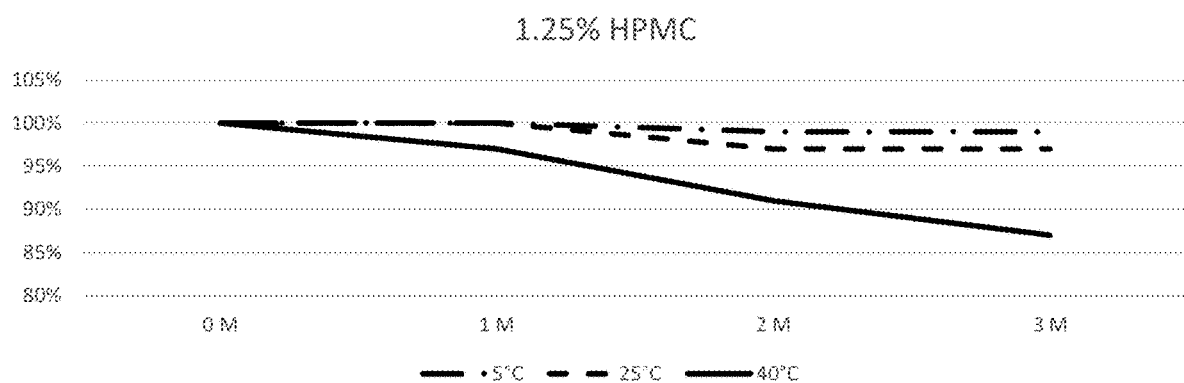

Aqueous aceclidine solutions with various concentrations (0 wt. %, 0.625 wt. %, and 1.25 wt. %) of viscosity agent (HPMC) were prepared and evaluated for stability. FIG. 4C (0 wt. %), FIG. 4D (0.625 wt. %), and FIG. 4E (1.25 wt. %) demonstrate excellent stability in such aqueous aceclidine compositions (solutions) in a substantially viscosity agent (HPMC) independent manner.

Surprisingly, control of pH was observed to play a substantial role in providing a formulation that had good room and elevated temperature stability, despite aceclidine aqueous solution generally being understood to be very difficult to formulate with good stability. Typically, aqueous aceclidine formulations have been considered to be very unstable, with aqueous aceclidine often being made by an end user at the time of use and discarded thereafter. It is also surprising that while control of pH was observed to have a strong effect on room temperature and elevated temperature, varying other components, such as buffer concentration, presence or lack of presence of a preservative, or concentration of viscosity agent, were not observed to have a substantial effect on aceclidine stability of aqueous aceclidine compositions described herein.

Example 2: Clinical Results for Evaluation of the Treatment of Presbyopia

A randomized, double-masked, multi-center, crossover study evaluation the efficacy of aceclidine (Formulation 1) or aceclidine and brimonidine (Formulation 2) in presbyopia was conducted. At the first study visit all subjects received preserved REFRESH TEARS® or similar placebo bilaterally as two drops approximately 1 to 5 minutes apart each drop administered. On subsequent study visits (2, 3, and 4), subjects received one of the following treatments based on randomized sequence they were assigned on the first visit: (1) aceclidine bilaterally as 2 drops administered with approximately 1 to 5 minutes apart between each drop; (2) aceclidine+brimonidine bilaterally as 2 drops administered with approximately 1 to 5 minutes apart between each drop, (3) vehicle bilaterally as 2 drops administered with approximately 1 to 5 minutes apart between each drop. All subjects received each treatment once (crossover study design). For pseudophakic subjects, intraocular lens must have been confirmed monofocal with no significant capsular opacification (PCO). Subjects who had undergone laser in situ keratomileusis (LASIK) or photorefractive keratectomy (PRK) surgery over 12 months prior to the first visit were permitted in the study, provided they met other inclusion criteria. Study duration was approximately 3 weeks, with the duration of each treatment being one day (two drops administered to each eye once).

Results for monocular best-corrected distance visual acuity (BCDVA, in logMAR Unit) at 40 cm was analyzed on a continuous scale are demonstrated in Table 3 for aceclidine and aceclidine+brimonidine

TABLE 3

Improved Visual Acuity at 40 cm for aceclidine and aceclidine + brimonidine

| Time Point | Aceclidine + Brimonidine | Aceclidine | Vehicle |
|---|---|---|---|
| n | 50 | 49 | 51 |
| Predose (mean(SD)) | 0.546 (0.0693) | 0.550 (0.0745) | 0.564 (0.0694) |
| 0.5 hr Post-dose | 0.216 (0.1527) | 0.167 (0.1264) | 0.434 (0.1118) |
| 1 hr Post-dose | 0.200 (0.1580) | 0.149 (0.1418) | 0.427 (0.1202) |
| 3 hr Post-dose | 0.194 (0.1554) | 0.162 (0.1331) | 0.447 (0.1091) |
| 5 hr Post-dose | 0.208 (0.1734) | 0.186 (0.1433) | 0.422 (0.0971) |
| 6 hr Post-dose | 0.198 (0.1692) | 0.198 (0.1560) | 0.424 (0.1087) |
| 7 hr Post-dose | 0.222 (0.1706) | 0.201 (0.1650) | 0.428 (0.1149) |
| 8 hr Post-dose | 0.234 (0.1654) | 0.242 (0.1543) | 0.438 (0.1189) |
| 9 hr Post-dose | 0.237 (0.1644) | 0.247 (0.1543) | 0.463 (0.1152) |
| 10 hr Post-dose | 0.264 (0.1741) | 0.285 (0.1672) | 0.462 (0.1128) |

Both aceclidine and aceclidine+brimonidine demonstrate substantial 40 cm visual acuity improvement starting within 0.5 hours and lasting at least 10 hours. Table 4 demonstrates the pupil response when treated with aceclidine and aceclidine+brimonidine

TABLE 4

Decreased pupil size for aceclidine and aceclidine + brimonidine

| Time Point | Aceclidine + Brimonidine | Aceclidine | Vehicle |
|---|---|---|---|
| n | 62 | 62 | 61 |
| Predose (mean(SD)) | 3.770 (1.1444) | 3.672 (1.1154) | 3.825 (1.3279) |
| 0.5 hr Post-dose | 1.762 (0.6959) | 1.649 (0.4945) | 3.381 (1.3439) |
| 1 hr Post-dose | 1.742 (0.6951) | 1.606 (0.5361) | 3.289 (1.2680) |
| 3 hr Post-dose | 1.703 (0.7170) | 1.639 (0.5345) | 3.452 (1.3695) |
| 4 hr Post-dose | 1.711 (0.7338) | 1.686 (0.5768) | 3.541 (1.3763) |
| 5 hr Post-dose | 1.731 (0.7330) | 1.755 (0.5663) | 3.469 (1.3926) |
| 6 hr Post-dose | 1.764 (0.7363) | 1.812 (0.5449) | 3.505 (1.4264) |
| 7 hr Post-dose | 1.807 (0.7356) | 1.898 (0.5761) | 3.459 (1.3316) |
| 8 hr Post-dose | 1.860 (0.7530) | 1.990 (0.6100) | 3.562 (1.4231) |
| 9 hr Post-dose | 1.939 (0.7692) | 2.062 (0.5807) | 3.532 (1.3497) |
| 10 hr Post-dose | 2.002 (0.7617) | 2.205 (0.6737) | 3.599 (1.3145) |

The tests were repeated, with similar results.

Example 3: Clinical Results for Evaluation of the Treatment of Presbyopia

A randomized, double masked, controlled phase 3 clinical study was conducted on patients aged 45-75 with a mean age of 55 years old. Patents had a refractive range of −4D SE to +1D SE. Patients included post-LASIK presbyopes and pseudophakes. Baseline near visual acuity was 20/50 or worse.

Equal cohorts of about 230 patients each were administered (1) aceclidine hydrochloride 1.75% formulation, (2) aceclidine hydrochloride 1.75% plus brimonidine tartrate 0.08% formulation, and (3) vehicle (control).

For the aceclidine hydrochloride 1.75% formulation, rapid onset and 10-hour duration 71%, 71% and 40% of participants was achieved with a ≥3-line improvement at 0.5, 3 and 10 hrs, respectively. Near universal response with 95% and 69% of participants was achieved with at least a 2-line improvement at 1 and 10 hours, respectively. Good response was achieved across demographics including age, gender, eye color, and LASIK/non-LASIK. Specifically, comparable responses were achieved in age groups including 45-49, 50-55, 56-60, 61-65, and 66-70. Good results were also achieved for individuals who wore reading glasses (including add powers of +0.75 up to +3.5) or progressive glasses at time points starting at 0.5 hours (post administration) up to 8 hours and up to 10 hours. In addition, 78% of individuals wearing the reading glasses reported being less dependent on the reading glasses and 70% of individuals wearing progressive glasses reported being less dependent on the progressive glasses. Consistent high response in near vision improvement was achieved over the 4-week efficacy study period. Treatment was well tolerated, with most AEs being mild and transient, having 30,000 treatment days without treatment related serious AE.

Figure 5:
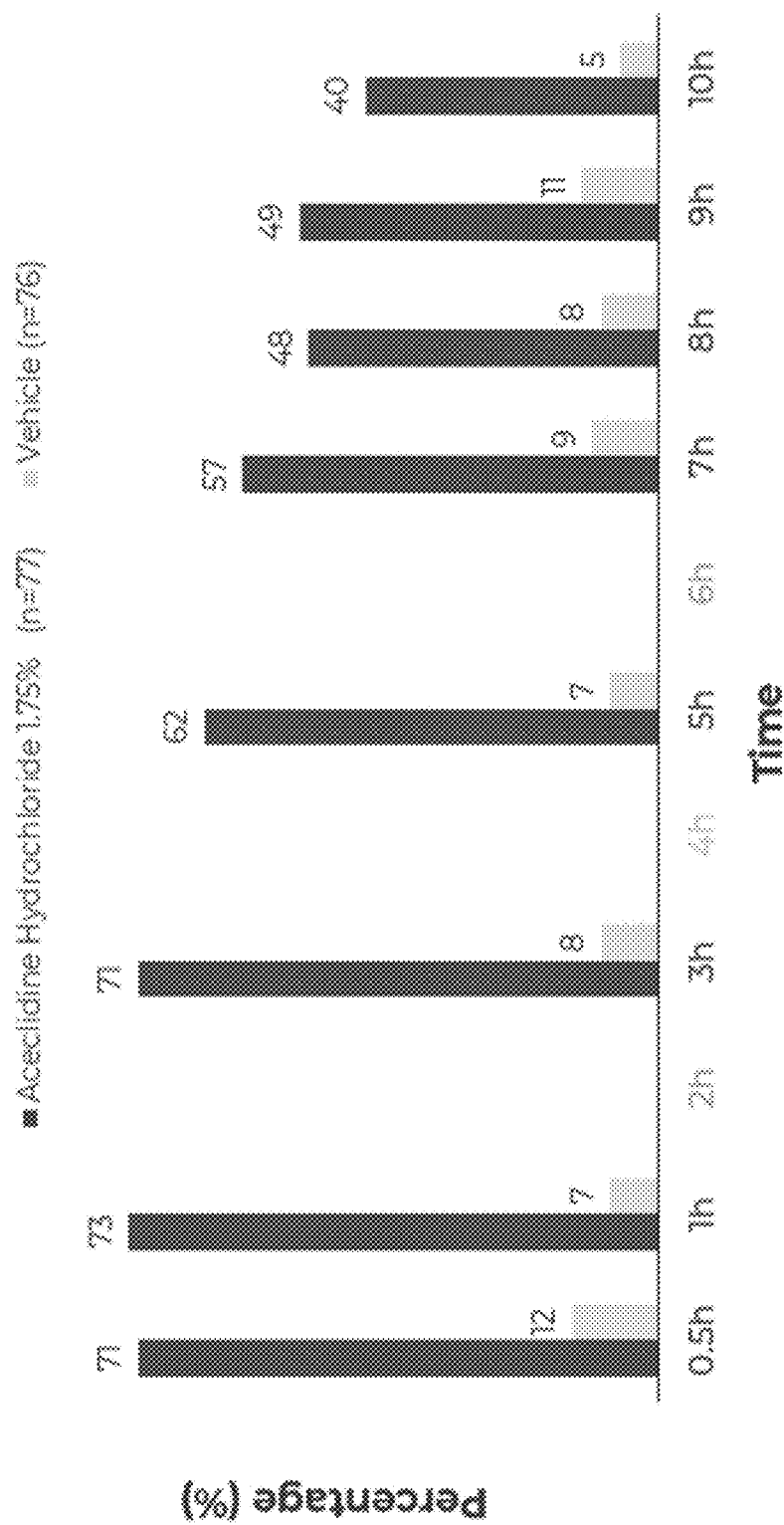
FIG. 5 illustrates rapid onset and extended duration of near vision improvement in individuals being treated with exemplary systems and methods described herein.

FIG. 5 illustrates percentage of participants achieving ≥3-line near vision improvement. Rapid onset with 71% of participants was achieved with 3-Line improvement at 30 min. 71% participants achieved ≥3-Line improvement at 3 hr, Extended duration with 40% response was achieved at 10 hours. Statistically significant results with p<0.0001 were achieved for all timepoints.

Figure 6:
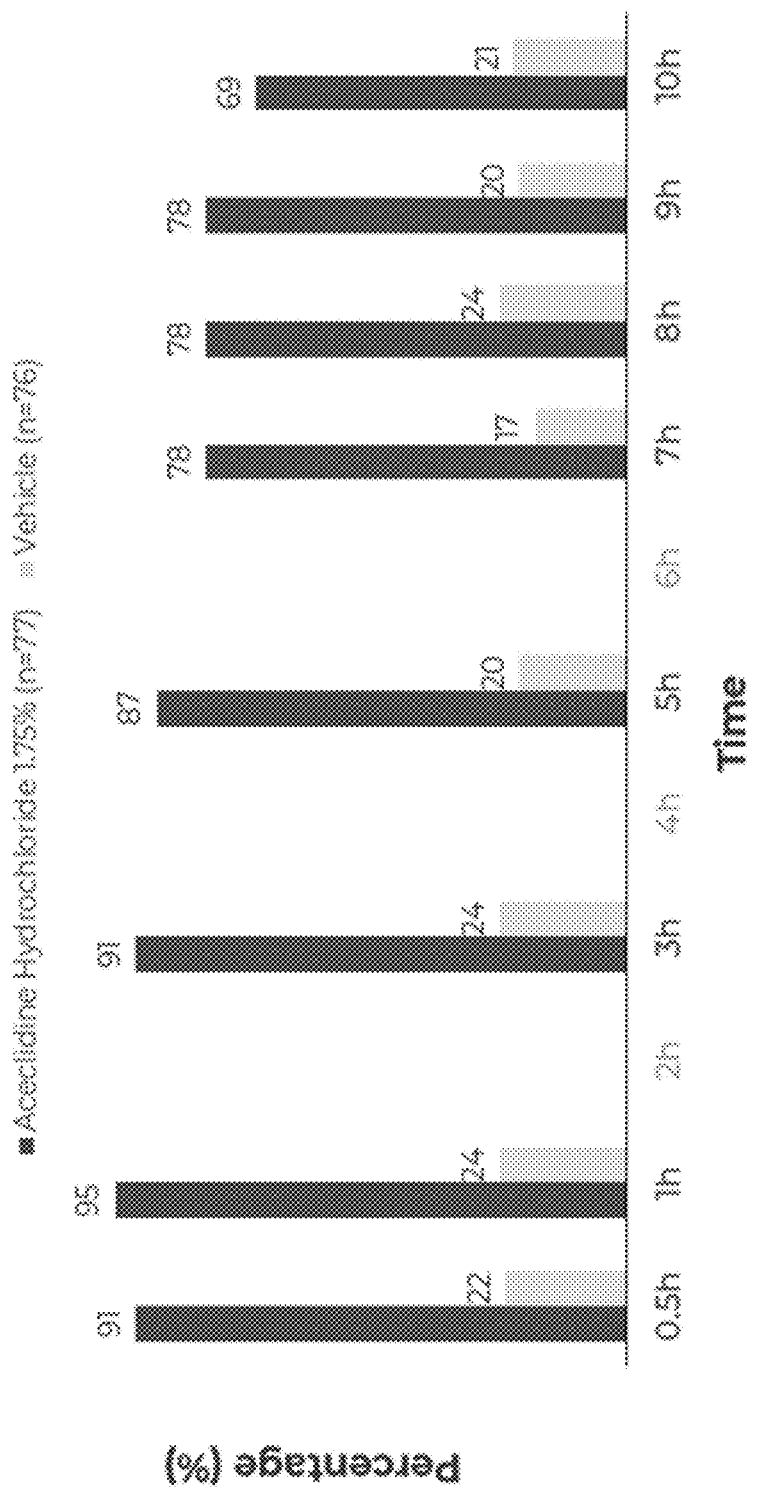
FIG. 6 illustrates near universal response of near vision improvement in individuals being treated with exemplary systems and methods described herein.

FIG. 6 illustrates percentage of participants achieving ≥2-line near vision improvement. 95% of participants achieved ≥2 line improvement at 1 hr. 69% of participants achieved ≥2 line improvement at 10 hrs. Statistically significant results with p<0.0001 were achieved for all timepoints. Pupil size were maintained between 1.5 mm and 2.35 mm for 10 hrs for full population.

Figure 7:
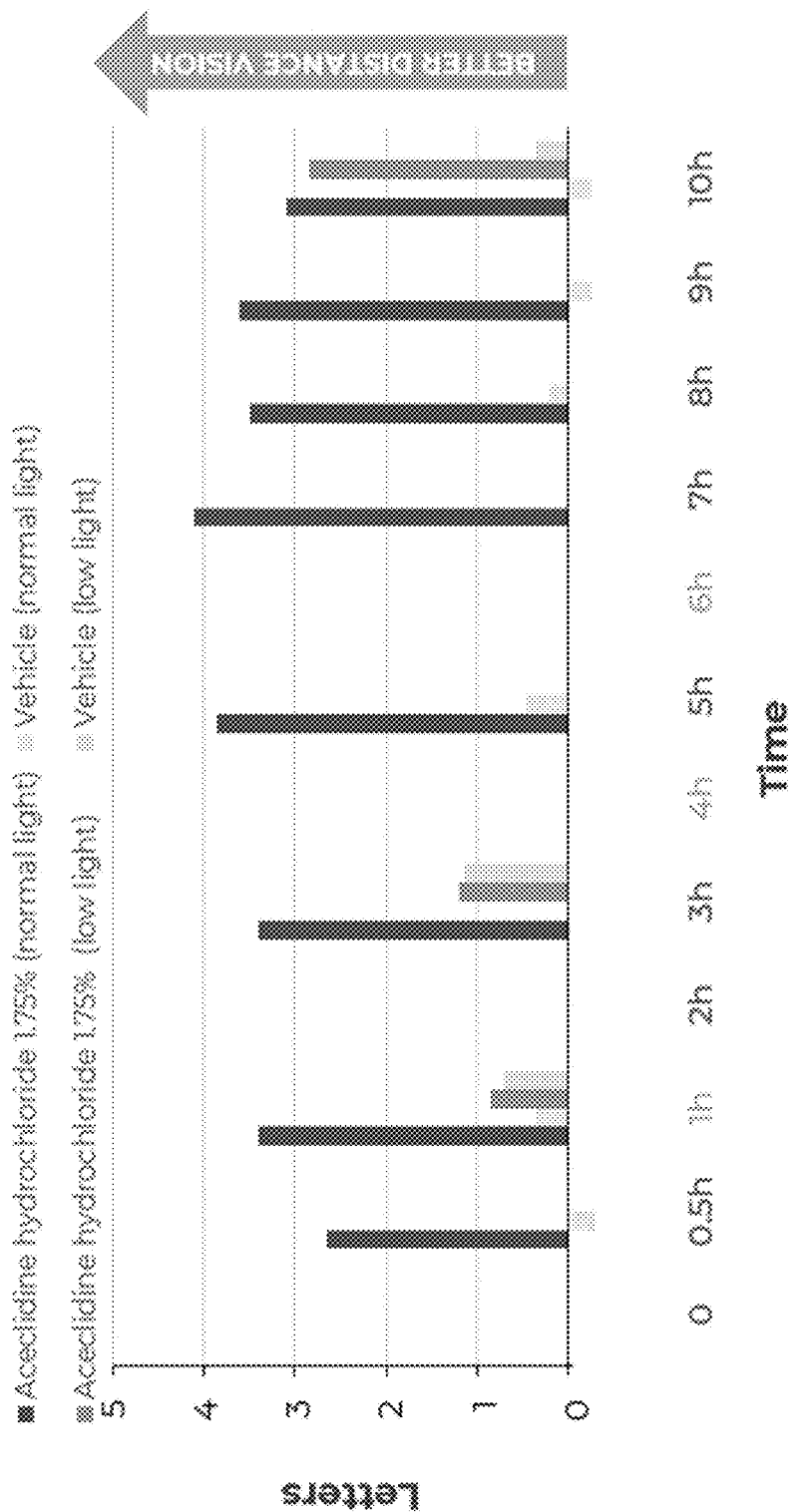
FIG. 7 illustrates distance vision improvement in individuals being treated with exemplary systems and methods described herein.

FIG. 7 illustrates improvement of 2-4 letters of distance vision. No negative impact to distance vision in normal and low light was observed. Statistically significant results with p<0.0001 were achieved for all timepoints.

Figure 8:
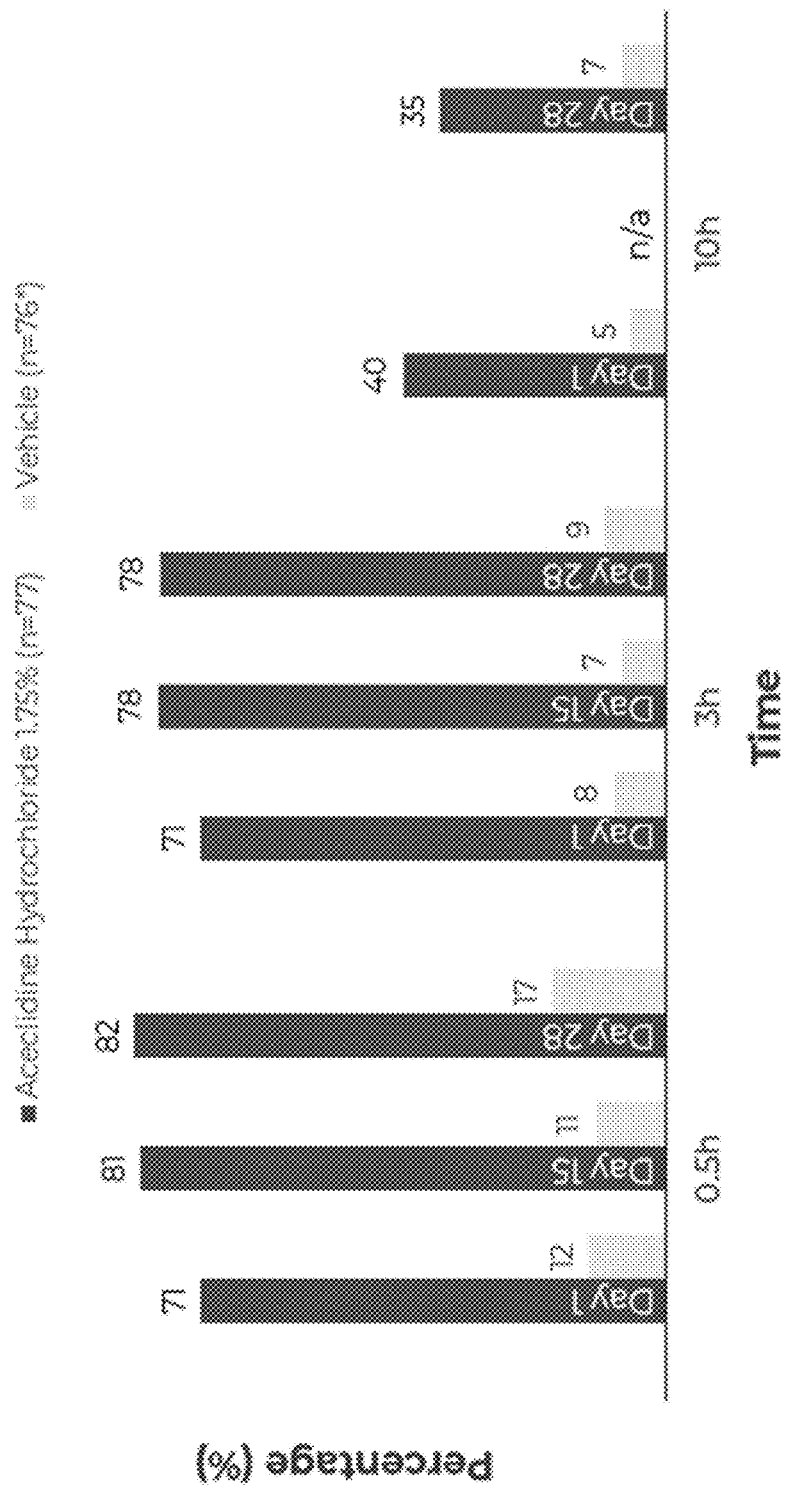
FIG. 8 illustrates consistent near vision improvement over 4 weeks in individuals being treated with exemplary systems and methods described herein.

FIG. 8 illustrates percentage of participants achieving ≥3-line near vision improvement over 28 days. Rapid onset at 0.5 hr, 71%, 81% and 82% of participants was achieved with a ≥3-line improvement at day 1, 15 and 28. At 3 hrs, 71%, 78% and 78% of participants was achieved with a ≥3-line improvement at day 1, 15 and 28. Extended duration at 10 hrs with 40% response at day 1 and 35% at day 28 were achieved. Reproducible and robust near vision improvement were observed across study days. The study was consistent and well-controlled with a low placebo response rate. Statistically significant results with p<0.0001 were achieved for all timepoints.

Figure 10:
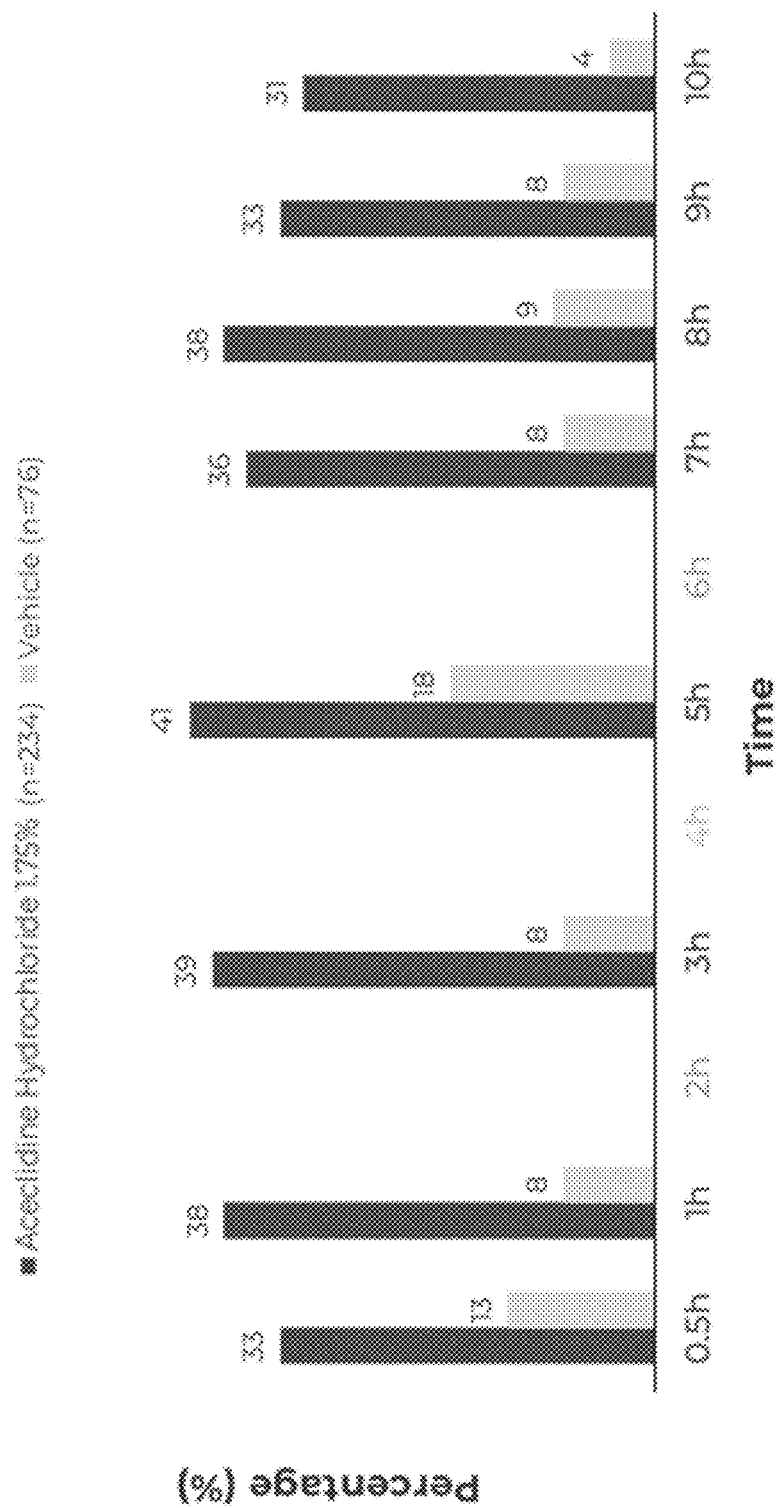
FIG. 10 illustrates distant vision improvement of at least 1 line.

FIG. 10 illustrates percentage of participants achieving at least 1 line distance vision improvement. Testing was done while participants were wearing their normal distance vision correction, as applicable.

Treatment was well tolerated, with most AEs being mild and transient, having 30,000 treatment days without treatment related serious AE. No serious treatment related adverse events were observed. Ocular treatment related AEs were classified as 100% mild by participants and investigators. Placebo corrected headache incidence was 7.6%. 89% of the headache were reported as mild. Ocular TEAEs and non-ocular TEAEs are shown in Table 5.

TABLE 5

Ocular TEAEs and non-ocular TEAEs.

| | aceclidine hydrochloride 1.75% formulation N = 234 n(%) | | Vehicle N = 76 n(%) |
|---|---|---|---|
| Ocular TEAEs | | | |
| Instillation site irritation (mild stinging upon instillation) | 47 (20.1%) | 100% mild | 8 (10.5%) |
| Visual impairment (mild dimness) | 31 (13.2%) | 100% mild | 1 (1.3%) |

TABLE 5-continued

Ocular TEAEs and non-ocular TEAEs.

|  | aceclidine hydrochloride 1.75% formulation N = 234 n(%) | Vehicle N = 76 n(%) | |
|---|---|---|---|
| Hyperemia (mild eye redness) | 21 (8.9%) | 100% mild | 2 (2.6%) |
| Non-Ocular TEAEs |  |  |  |
| Headache | 27 (11.5%) | 89% mild 7% moderate | 3 (3.9%) |

Aceclidine hydrochloride 1.75% plus brimonidine tartrate 0.08% formulation showed similar but not superior efficacy (data not shown).

Example 4: Exemplary Method for Determining Viscosity of Composition Provided Herein Formulations provided herein are analyzed for viscosity via USP <912> on both bulk and packaged formulations, using the Small Sample Adapter.

Brookfield Rotational Viscometer, equipped with LV spring and Small Sample Adapter, was used. Spindle #31 and a speed of 12 rpm was used. A recirculating Chiller was set at 20 degrees Celsius±0.1 degrees Celsius (temperature reading is measured on the viscometer, not the chiller).

Samples were prepared in a volume sufficient to perform the analysis (16-20 mL). The following protocol was performed to determine the viscosity as an average:
1. Transfer sample to the sample chamber, using care to avoid bubble formation.
2. Wait 5 minutes to allow for temperature equilibration.
3. Start rotation, allow the spindle to rotate for 2 min before taking the first measurement.
4. Stop rotation, pausing for a minimum of two minutes.
5. Start rotation, allow the spindle to rotate for 2 min before taking the second measurement.
6. Stop rotation, pausing for a minimum of two minutes.
7. Start rotation, allow the spindle to rotate for 2 min before taking the third measurement.
8. Stop rotation, remove and clean sample chamber.
9. Report the average of the three readings.

Various samples of Formulation 1 were measured for viscosity, with values of about 800 cP obtained. For example, a first composition had a viscosity of 807 cP, a second composition had a viscosity of 827 cP, and a third composition had a viscosity of 832 cP.

What is claimed is:

1. A method of treating presbyopia in an individual, the method comprising administering a first drop of an ophthalmological composition to an eye of the individual and subsequently administering a second drop of the ophthalmological composition to the eye of the individual, the ophthalmological composition comprising aceclidine or a salt thereof, the second drop being administered to the eye of the individual about 2 minutes after the first drop is administered to the eye, wherein the ophthalmological composition comprises aceclidine in a free base concentration of about 1.44 wt. %.

2. A method of treating presbyopia in an individual, the method comprising administering a first drop of an ophthalmological composition to an eye of the individual and subsequently administering a second drop of the ophthalmological composition to the eye of the individual, the ophthalmological composition comprising aceclidine or a salt thereof, the second drop being administered to the eye of the individual about 2 minutes after the first drop is administered to the eye, wherein following administration of the ophthalmological composition to the eye, the individual has 3-lines or more improvement in the eye within 0.5 hours of administering the second drop to the eye, and the individual has 3-lines or more improvement for at least 8 hours in the eye.

3. A method for treating presbyopia, the method comprising instilling one drop of an ophthalmological composition comprising aceclidine or a salt thereof in each eye followed by a second drop in each eye about two (2) minutes later for an effect of at least 10 hours, wherein the ophthalmological composition is preservative-free.

4. A method for treating presbyopia, the method comprising instilling one drop of an ophthalmological composition comprising aceclidine or a salt thereof in each eye followed by a second drop in each eye about two (2) minutes later for an effect of at least 10 hours, wherein no more than a first drop and a second drop of the ophthalmological composition is administered to the eye in a day.

5. The method of claim 1, wherein following administration of the ophthalmological composition to the eye, the individual has 3-lines or more improvement in the eye within 0.5 hours of administering the second drop to the eye, and the individual has 3-lines or more improvement for at least 8 hours in the eye.

6. The method of claim 1, wherein the ophthalmological composition is preservative-free.

7. The method of claim 1, wherein no more than a first drop and a second drop of the ophthalmological composition is administered to the eye in a day.

8. The method of claim 2, wherein the ophthalmological composition comprises aceclidine in a free base concentration of about 1.44 wt. %.

9. The method of claim 2, wherein the ophthalmological composition is preservative-free.

10. The method of claim 2, wherein no more than a first drop and a second drop of the ophthalmological composition is administered to the eye in a day.

11. The method of claim 3, wherein the ophthalmological composition comprises aceclidine in a free base concentration of about 1.44 wt. %.

12. The method of claim 3, wherein following administration of the ophthalmological composition to the eye, the individual has 3-lines or more improvement in the eye within 0.5 hours of administering the second drop to the eye, and the individual has 3-lines or more improvement for at least 8 hours in the eye.

13. The method of claim 3, wherein no more than a first drop and a second drop of the ophthalmological composition is administered to the eye in a day.

14. The method of claim 4, wherein the ophthalmological composition comprises aceclidine in a free base concentration of about 1.44 wt. %.

15. The method of claim 4, wherein following administration of the ophthalmological composition to the eye, the individual has 3-lines or more improvement in the eye within 0.5 hours of administering the second drop to the eye, and the individual has 3-lines or more improvement for at least 8 hours in the eye.

16. The method of claim 4, wherein the ophthalmological composition is preservative-free.

* * * * *